(12) United States Patent
Woehr et al.

(10) Patent No.: US 11,141,569 B2
(45) Date of Patent: Oct. 12, 2021

(54) CATHETER DEVICES WITH VALVES AND RELATED METHODS

(71) Applicant: B. Braun Melsungen AG, Melsungen (DE)

(72) Inventors: Kevin Woehr, Felsberg (DE); Jarryd Keng Gene Ng, Penang (MY); Boon Ping Neoh, Penang (MY)

(73) Assignee: B. Braun Melsungen AG, Melsungen (DE)

( * ) Notice: Subject to any disclaimer, the term of this patent is extended or adjusted under 35 U.S.C. 154(b) by 184 days.

(21) Appl. No.: 15/747,305

(22) PCT Filed: Aug. 18, 2016

(86) PCT No.: PCT/EP2016/069619
§ 371 (c)(1),
(2) Date: Jan. 24, 2018

(87) PCT Pub. No.: WO2017/029361
PCT Pub. Date: Feb. 23, 2017

(65) Prior Publication Data
US 2018/0214682 A1    Aug. 2, 2018

Related U.S. Application Data

(60) Provisional application No. 62/206,481, filed on Aug. 18, 2015, provisional application No. 62/301,917, filed on Mar. 1, 2016.

(51) Int. Cl.
*A61M 25/06* (2006.01)
*A61M 39/06* (2006.01)
(Continued)

(52) U.S. Cl.
CPC ..... *A61M 25/0606* (2013.01); *A61B 5/15003* (2013.01); *A61M 25/0618* (2013.01);
(Continued)

(58) Field of Classification Search
CPC .......... A61M 25/0606; A61M 25/0618; A61M 39/0693; A61M 25/0693; A61M 2039/062; A61M 2039/064; A61M 2039/0666
See application file for complete search history.

(56) References Cited

U.S. PATENT DOCUMENTS

| | | |
|---|---|---|
| 4,387,879 A | 6/1983 | Tauschinski |
| 4,424,833 A | 1/1984 | Spector et al. |

(Continued)

FOREIGN PATENT DOCUMENTS

| | | |
|---|---|---|
| CN | 101610809 A | 12/2009 |
| CN | 101808692 A | 8/2010 |

(Continued)

OTHER PUBLICATIONS

International Search Report & Written Opinion on corresponding PCT application (PCT/EP 2016/069619) from International Searching Authority (EPO) dated Dec. 8, 2016.
(Continued)

*Primary Examiner* — Nathan R Price
*Assistant Examiner* — Melissa A Snyder
(74) *Attorney, Agent, or Firm* — Klein, O'Neill & Singh, LLP

(57) ABSTRACT

Needle assemblies and related methods in which a valve opener is used to push into a valve to open one or more slits on the valve to open the valve. The needle assemblies each includes a needle hub with a needle, a catheter tube with a catheter hub and the valve and valve opener positioned in the interior cavity of the catheter hub. The valve can have a valve skirt and a nose section of the valve opener can locate therein. One or more reliefs can be provided with the valve
(Continued)

opener so that an elbow or diagonal section on a needle guard can project from a holding space within the valve opener through the relief.

27 Claims, 18 Drawing Sheets

(51) Int. Cl.
  *A61M 39/02* (2006.01)
  *A61B 5/15* (2006.01)
(52) U.S. Cl.
  CPC .... *A61M 39/0208* (2013.01); *A61M 39/0247* (2013.01); *A61M 39/06* (2013.01); *A61M 39/0613* (2013.01); *A61M 39/0693* (2013.01); *A61M 25/0693* (2013.01); *A61M 2039/027* (2013.01); *A61M 2039/0258* (2013.01); *A61M 2039/062* (2013.01); *A61M 2039/064* (2013.01); *A61M 2039/0666* (2013.01); *A61M 2207/00* (2013.01)

(56) References Cited

U.S. PATENT DOCUMENTS

| | | |
|---|---|---|
| 4,436,519 A | 3/1984 | O'Neill |
| 4,512,766 A | 4/1985 | Vailancourt |
| 4,673,393 A | 6/1987 | Suzuki et al. |
| 4,683,916 A | 8/1987 | Raines |
| 4,842,591 A | 6/1989 | Luther |
| 4,874,377 A | 10/1989 | Newgard et al. |
| 4,909,798 A | 3/1990 | Fleischhacker et al. |
| 4,917,668 A | 4/1990 | Haindl |
| 5,053,014 A | 10/1991 | Van Heughten |
| 5,062,836 A | 11/1991 | Wendell |
| 5,064,416 A | 11/1991 | Newgard et al. |
| 5,085,645 A | 2/1992 | Purdy et al. |
| 5,114,408 A | 5/1992 | Fleischhaker et al. |
| 5,134,996 A | 8/1992 | Bell |
| 5,154,703 A | 10/1992 | Bonaldo |
| 5,188,607 A | 2/1993 | Wu |
| 5,234,410 A | 8/1993 | Graham et al. |
| 5,242,393 A | 9/1993 | Brimhall et al. |
| 5,254,098 A | 10/1993 | Ulrich et al. |
| 5,269,763 A | 12/1993 | Boehmer et al. |
| 5,269,768 A | 12/1993 | Cheung |
| 5,300,043 A | 4/1994 | Devlin et al. |
| 5,330,435 A | 7/1994 | Vaillancourt |
| 5,342,315 A | 8/1994 | Rowe et al. |
| 5,349,950 A | 9/1994 | Ulrich et al. |
| 5,350,363 A | 9/1994 | Goode et al. |
| 5,409,461 A | 4/1995 | Steinman |
| 5,419,766 A | 5/1995 | Chang et al. |
| 5,419,769 A | 5/1995 | Devlin et al. |
| 5,429,616 A | 7/1995 | Schaffer |
| 5,456,284 A | 10/1995 | Ryan et al. |
| 5,458,640 A | 10/1995 | Gerrone |
| 5,460,613 A | 10/1995 | Ulrich et al. |
| 5,476,451 A | 12/1995 | Ensminger et al. |
| 5,480,385 A | 1/1996 | Thorne et al. |
| 5,490,503 A | 2/1996 | Hollister |
| 5,501,674 A | 3/1996 | Trombley, III et al. |
| 5,514,116 A | 5/1996 | Vaillancourt et al. |
| 5,531,720 A | 7/1996 | Atkins |
| 5,533,708 A | 7/1996 | Atkinson et al. |
| 5,542,927 A | 8/1996 | Thorne et al. |
| 5,542,933 A | 8/1996 | Marks |
| 5,607,407 A | 3/1997 | Tolkoff et al. |
| 5,611,782 A | 3/1997 | Haedt |
| 5,613,663 A | 3/1997 | Schmidt et al. |
| 5,628,732 A | 5/1997 | Antoon, Jr. et al. |
| 5,685,866 A | 11/1997 | Lopez |
| 5,688,253 A | 11/1997 | Paradis |
| 5,704,914 A | 1/1998 | Stocking et al. |
| 5,727,770 A | 3/1998 | Dennis |
| 5,749,857 A | 5/1998 | Cuppy |
| 5,755,709 A | 5/1998 | Cuppy |
| 5,759,179 A | 6/1998 | Balbierz |
| 5,792,104 A | 8/1998 | Speckman et al. |
| 5,797,880 A | 8/1998 | Erskine |
| 5,800,395 A | 9/1998 | Botich et al. |
| 5,810,835 A | 9/1998 | Ryan et al. |
| 5,817,069 A | 10/1998 | Arnett |
| 5,830,228 A | 11/1998 | Knapp et al. |
| 5,833,662 A | 11/1998 | Stevens |
| 5,843,046 A | 12/1998 | Motisi et al. |
| 5,853,394 A | 12/1998 | Tolkoff et al. |
| 5,858,002 A | 1/1999 | Jesch |
| 5,865,806 A | 2/1999 | Howell |
| 5,911,706 A | 6/1999 | Estabrook et al. |
| 5,911,710 A | 6/1999 | Barry et al. |
| 5,935,110 A | 8/1999 | Brimhall |
| 5,954,698 A | 9/1999 | Pike |
| 5,968,068 A | 10/1999 | Dehdashtian et al. |
| 5,976,110 A | 11/1999 | Greengrass et al. |
| 6,007,519 A | 12/1999 | Rosselli |
| 6,013,058 A | 1/2000 | Prosl et al. |
| 6,024,727 A | 2/2000 | Thorne et al. |
| 6,024,729 A | 2/2000 | Dehdashtian et al. |
| 6,056,760 A | 5/2000 | Koike et al. |
| 6,074,371 A | 6/2000 | Fischell |
| 6,113,572 A | 9/2000 | Gailey et al. |
| 6,132,402 A | 10/2000 | Tessmann et al. |
| 6,171,287 B1 | 1/2001 | Lynn et al. |
| 6,213,978 B1 | 4/2001 | Voyten |
| 6,217,554 B1 | 4/2001 | Green |
| 6,217,556 B1 | 4/2001 | Ellingson et al. |
| 6,258,065 B1 | 7/2001 | Dennis et al. |
| 6,299,602 B1 | 10/2001 | Miller et al. |
| 6,352,520 B1 | 3/2002 | Miyazaki |
| 6,371,963 B1 | 4/2002 | Nishtala et al. |
| 6,379,337 B1 | 4/2002 | Mohammad |
| 6,482,186 B1 | 11/2002 | Douglas et al. |
| 6,485,473 B1 | 11/2002 | Lynn |
| 6,506,181 B2 | 1/2003 | Meng et al. |
| 6,533,759 B1 | 3/2003 | Watson et al. |
| 6,544,235 B2 | 4/2003 | Motisi et al. |
| 6,610,045 B2 | 8/2003 | Chavez et al. |
| 6,616,630 B1 | 9/2003 | Woehr et al. |
| 6,620,136 B1 | 9/2003 | Pressley, Sr. et al. |
| 6,699,221 B2 | 3/2004 | Vaillancourt |
| 6,719,726 B2 | 4/2004 | Meng et al. |
| 6,740,063 B2 | 5/2004 | Lynn |
| 6,746,420 B1 | 6/2004 | Prestidge et al. |
| 6,764,468 B1 | 7/2004 | East |
| 6,860,869 B2 | 3/2005 | Dennis |
| 6,921,386 B2 | 7/2005 | Shue et al. |
| 6,921,391 B1 | 7/2005 | Barker et al. |
| 6,981,969 B2 | 1/2006 | Chavez et al. |
| 7,008,404 B2 | 3/2006 | Nakajima |
| 7,048,729 B2 | 5/2006 | Meglin et al. |
| 7,052,507 B2 | 5/2006 | Wakuda et al. |
| 7,120,487 B2 | 10/2006 | Nelson |
| 7,125,396 B2 | 10/2006 | Leinsing et al. |
| 7,156,827 B2 | 1/2007 | McNary et al. |
| 7,214,215 B2 | 5/2007 | Heinzerling et al. |
| 7,270,649 B2 | 9/2007 | Fitzgerald |
| 7,311,708 B2 | 12/2007 | McClurken |
| 7,347,839 B2 | 3/2008 | Hiejima |
| 7,470,254 B2 | 12/2008 | Basta et al. |
| 7,537,595 B2 | 5/2009 | McClurken |
| 7,625,346 B2 | 12/2009 | Grigoryants et al. |
| 7,632,243 B2 | 12/2009 | Bialecki et al. |
| 7,632,262 B2 | 12/2009 | Bates |
| 7,635,357 B2 | 12/2009 | Mayer |
| 7,641,669 B2 | 1/2010 | Roychowdhury et al. |
| 7,666,166 B1 | 2/2010 | Emmert et al. |
| 7,670,317 B2 | 3/2010 | Cindrich et al. |
| 7,670,322 B2 | 3/2010 | Fangrow, Jr. |
| 7,691,093 B2 | 4/2010 | Brimhall |
| 7,695,458 B2 | 4/2010 | Belley et al. |
| 7,713,257 B2 | 5/2010 | Brimhall et al. |
| 7,736,337 B2 | 6/2010 | Diep et al. |

(56) References Cited

U.S. PATENT DOCUMENTS

| | | |
|---|---|---|
| 7,736,339 B2 | 6/2010 | Woehr et al. |
| 7,758,514 B2 | 7/2010 | Grigoryants et al. |
| 7,789,861 B2 | 9/2010 | Franer |
| 7,806,869 B2 | 10/2010 | Nilsson et al. |
| 7,914,494 B2 | 3/2011 | Hiejima |
| 7,914,496 B2 | 3/2011 | Brockmeier et al. |
| 7,955,346 B2 | 6/2011 | Mauch et al. |
| 8,002,750 B2 | 8/2011 | Smith |
| 8,006,953 B2 | 8/2011 | Bennett |
| 8,029,472 B2 | 10/2011 | Leinsing et al. |
| 8,042,689 B2 | 10/2011 | Fröjd et al. |
| 8,048,039 B2 | 11/2011 | Carlyon et al. |
| 8,056,756 B2 | 11/2011 | Okiyama |
| 8,066,670 B2 | 11/2011 | Cluff et al. |
| 8,066,675 B2 | 11/2011 | Cindrich et al. |
| 8,123,727 B2 | 2/2012 | Luther et al. |
| 8,147,413 B2 | 4/2012 | Abraham |
| 8,147,455 B2 | 4/2012 | Butts et al. |
| 8,152,755 B1 | 4/2012 | Wach et al. |
| 8,172,757 B2 | 5/2012 | Jaffe et al. |
| 8,202,253 B1 | 6/2012 | Wexler |
| 8,206,357 B2 | 6/2012 | Bettuchi |
| 8,206,375 B2 | 6/2012 | Snow |
| 8,257,313 B2 | 9/2012 | McKinnon et al. |
| 8,257,339 B1 | 9/2012 | Rosado |
| 8,262,623 B2 | 9/2012 | Nijland et al. |
| 8,286,657 B2 | 10/2012 | Belley et al. |
| 8,308,655 B2 | 11/2012 | Grigoryants et al. |
| 8,308,691 B2 | 11/2012 | Woehr et al. |
| 8,323,249 B2 | 12/2012 | White et al. |
| 8,328,762 B2 | 12/2012 | Woehr et al. |
| 8,333,735 B2 | 12/2012 | Woehr et al. |
| 8,337,463 B2 | 12/2012 | Woehr et al. |
| 8,348,844 B2 | 1/2013 | Kunjan et al. |
| 8,361,038 B2 | 1/2013 | McKinnon et al. |
| 8,366,684 B2 | 2/2013 | Harding |
| 8,388,583 B2 | 3/2013 | Stout et al. |
| 8,419,688 B2 | 4/2013 | Woehr et al. |
| 8,454,579 B2 | 6/2013 | Fangrow, Jr. |
| 8,460,247 B2 | 6/2013 | Woehr et al. |
| 8,465,461 B2 | 6/2013 | Wu et al. |
| 8,469,928 B2 | 6/2013 | Stout et al. |
| 8,470,025 B2 | 6/2013 | Lenihan et al. |
| 8,506,533 B2 | 8/2013 | Carlyon et al. |
| 8,506,534 B2 | 8/2013 | Luther et al. |
| 8,518,013 B2 | 8/2013 | Kurrus et al. |
| 8,535,271 B2 | 9/2013 | Fuchs et al. |
| 8,540,728 B2 | 9/2013 | Woehr et al. |
| 8,562,520 B2 | 10/2013 | Rockrohr |
| 8,585,651 B2 | 11/2013 | Asai |
| 8,591,468 B2 | 11/2013 | Woehr et al. |
| 8,597,249 B2 | 12/2013 | Woehr et al. |
| 8,597,252 B2 | 12/2013 | Burkholz et al. |
| 8,608,727 B2 | 12/2013 | Michels et al. |
| 8,608,728 B2 | 12/2013 | Michels et al. |
| 8,622,972 B2 | 1/2014 | Nystrom et al. |
| 8,628,056 B2 | 1/2014 | LaBean et al. |
| 8,636,695 B2 | 1/2014 | Cluff et al. |
| 8,641,675 B2 | 2/2014 | Stout et al. |
| 8,641,676 B2 | 2/2014 | Butts et al. |
| 8,647,301 B2 | 2/2014 | Bialecki et al. |
| 8,652,104 B2 | 2/2014 | Goral et al. |
| 8,663,169 B2 | 3/2014 | Emmert et al. |
| 8,668,674 B2 | 3/2014 | White et al. |
| 8,679,063 B2 | 3/2014 | Stout et al. |
| 8,690,815 B2 | 4/2014 | Porter et al. |
| 8,690,833 B2 | 4/2014 | Belson |
| 8,715,242 B2 | 5/2014 | Helm, Jr. |
| 8,728,030 B2 | 5/2014 | Woehr |
| 8,740,850 B2 | 6/2014 | Leinsing et al. |
| 8,771,230 B2 | 7/2014 | White et al. |
| 8,790,310 B2 | 7/2014 | White et al. |
| 8,831,707 B2 | 9/2014 | Tekulve et al. |
| 8,864,715 B2 | 10/2014 | Cluff et al. |
| 8,882,742 B2 | 11/2014 | Dikeman et al. |
| 8,926,494 B1 | 1/2015 | Cook et al. |
| 8,932,257 B2 | 1/2015 | Woehr |
| 8,932,258 B2 | 1/2015 | Blanchard et al. |
| 8,932,259 B2 | 1/2015 | Stout et al. |
| 8,939,938 B2 | 1/2015 | Funamura et al. |
| 8,968,252 B2 | 3/2015 | White et al. |
| 8,979,802 B2 | 3/2015 | Woehr |
| 8,998,852 B2 | 4/2015 | Blanchard et al. |
| 9,011,382 B2 | 4/2015 | Nilsson et al. |
| 9,028,393 B2 | 5/2015 | Farnan |
| 9,089,671 B2 | 7/2015 | Stout et al. |
| 9,095,679 B2 | 8/2015 | Nishimura et al. |
| 9,108,021 B2 | 8/2015 | Hyer et al. |
| 9,114,231 B2 | 8/2015 | Woehr et al. |
| 9,114,241 B2 | 8/2015 | Stout et al. |
| 9,149,625 B2 | 10/2015 | Woehr et al. |
| 9,149,626 B2 | 10/2015 | Woehr et al. |
| 9,155,863 B2 | 10/2015 | Isaacson et al. |
| 9,155,864 B2 | 10/2015 | Stout et al. |
| 9,180,275 B2 | 11/2015 | Helm |
| 9,186,455 B2 | 11/2015 | Moyer |
| 9,220,833 B2 | 12/2015 | Robert et al. |
| 9,227,038 B2 | 1/2016 | Woehr |
| 9,227,047 B2 | 1/2016 | Khalaj |
| RE45,896 E | 2/2016 | Stout et al. |
| 9,272,088 B2 | 3/2016 | Bornhoft |
| 9,314,201 B2 | 4/2016 | Burkholz et al. |
| 9,320,870 B2 | 4/2016 | Woehr |
| 9,327,095 B2 | 5/2016 | Ma |
| 9,352,119 B2 | 5/2016 | Burkholz et al. |
| 9,370,641 B2 | 6/2016 | Woehr et al. |
| 9,381,320 B2 | 7/2016 | Vincent et al. |
| 9,381,324 B2 | 7/2016 | Fuchs et al. |
| 9,399,116 B2 | 7/2016 | Goral et al. |
| 9,427,549 B2 | 8/2016 | Wooehr et al. |
| 9,545,632 B2 | 1/2017 | Lentz et al. |
| 9,579,486 B2 | 2/2017 | Burkholz et al. |
| 9,592,366 B2 | 3/2017 | White et al. |
| 9,623,210 B2 | 4/2017 | Woehr |
| 9,737,252 B2 | 8/2017 | Teoh et al. |
| 9,750,920 B2 | 9/2017 | Vincent et al. |
| 9,764,085 B2 | 9/2017 | Teoh |
| 9,844,648 B2 | 12/2017 | Nakajima et al. |
| 9,919,136 B2 | 3/2018 | Lim et al. |
| 9,962,525 B2 | 5/2018 | Woehr |
| 10,004,891 B2 | 6/2018 | Woehr |
| 10,080,869 B2 | 9/2018 | Woehr et al. |
| 10,166,370 B2 | 1/2019 | Woehr et al. |
| 10,173,002 B2 | 1/2019 | Tan et al. |
| 10,207,081 B2 | 2/2019 | Fuchs et al. |
| 10,286,185 B2 | 5/2019 | Tanabe et al. |
| 10,376,686 B2 | 8/2019 | Burkholz et al. |
| 10,449,331 B2 | 10/2019 | Lim et al. |
| 10,456,572 B2 | 10/2019 | Woehr |
| 10,463,395 B2 | 11/2019 | Reid et al. |
| 10,463,839 B2 | 11/2019 | Woehr |
| 10,493,262 B2 | 12/2019 | Tran et al. |
| 10,500,376 B2 | 12/2019 | Isaacson et al. |
| 10,543,343 B2 | 1/2020 | Woehr et al. |
| 10,549,072 B2 | 2/2020 | Burkolz et al. |
| 10,646,253 B2 | 5/2020 | Blanc |
| 2001/0053895 A1 | 12/2001 | Vaillancourt |
| 2002/0128604 A1 | 9/2002 | Nakajima |
| 2004/0210194 A1 | 10/2004 | Bonnette et al. |
| 2005/0256500 A1 | 11/2005 | Fujii |
| 2006/0118749 A1 | 6/2006 | Ryan et al. |
| 2006/0155245 A1 | 7/2006 | Woehr |
| 2007/0083162 A1 | 4/2007 | O'Reagan et al. |
| 2007/0225647 A1 | 9/2007 | Luther et al. |
| 2007/0233007 A1 | 10/2007 | Adams |
| 2008/0058720 A1 | 3/2008 | Spohn et al. |
| 2008/0108944 A1 | 5/2008 | Woehr et al. |
| 2008/0108976 A1 | 5/2008 | Johnson et al. |
| 2009/0221975 A1 | 9/2009 | Rodd |
| 2010/0179480 A1 | 7/2010 | Sugiki et al. |
| 2010/0185153 A1 | 7/2010 | Sugiki et al. |
| 2010/0204648 A1 | 8/2010 | Stout et al. |
| 2010/0280456 A1 | 11/2010 | Nijland et al. |
| 2011/0054406 A1 | 3/2011 | McKinnon |

(56) References Cited

U.S. PATENT DOCUMENTS

| | | |
|---|---|---|
| 2011/0282286 A1 | 11/2011 | Argentine |
| 2011/0301553 A1 | 12/2011 | Goral et al. |
| 2011/0319825 A1 | 12/2011 | Goral et al. |
| 2011/0319838 A1 | 12/2011 | Goral et al. |
| 2012/0016266 A1 | 1/2012 | Burkholz |
| 2012/0089101 A1 | 4/2012 | Carlyon et al. |
| 2012/0259293 A1 | 10/2012 | Bialecki et al. |
| 2012/0330238 A1 | 12/2012 | Robert et al. |
| 2013/0006223 A1 | 1/2013 | Michels et al. |
| 2013/0165868 A1 | 6/2013 | Isaacson et al. |
| 2013/0204226 A1 | 8/2013 | Keyser |
| 2013/0304026 A1 | 11/2013 | Luther et al. |
| 2014/0052065 A1 | 2/2014 | Woehr et al. |
| 2014/0107619 A1 | 4/2014 | Butts et al. |
| 2014/0135702 A1 | 5/2014 | Woehr et al. |
| 2014/0228775 A1 | 8/2014 | Burkholz et al. |
| 2014/0276434 A1* | 9/2014 | Woehr ............... A61M 39/0693 604/164.08 |
| 2014/0276453 A1 | 9/2014 | Woehr |
| 2014/0276462 A1 | 9/2014 | Vincent et al. |
| 2014/0288500 A1 | 9/2014 | Leinsing et al. |
| 2015/0038909 A1 | 2/2015 | Christensen et al. |
| 2015/0038910 A1 | 2/2015 | Harding et al. |
| 2015/0088095 A1 | 3/2015 | Luther et al. |
| 2015/0151085 A1 | 6/2015 | Tan et al. |
| 2015/0151088 A1 | 6/2015 | Lim et al. |
| 2015/0190570 A1* | 7/2015 | Teoh ..................... A61M 5/158 604/272 |
| 2015/0335858 A1 | 11/2015 | Woehr et al. |
| 2015/0335864 A1 | 11/2015 | Knutsson |
| 2016/0008580 A1 | 1/2016 | Woehr et al. |
| 2016/0114136 A1 | 4/2016 | Woehr |
| 2016/0114137 A1 | 4/2016 | Woehr et al. |
| 2016/0296724 A1 | 10/2016 | Goral et al. |
| 2017/0035992 A1 | 2/2017 | Harding et al. |
| 2017/0173304 A1 | 6/2017 | Teoh |
| 2017/0326341 A1 | 11/2017 | Liska |
| 2018/0093077 A1 | 4/2018 | Harding et al. |
| 2018/0361119 A1 | 12/2018 | Goral et al. |
| 2018/0361120 A1 | 12/2018 | Goral et al. |
| 2019/0038870 A1 | 2/2019 | Isaacson et al. |
| 2019/0076625 A1 | 3/2019 | White et al. |
| 2019/0160264 A1 | 5/2019 | Isaacson |

FOREIGN PATENT DOCUMENTS

| | | |
|---|---|---|
| CN | 203724591 U | 7/2014 |
| CN | 203763665 U | 8/2014 |
| CN | 104039384 A | 9/2014 |
| CN | 104043167 A | 9/2014 |
| CN | 104415446 A | 3/2015 |
| CN | 105407959 A | 3/2016 |
| EP | 0875262 A2 | 11/1998 |
| EP | 1911485 A1 | 4/2008 |
| EP | 2213328 A1 | 8/2010 |
| EP | 3097939 A1 | 11/2016 |
| EP | 3337549 B1 | 6/2019 |
| FR | 2829396 A1 | 3/2003 |
| JP | H05-028348 U | 4/1993 |
| JP | H06-304250 A | 11/1994 |
| JP | H7-136285 A | 5/1995 |
| JP | H11-004894 A | 1/1999 |
| JP | H11-299898 A | 11/1999 |
| JP | 2005-531377 A | 10/2005 |
| JP | 2010-508905 A1 | 3/2010 |
| JP | 2012-525877 A | 10/2012 |
| JP | 2013-533023 A | 8/2013 |
| JP | 2014-528807 A | 10/2014 |
| JP | 2016-509916 A | 4/2016 |
| RU | 2009120995 A | 12/2010 |
| RU | 2477639 C2 | 3/2013 |
| WO | WO 2010/093791 A1 | 8/2010 |
| WO | WO 2009/041522 A1 | 1/2011 |
| WO | WO 2009/041523 A1 | 1/2011 |
| WO | WO 2013/052668 A1 | 4/2013 |
| WO | WO 2014/140265 A1 | 9/2014 |
| WO | WO 2015/104336 A1 | 7/2015 |
| WO | WO 2015/161294 A1 | 10/2015 |
| WO | WO 2018/033626 A1 | 2/2018 |
| WO | WO 2018/077748 A1 | 5/2018 |

OTHER PUBLICATIONS

International Search Report & Written Opinion on related PCT application (PCT/EP2016/069643) from International Searching Authority (EPO) dated Nov. 16, 2016.

International Search Report & Written Opinion on related PCT application (PCT/EP2014/055089) from International Searching Authority (EPO) dated Jul. 17, 2014.

International Search Report & Written Opinion on related PCT application (PCT/EP2017/070934) from International Searching Authority (EPO) dated Oct. 25, 2017.

Non-Final Office Action on related US application (U.S. Appl. No. 14/012,568) dated Aug. 8, 2014.

Final Office Action on related US application (U.S. Appl. No. 14/012,568) dated Dec. 2, 2014.

Non-Final Office Action on related US application (U.S. Appl. No. 14/818,687) dated Feb. 10, 2016.

Office Action on corresponding foreign application (JP Application No. 2018-508169) from the Japanese Patent Office dated Oct. 1, 2019.

Decision to Grant on corresponding foreign application (RU Application No. 2018109391/14) from the Russian Patent Office dated Oct. 14, 2019.

International Preliminary Report on Patentability (Chapter I) on related PCT application (PCT/EP2017/070934) from International Searching Authority (EPO) dated Feb. 28, 2019.

International Preliminary Report on Patentability on corresponding PCT application (PCT/EP 2016/069619) from International Searching Authority (EPO) dated Mar. 1, 2018.

International Preliminary Report on Patentability on related PCT application (PCT/EP2016/069643) from International Searching Authority (EPO) dated Mar. 1, 2018.

Extended European Search Report from the European Patent Office on related EP application (EP19177030.4) dated Jun. 24, 2019.

Office Action including Search Report on corresponding foreign application (CN Application No. 201680048610.6) from the National Intellectual Property Administration, P.R. China dated Mar. 27, 2020.

Office Action including Search Report on corresponding foreign application (CN Application No. 201680048615.9) from the National Intellectual Property Administration, P.R. China dated Mar. 30, 2020.

Examination Report on corresponding foreign application (AU Application No. 2016309744) from the IP Australia dated May 6, 2020.

Preliminary Office Action on corresponding foreign application (BR Application No. 11 2018 002976-9) from the Brazilian Intellectual Property Office dated May 6, 2020.

Office Action on related foreign application (MX Application No. MX/a/2018/001987) from the Mexican Patent Office dated Jul. 23, 2020.

Office Action on related foreign application (JP Application No. 2018-508170) from the Japanese Patent Office dated Jun. 23, 2020.

Office Action on related foreign application (JP Application No. 2018-508169) from the Japanese Patent Office dated Aug. 4, 2020.

Office Action on related foreign application (AU Application No. 2016309744) from the Australian Patent Office dated Aug. 31, 2020.

Office Action on related foreign application (MX Application No. MX/a/2018/001987) from the Mexican Institute of Industrial Property (IMPI) dated Dec. 8, 2020.

Office Action on related foreign application (CN Application No. 201780064583.6) from the National Intellectual Property Administration, P.R. China dated Jan. 27, 2021.

(56) References Cited

OTHER PUBLICATIONS

Office Action on related foreign application (CN Application No. 201680048610.6) from the National Intellectual Property Administration, P.R. China dated Feb. 20, 2021.
Office Action on related foreign application (JP Application No. 2018-508170) from the Japan Patent Office dated Mar. 2, 2021.
Preliminary Office Action on related foreign application (BR Application No. 12 2019 017170-0) from the Brazilian Patent Office dated Apr. 7, 2021.
Office Action on related foreign application (CN Application No. 201680048615.9) from the National Intellectual Property Administration, P.R. China dated Mar. 9, 2021.
Extended European Search Report from European Patent Office on related EP application (EP 20172492.9) dated Nov. 5, 2020.
Office Action on related foreign application (CN Application No. 201310650219.1) from the Chinese Intellectual Property Office dated Feb. 13, 2018.
Office Action on related foreign application (CN Application No. 201310650219.1) from the Chinese Intellectual Property Office dated Oct. 24, 2018.
Office Action on related foreign application (JP Application No. 2015-562191) from the Japanese Patent Office dated Apr. 25, 2017.
Office Action on related foreign application (JP Application No. 2015-562191) from the Japanese Patent Office dated Oct. 17, 2017.
International Preliminary Report on Patentability on corresponding PCT application (PCT/EP2014/055089) from International Searching Authority (EPO) dated Apr. 10, 2015.
International Search Report and Written Opinion on corresponding PCT application (PCT/EP2019/085732) from International Searching Authority (EPO) dated Apr. 28, 2020.
Supplementary Examination Report on related foreign application (SG Application No. 11201506983W) from the Singaporean Intellectual Property Office dated Jan. 29, 2016.
First Examination Report on related foreign application (IN Application No. 201817000337) from the Indian Patent Office dated May 18, 2021.
Office Action on related foreign application (JP Application No. 2019-508949) from the Japan Patent Office dated May 11, 2021.
Substantive Examination Adverse Report on related foreign application (MY Application No. PI 2018700453) from the Malaysian Patent Office dated May 12, 2021.
Non-Final Office Action on related U.S. application (U.S. Appl. No. 16/323,379) dated May 17, 2021.

* cited by examiner

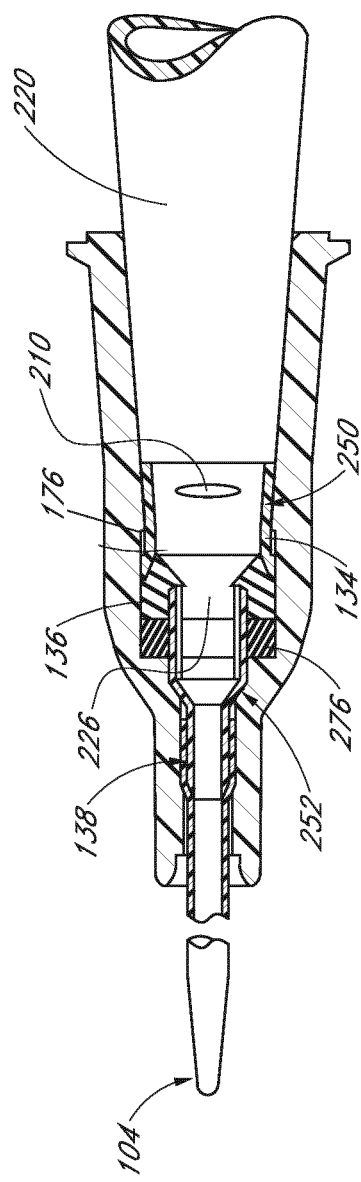
FIG. 4
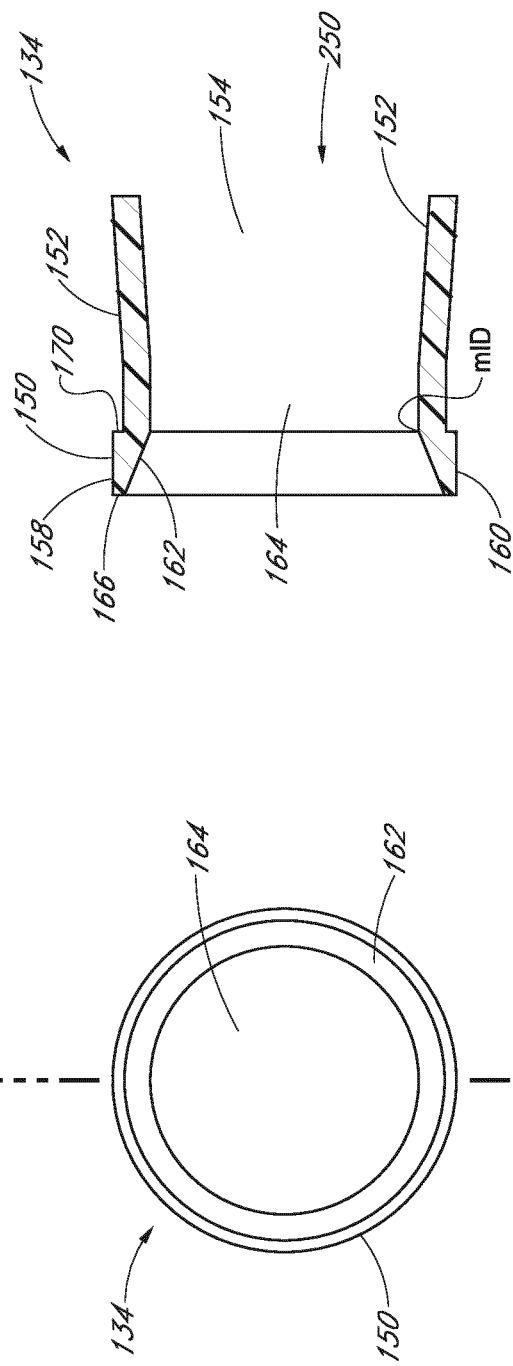
FIG. 5A
FIG. 5B

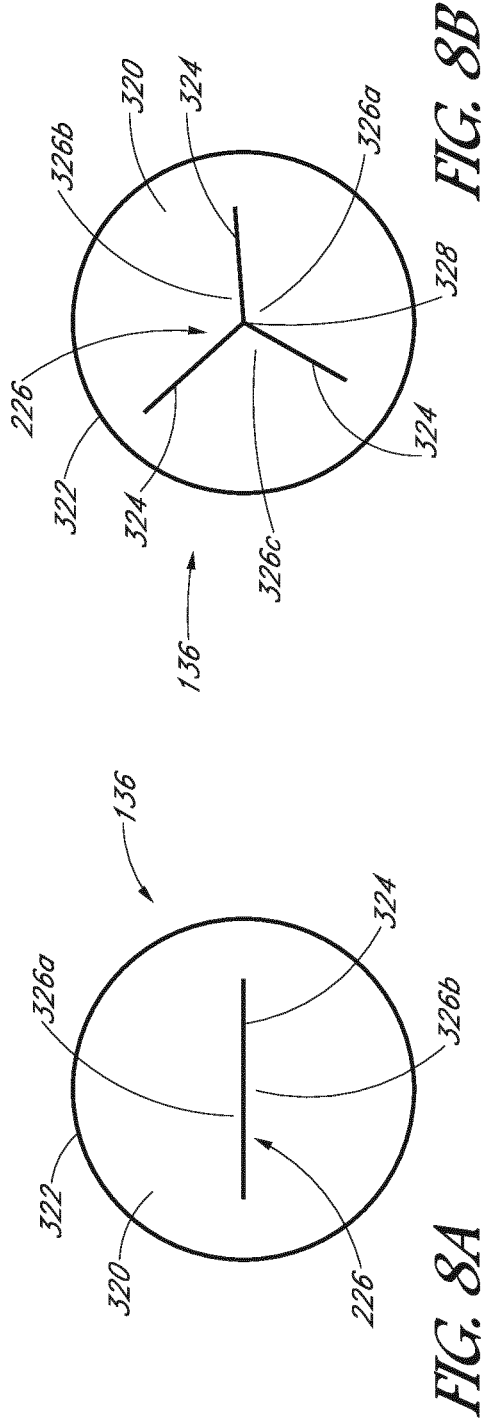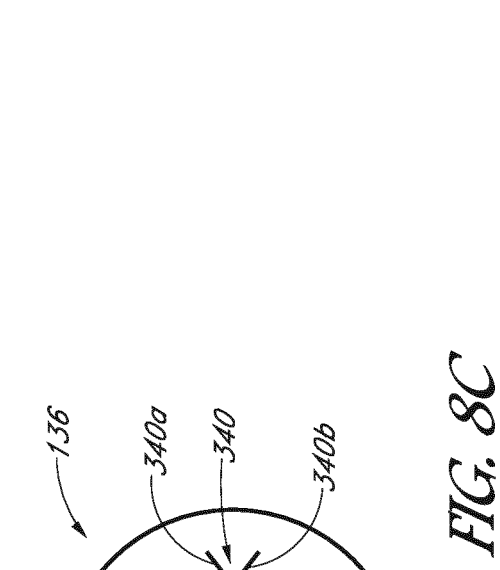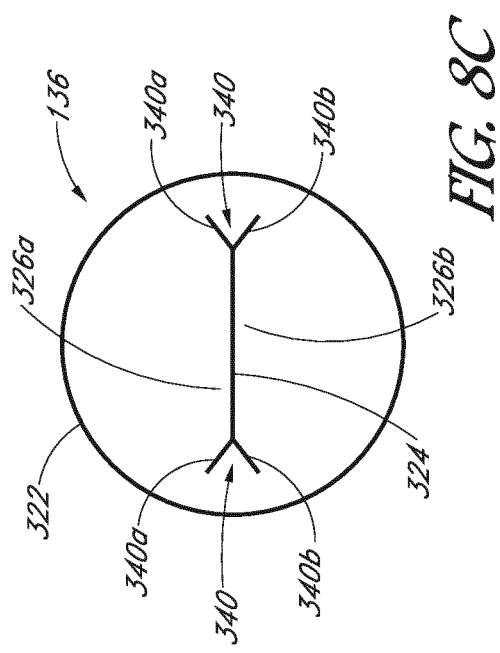

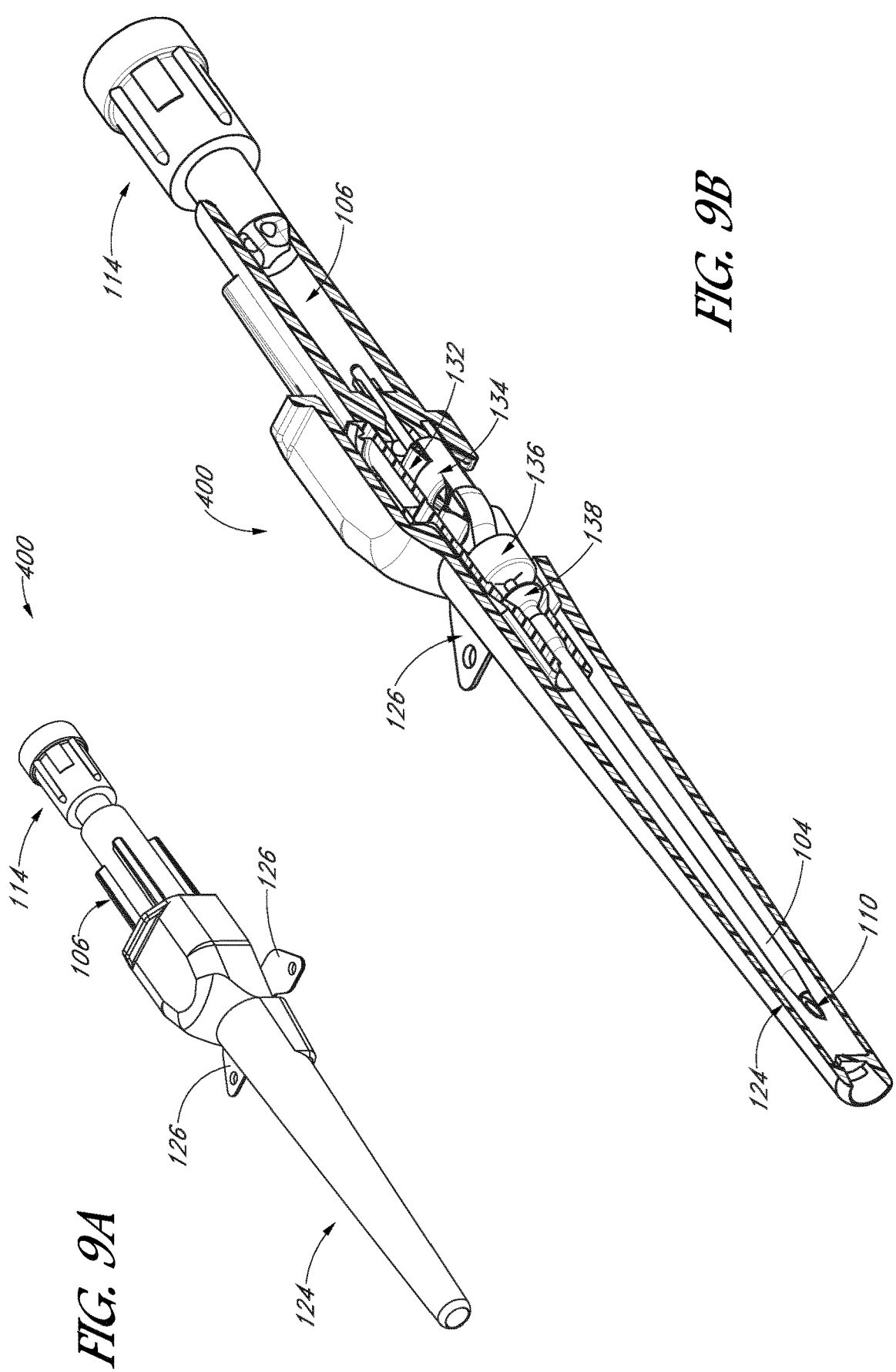

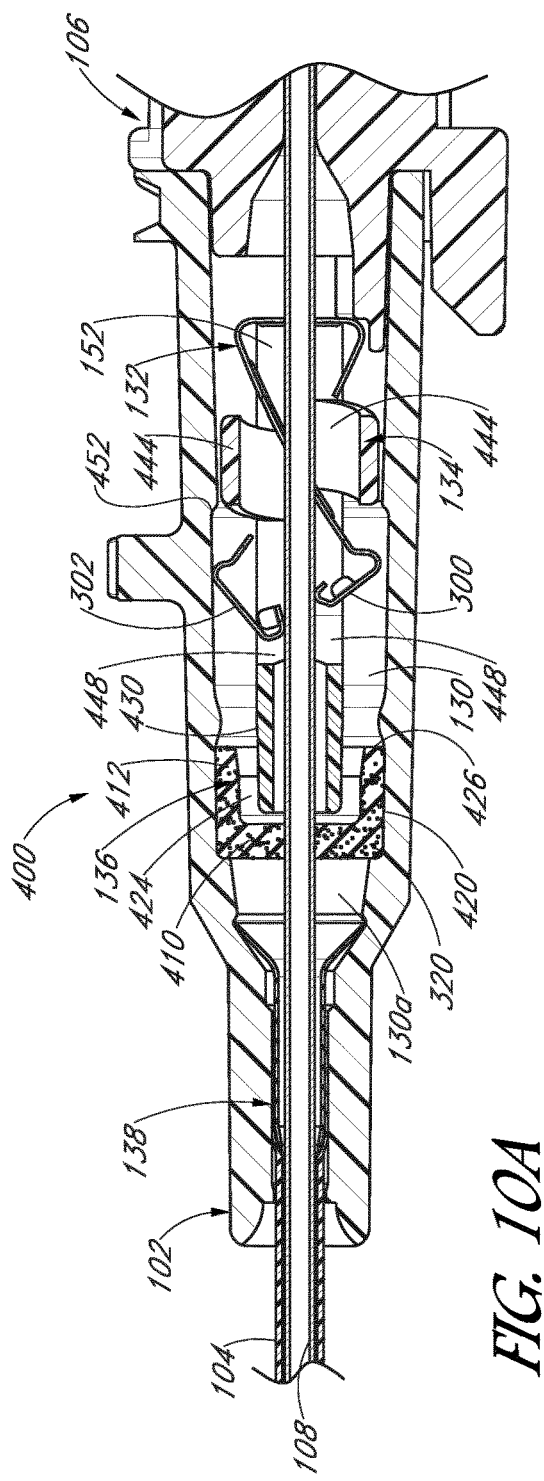
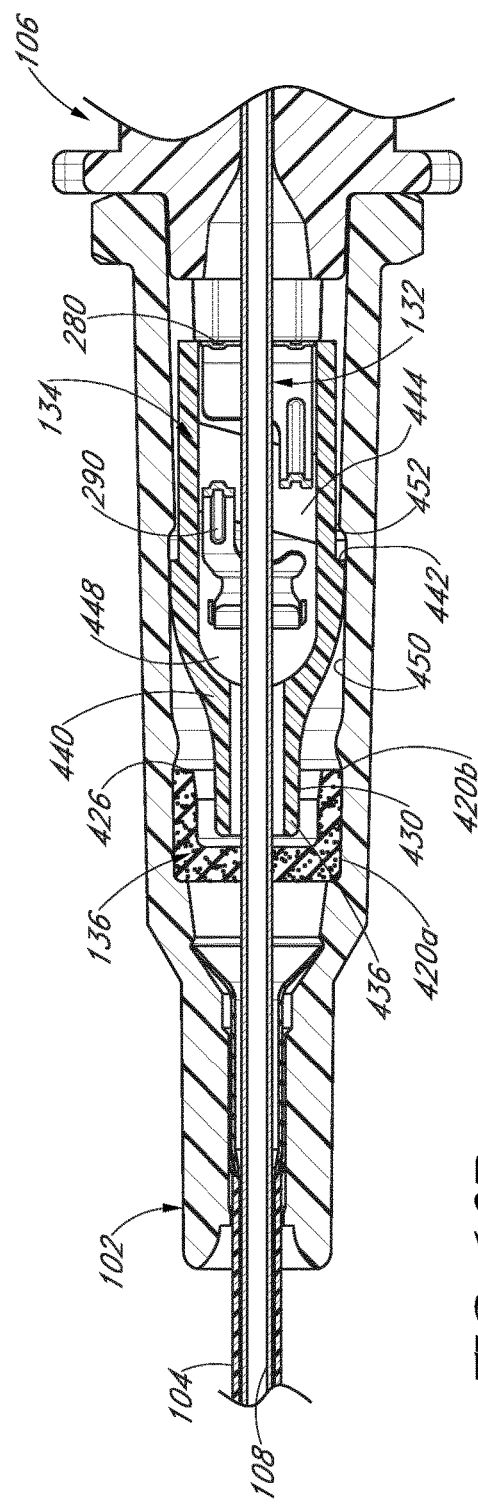
FIG. 10A
FIG. 10B

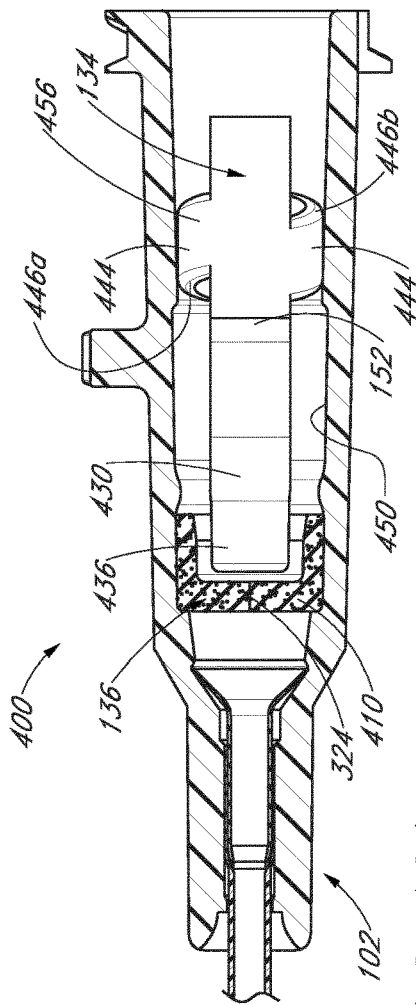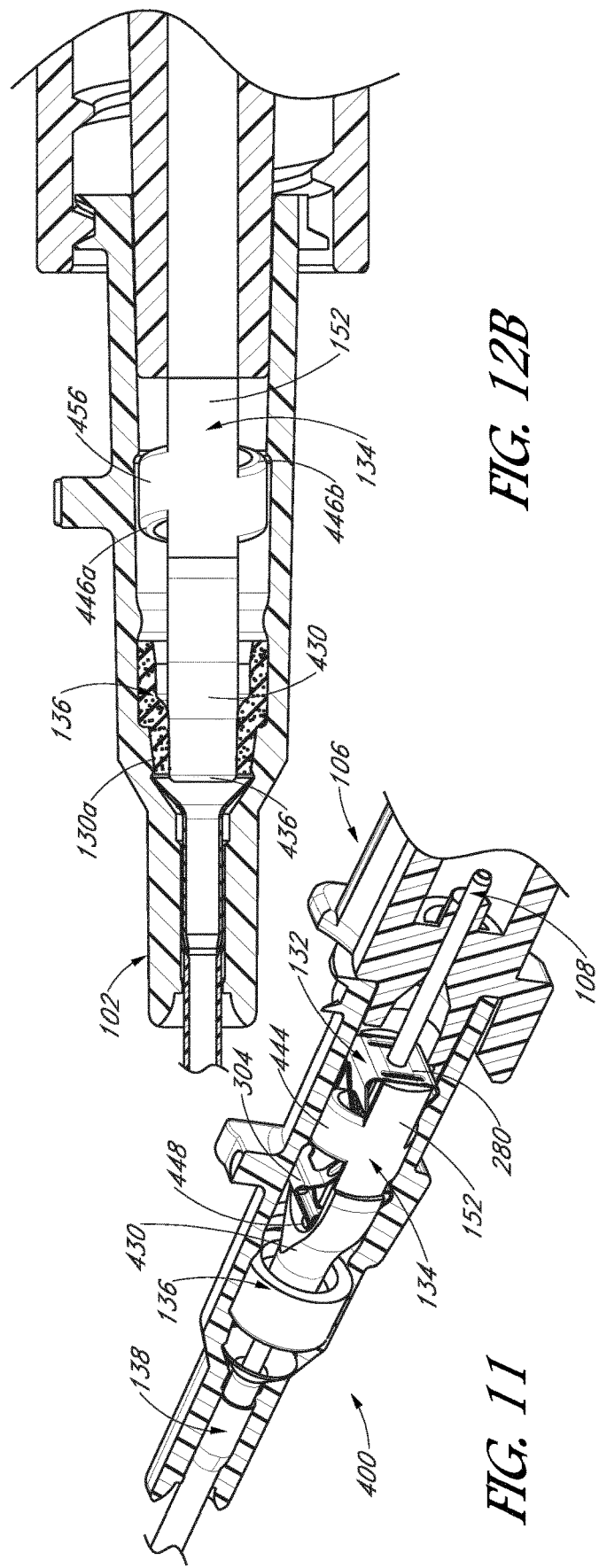
FIG. 12A
FIG. 12B
FIG. 11

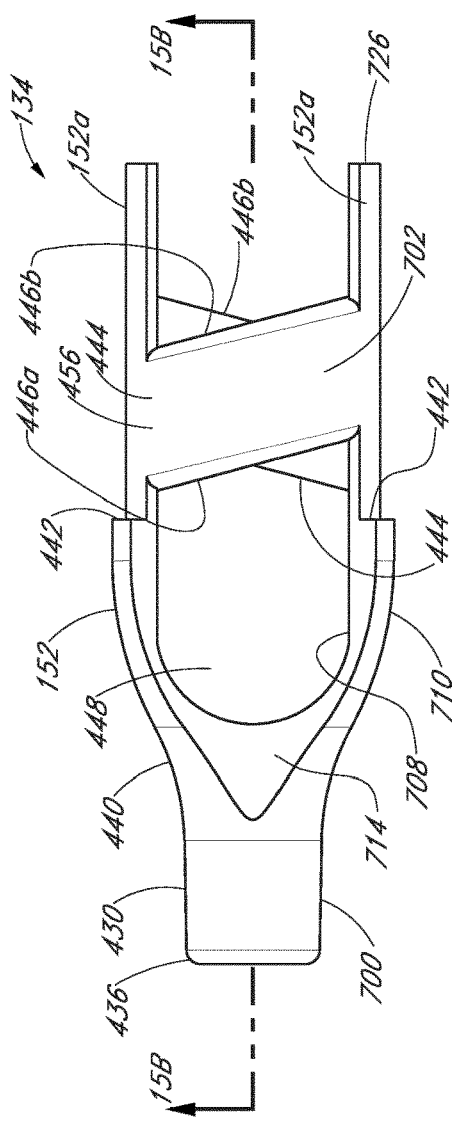
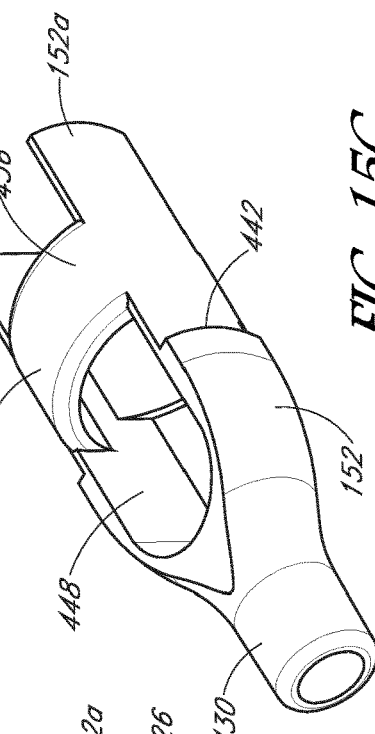
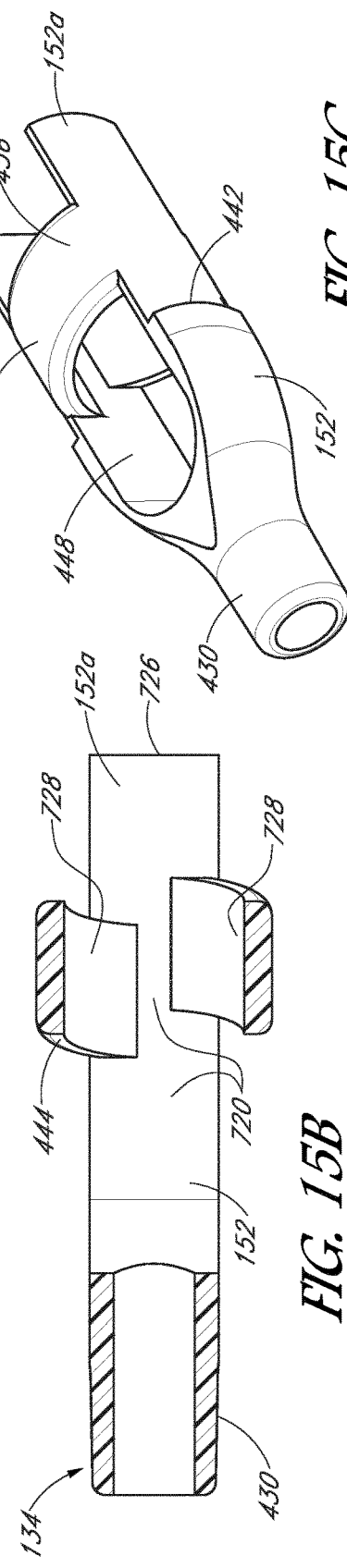
FIG. 15A
FIG. 15C
FIG. 15B

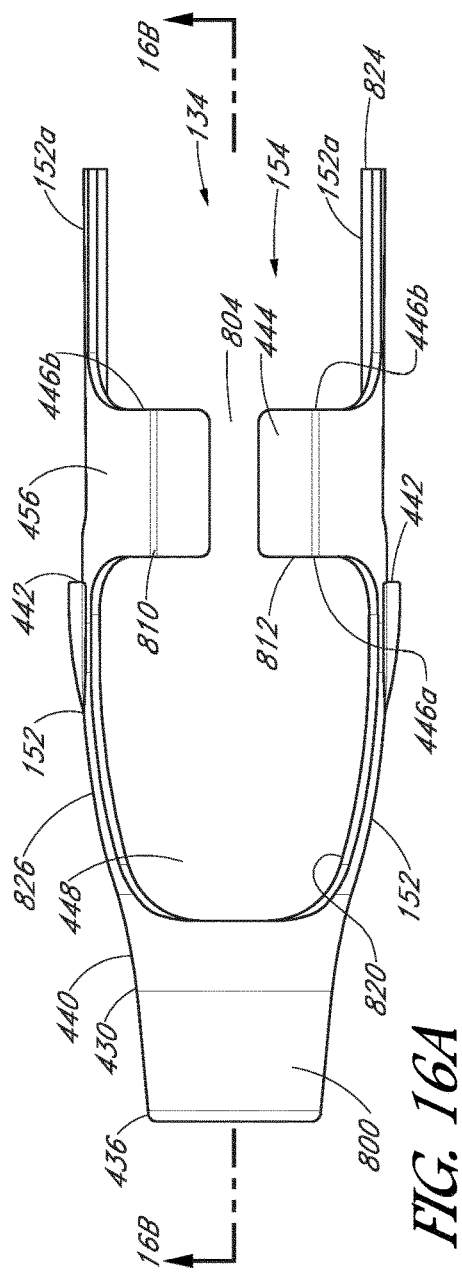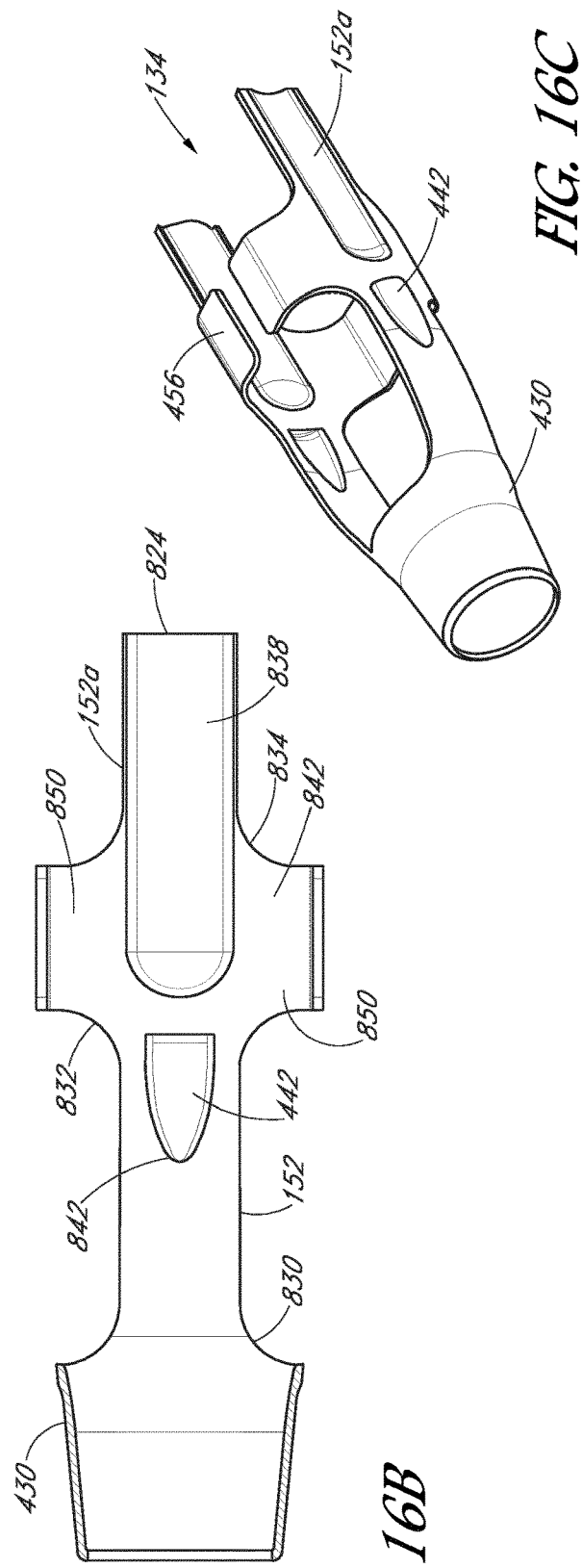

CATHETER DEVICES WITH VALVES AND RELATED METHODS

FIELD OF ART

The disclosed invention generally relates to needle devices, arterial catheters and intravenous (IV) infusion devices, including IV catheters. In particular, IV catheter assemblies having a valve and a valve actuator for opening the valve are disclosed.

BACKGROUND

IV catheters are commonly used for a variety of infusion therapies, including infusing fluids into a patient, withdrawing blood from a patient, or monitoring various parameters of the patient's vascular system. Catheters are typically connected to a catheter adapter that accommodates the attachment of IV tubing to the catheter. Blood control catheters include an internal blood control valve that is opened by the insertion of a male Luer or other object into a proximal end of the catheter adapter. Non-limiting examples of blood control valves are disclosed in United States Patent Application Publication No. 2011/0046570, filed Aug. 20, 2009, titled "Systems and Methods for Providing a Flushable Catheter Assembly." Following placement of the catheter into the vasculature of a patient, an IV fluid source can be connected to the catheter adapter or catheter hub, opening the blood control valve. Thus connected, fluid from the IV source can begin flow into a patient through the catheter.

As is well known in the art, typical blood pressure is 10 to 20 centimeters of water. Infusion bags are usually placed about 100 cm above the patient's heart to direct flow into the patient. At roughly that height, the pressure exerted by the fluid from the infusion bag is much greater than the blood pressure of the patient and therefore can flow into the patient.

Some catheter adapters permit verification of proper placement of the catheter in the blood vessel before fluid infusion begins, such as by providing a flashback chamber of the catheter assembly where a "flashback" of blood can be observed. To confirm flashback in catheter assemblies that do not include a blood control valve, a clinician must manually occlude the vein to prevent undesirable exposure to blood. In contrast, blood control valves can eliminate the need for such manual occlusion, while also reducing the likelihood of blood exposure during catheter placement.

SUMMARY

An aspect of the present disclosure can include the provision for a compact design for a valve housing of a Luer activated valve.

Another aspect of the present disclosure can include the provision for a relatively strong construction for use with high pressure injection devices.

A still further aspect of the present disclosure can include the provision for improving the state of the art of blood control or closed system infusion devices including intravenous catheters.

As described, a needle assembly of the present disclosure can include a number of different components. The needle assembly can comprise a needle hub with a needle extending from a distal end of the needle hub; a catheter tube attached to a catheter hub and having the needle extending through the catheter tube in a ready to use position; a valve positioned in an interior cavity of the catheter hub, said valve comprising an outer perimeter that axially floats when moved by a proximal valve opener, which can also be positioned in the interior cavity of the catheter hub and proximal of the valve. A distal valve opener can further be provided having two or more leg extensions extending in a proximal direction of a body of a bushing. The valve can be actuated by both the proximal and distal valve openers.

The valve can have an outer perimeter that is axially fixed within the interior of the catheter hub. The valve can be opened with just a proximal valve opener. For example, the proximal valve opener can move into the valve by a male Luer tip to deflect one or more flaps on the valve.

Any part of a valve can be axially fixed by the interior surface structure of a catheter hub.

The needle assembly wherein two or more leg extensions of a distal valve opener can be axially fixed inside the interior cavity of a catheter hub.

The needle assembly wherein a valve can comprise three slits and three flaps and wherein a distal valve opener can comprise three leg extensions. The three leg extensions can have axially extending edges that are spaced from one another. The axially extending edges can be parallel to one another.

The needle assembly wherein three leg extensions can be aligned with three flaps of a valve.

The needle assembly wherein a proximal valve opener can comprise a ring or nose section and two plunger elements with a gap therebetween. The ring or nose section can comprise an activation or actuation end. A stabilizer ring can be located proximally of the nose section. The stabilizing ring can have a continuous perimeter section defining a bore.

The nose section of the valve opener can comprise a continuous perimeter section.

The valve opener can comprise one, two, or more than two reliefs or through passages.

A needle guard located within a holding space of a valve opener can extend through a relief or through passage of the valve opener to contact an interior of a catheter hub or to contact a perimeter of the relief or through passage. The needle guard can also project through one or two reliefs of a valve opener without touching the interior of the catheter hub or touch any perimeter of the valve opener.

When a needle guard is positioned within a holding space of a valve opener, the needle guard can have a proximal wall that is flush with a proximal most end of the valve opener, positioned distally of the proximal most end, or positioned proximally of the proximal most end. When so positioned, an elbow of the needle guard can project through a relief or through passage of the valve opener. If the needle guard has two elbows on two deflectable arms, both elbows can project through two reliefs of the valve opener, one elbow for each relief.

There can be two or more reliefs or through passages of a valve opener and a needle guard can extend through the two or more reliefs or through passages or contact the two or more perimeters of the two or more reliefs or through passages.

A needle guard can comprise a resilient arm located at least in part inside a holding space of a valve opener with a first through passage and a second through passage. The needle guard can comprise an elbow projecting through the first through passage, projecting through the first through passage and in contact with a section of a perimeter of the first through passage, projecting through the first through passage and in contact with the interior surface of a catheter hub, or a combination of projecting through the first through passage and in contact with the section of the perimeter of the first through passage and the interior surface of the catheter hub.

The needle assembly of the present disclosure can comprise a tip protector located at least in part in a gap of two plunger elements of a valve opener. The gap of the valve opener can define a holding space for accommodating at least part of a needle guard or tip protector.

A tip protector can be optionally and the needle assembly can be practiced without the tip protector.

A tip protector can be unitarily formed or formed by integrating multiple pieces or components together. The tip protector can have one arm or two arms. The two arms can extend on different sides of a needle or can cross one another, such as intersect one another when viewing from a side.

The needle assembly wherein sections of a valve can be deflectable in a distal direction and sections of the valve can be deflectable in a proximal direction to open a fluid flow path through the valve.

The needle assembly wherein the sections of the valve that can be deflected in the distal direction can comprise outer edges of the valve and sections of the valve that can be deflected in a proximal direction can be flaps formed with the valve. The flaps can be formed on a valve disc. The flaps can be formed by incorporating one or more slits.

The needle assembly wherein the body of the bushing and one or more leg extensions can be integral. In some examples, the body of the bushing, such as the base or funnel section of the bushing, can be unitarily formed with one or more leg extensions. Each leg extension can have a nose section. In some examples, one leg extension is incorporated, which can have a wall defining a bore.

In an example, only part of a tip protector or needle guard can extend into one or more gaps of a valve opener while a proximal section of the tip protector can extend proximally of the proximal most surfaces of the tip protector. For example, part of the needle guard can overlap with the valve opener along an axial direction while a proximal section of the tip protector, such as the proximal wall, extends proximally or be located proximally of the proximal most surfaces of the valve opener.

In an example, only part of a tip protector or needle guard can extend distally of a stabilizing ring of a valve opener and while a proximal section of the tip protector can extend proximally of the stabilizing ring. The part of the tip protector that is located distally of the stabilizing ring can comprise one or two elbows. The one or two elbows can project through one or two reliefs in the valve opener.

A still further aspect of the present disclosure can include a method of manufacturing a needle assembly, such as a catheter assembly. The method can comprise: providing a catheter hub with a catheter tube with a distal opening, said catheter hub comprising a hub body defining an interior cavity and a proximal opening; positioning a bushing inside the catheter hub and against the catheter tube and positioning a valve proximal of the bushing; the valve being floatable inside the interior cavity of the catheter hub along an axial direction of the catheter hub and comprises two or more flaps; positioning a proximal valve opener proximal of the valve and inside the interior cavity of the catheter hub; placing a needle, which is attached to a needle hub, through the catheter hub, the valve, and the catheter tube so that a tip of the needle extends out the distal opening of the catheter tube; and wherein two or more leg extensions extend in a proximal direction of a body of the bushing.

The method wherein the two or more leg extensions of a distal valve opener can be aligned with the two or more flaps on the valve. Optionally, a single leg extension can abut a valve disc from a distal side of the valve disc.

The method wherein a proximal valve opener can comprise a ring or nose section and at least one plunger element. A stabilizing ring can be located proximally of the at least one plunger element. In some examples, there can be two or more plunger elements and the stabilizing ring is located proximally of the two or more plunger elements.

A nose section or ring of a valve opener can comprise an activation or actuation end. The nose section can define a bore. Fluid can flow through the bore. A needle can pass through the bore of the nose section in a ready to use position.

The method wherein a proximal valve opener can comprise two spaced apart plunger elements having a gap therebetween. The gap can define a holding space.

The method wherein a needle guard can be located at least in part in the gap and between the two plunger elements.

The method wherein two or more leg extensions of a distal valve opener can be fixed along an axial direction.

The method wherein a proximal valve opener can be slidable in a distal direction to move a valve having two or more flaps in a distal direction against one or more leg extensions. The valve can have three slits and three flaps. The three slits can converge at a single point. The valve can have a valve skirt extending proximally of a valve disc.

The valve skirt of a valve can define a valve cavity. The valve cavity can accommodate at least part of a proximal valve opener in a ready to use position. A nose section of a proximal valve opener can be located in the valve cavity.

Infusion or injection hypodermic needles described herein may utilize a valve in a housing having a female Luer connector. For example, the valve and valve opener of the present disclosure may be placed inside a needle hub. Also, a needleless valve integrated in a medical device or a standalone needleless valve can utilize the valve described herein.

A needle assembly or a needle device of the present disclosure can include a catheter hub with a catheter tube attached to the hub body and a needle hub with a needle extending through the catheter hub and the catheter tube with the needle tip extending out a distal end or distal opening of the catheter tube in a ready to use position.

Various components described herein can be located in an interior cavity of a catheter hub.

In the ready position, the catheter assembly is ready for use, such as to perform a venipuncture or intravenous access. Sometimes the ready position first requires removing a protective cap from the catheter assembly or needle assembly. The protective cap can be included for packaging.

A valve and a valve actuator for use with a catheter hub of the present disclosure can also be placed within the needle hub as a second valve.

A needle guard or tip protector, a valve opener or actuator, a valve, and a bushing can be provided with the catheter hub.

Optionally, a needle guard or tip protector comprising a resilient portion can be located outside of a catheter hub, such as in a separate hub different from the catheter hub and needle hub.

A tip protector of the present disclosure may embody any number of prior art guards configured for blocking or covering the needle tip of the needle.

A tip protector can have a proximal wall and two resilient arms and wherein a change in profile on the needle, such as a crimp or a bulge, can engages a perimeter defining an opening on the proximal wall of the tip protector to retract the tip protector in the proximal direction out of the catheter hub following successful venipuncture. The two arms can intersect or they can run along different sides of the needle and do not intersect along a side view.

When two arms on a needle guard move radially due to axial movement of a needle, a radial profile, such as shape or dimension, of the needle guard can change. For example, the radial profile of the needle guard can decrease when the tip of the needle move proximally of two walls to permit the two arms to move in a radial direction.

The needle guard arm or arms can be spread by the needle shaft in a ready position and engage the inside of the catheter hub, such as the guard engagement section the catheter hub. The needle guard can be rolled or bent to final configuration from a stamped metal sheet. Alternatively, the needle guard can be formed from different components, from all metal components, from plastic components, or combinations thereof, that are then assembled to form a needle guard.

A valve opener or actuator can comprise a ring or a nose section and at least one plunger element, such as a leg element or an elongated extension. The ring can be in contact with the valve in the needle assembly ready to use position. Optionally, the ring can be spaced or slightly spaced form the proximal surface of the valve in the ready to use position.

One or more plunger elements can extend from the ring or nose section in the proximal direction. In other examples, there can be more than two plunger elements, such as three or more plunger elements having gaps therebetween. The one or more plunger elements can each be sized and shaped for contact by a male Luer to transfer a distally directed force from the male Luer to the ring or nose section of the valve opener to then push against a proximally facing surface of the valve to open the valve, such as to open two or more flaps.

The one or more plunger elements of a valve opener can each have an arc shape or arc cross section along a width. In another example, a plunger element can be generally flat or planar along a cross section. The thickness of a plunger element should be sufficiently small or thin so that a needle guard and two plunger elements have sufficient clearance to fit within the interior cross-sectional space of a catheter hub without being physically binding against the interior of the catheter hub and rendered unmovable or fixed.

In an example, the thickness of a plunger element of a valve opener or actuator and a width of a needle guard are such that no undercut or channel is required to be formed in the interior wall surfaces of the catheter hub to accommodate them.

A valve opener of the present disclosure can be made from a metal material, from a plastic material, or from both. When made from a metal material, the valve opener can be formed by deep draw methods and the arc shape cross section of the plunger element can provide added rigidity when pushed by the male Luer.

Each plunger element of a valve opener can comprise at least two lengthwise edges and a rib can be provided along one or both of the lengthwise edges to further add structural rigidity. One or more gaps can be provided between any two plunger elements. The gaps can provide clearance or space for fluid flow flowing thereacross, such as during IV infusion. The gap can also be utilized to accommodate a needle guard, such as to act as a holding space.

The ring or nose section of a valve opener can comprises a body with an outer perimeter. The outer perimeter can be generally cylindrical. The outer perimeter can have a taper. The body can comprise a chamfer and an opening.

The distal edge or intersection of the body between the chamfer and the outer perimeter can have a sharp edge or a blunt edge. In an example, the intersection is a blunt edge comprising a planar surface that functions as an actuation end for pushing against the valve.

The valve opener of the present embodiment can be configured to push against a proximally facing surface of a valve or a multi-part opener for pushing against both a proximally facing surface of a valve and a distally facing surface of a valve. The valve can have two or more flaps that can deflect radially and proximally or radially and distally when activated.

On the proximal side of a ring or nose section, two plunger elements can be recessed radially inwardly from an outer perimeter to form or define a shoulder. The outer perimeter of the ring can have an outside diameter of a first dimension and the two plunger elements can define an outside diameter of a second dimension, which can be smaller than the first dimension. A shoulder can be provided between the two different dimensions.

A valve opener can have an inside diameter measured adjacent the intersection or activation end. The inside diameter can change or vary along a chamfer section of the ring or nose section. The valve opener can further include a minimum inside diameter mID, which can be viewed as the smallest inside diameter of the valve opener.

A needle guard can be located between one or more gaps defined by plunger elements of a valve opener. The plunger elements can each comprise an arc-shape cross section. The arc-shape cross section of each plunger element can be generally C-shaped with the concave portion facing internally towards the needle guard and the convex portion facing outwardly away from the needle guard.

The radius of curvature of two C-shaped plunger elements of a valve opener can be different than the radius of a male Luer tip and/or the radius of the interior cavity of the catheter hub. A gap can be provided on each side edge of the proximal wall of the needle guard and the adjacent plunger element.

Two plunger elements of a valve opener can each have an abutting proximal surface that is sized and shaped to be pushed against by a male Luer tip or a syringe tip when said tip is inserted into the proximal opening of the catheter hub following successful venipuncture to push the valve opener distally against a valve to open the valve. The arc-shape cross section of each of the two plunger elements can provide a sufficiently thick profile to ensure overlapping abutting surfaces with the male Luer tip and rigidity from buckling.

The C-shaped plunger elements can avoid deflection when pushed by a syringe tip or other male Luer tip, avoid slippage of the syringe tip or Luer tip missing the end surfaces of the plunger elements when the syringe tip or Luer tip is inserted into the open proximal end of the catheter hub, and/or avoid a situation in which the syringe tip or Luer tip is pushed between the two plunger elements to wedge the two plunger elements between the tip and the interior surface of the catheter hub during activation of the valve opener.

In some embodiments, the concave portion of the arc-shape cross-section of each plunger element can face outwardly, away from the needle guard, while the convex portion of each plunger element faces inwardly towards the needle guard.

The ring or nose section of a valve opener can be elastically deformed and then expand when it reaches a recessed hub section of the catheter hub, which can accommodate the ring without deforming the ring. Alternatively, the catheter hub can be designed to expand to allow the assembly of the valve opener. A shoulder can be provided at the recessed hub section, which can form a physical stop for engaging a shoulder on the valve opener. This can allow the valve opener to be retained within the interior cavity of the catheter hub during needle withdrawal and during use, when the valve opener is pushed distally to activate the valve and subsequently moves proximally when the male Luer is removed, thus allowing the valve to close.

A valve can have a valve disc comprising a valve body comprising a valve diameter, a valve thickness measured orthogonal to the valve diameter, such as between a proximally facing surface and a distally facing surface of the valve disc, and one or more slits defining two or more flaps on the valve disc. Three slits can be provided through the valve thickness to define three flaps. The three slits can originate from a point and extend radially from about a center point or central portion of the body of the valve, similar to a three-point star, to form three flaps that can deflect along the slits.

The valve can comprise an outer perimeter that can float inside the interior cavity of the catheter hub, between a proximal valve opener and a bushing. The outer perimeter of the valve can move proximally and distally within the interior cavity of the catheter hub and not be restrained by the catheter hub along an axial direction of the catheter assembly. In some examples, the valve can be axially fixed for pushing thereagainst by a proximal valve opener.

The outer perimeter of the valve can be the same or smaller or larger than the outer perimeter of a ring or nose section of a valve opener. At least some part or all of the distal edge, intersection, or activation end of the ring or nose section can be recessed from an outer radial perimeter of the valve so that the distal edge can abut or touch the proximally facing wall surface of the valve. Also, since the valve can float, the valve can be positioned inside a single hub body catheter hub and can avoid being wedged between a multi-part hub body. However, the various components described herein may readily be used with a multi-piece catheter hub without deviating from the scope of the present disclosure.

The bushing of the present disclosure can comprise a body comprising a first body section and a second body section extending from the first body section. The second body section can having a cone shape section and two or more leg extensions extending from the second body section, such as extending from the cone shape section.

The first body section can have an elongated body that can have a cylindrical shape with an optional tapered distal tip or nose section. In some examples, a generally cylindrical ring extends from the second body section and the two or more leg extensions extend from the cylindrical ring.

As used herein, the terms first, second, third, etc. are understood to describe different structures so as to distinguish one from another. However, the terms are not structurally limiting unless the context indicates otherwise.

One or more gaps can be provided between two adjacent leg extensions. The number of leg extensions incorporated with the bushing can be the same as the number of flaps incorporated with a valve. The leg extensions can be spaced from one another. The leg extensions can be attached to a common structure at a respective fixed end, opposite a respective free end.

The leg extensions on a bushing or the leg extensions of a distal valve opener can define an outside diameter that is smaller than the minimum inside diameter mID of a ring of valve opener. The proximal tip of each leg extension can have a chamfer or a blunt tip at a proximal end or proximal tip. In one example, a chamfer can be incorporated at the proximal tip of each leg extension and wherein the chamfer can taper inwardly from the exterior of the leg extension.

The bushing can be made from a metal material and the leg extensions can be unitarily formed with the body. Alternatively, the leg extensions can be welded to the body of the bushing.

The bushing and the valve can be oriented in the catheter hub so that the leg extensions on the bushing are aligned with the flaps on the valve. This can allow the flaps on the valve to be pushed by the leg extensions on the bushing. Thus, if there are three flaps on the valve, the three flaps can be pushed into physical contact with three leg extensions on a distal valve opener.

A distally facing wall surface of a valve can touch a leg extension of a distal valve opener and/or a resilient element, such as a spring or an elastic element, or be spaced from the leg extension and/or the resilient element so as to move the valve in a proximal direction.

A distally facing wall surface of a valve can be pushed distally against a leg extension during use. In some examples, the valve can touch a proximal tip of a leg extension and/or a resilient element in the valve closed position or be spaced therefrom.

Three leg extensions of a valve opener can be equally spaced along a circumference of a second body section of a bushing. In another example, three leg extensions can be located and spaced in accordance with the positions of the lugs or flaps on a valve so that when assembled inside a catheter hub, the valve can be pushed distally by a proximal valve opener or valve actuator and the leg extensions on the distal valve opener are aligned to push the lugs or flaps of the valve in the proximal direction to open the valve. The lugs or flaps can be formed by slitting the valve with slits.

During retraction of the needle in the proximal direction following successful venipuncture, the tip protector can be held axially by the engagement between one or both resilient arms on the tip protector and a guard engagement section on the catheter hub.

The guard engagement section can be a surface discontinuity formed on the interior surface of the catheter hub. For example, the guard engagement section can comprise a section of a first inside diameter and a section of a second inside diameter, which is larger than the first inside diameter. The guard engagement section can be annular or circular in shape or can be less than a full circle.

The guard engagement section can embody an internal projection or a groove or a combination of both a groove and a projection formed on the interior surface of the catheter hub. When a combination of a groove and a projection is used for a guard engagement section to engage a needle guard or tip protector, the groove can be distal to the projection.

Two spaced-apart guard engagement sections can be provided for engaging the two resilient arms on a tip protector. The two guard engagement sections can be located diametrically opposite of one another at a location just distal of the section of the female Luer taper of the catheter hub.

In an example, a valve opener can incorporate a single plunger element. The single plunger element can embody a generally cylindrical body section having an interior surface defining a bore having a path or channel. The cylindrical body section can be located proximally of a distal push end, which can also be annular or circular. A guard engagement section can form on the interior surface of the present valve opener. In other words, the guard engagement segment can be provided with the interior surface of the valve opener instead of the interior surface of the catheter hub. This allows the tip protector or needle guard, such as two resilient arms of the needle guard, to engage the valve opener in the ready to use position and during retraction of the needle following successful venipuncture.

The guard engagement section formed on or with the valve opener can comprise a projection, a recess, an opening, or combinations thereof.

Another aspect of the present disclosure includes a valve opener comprising a nose section with an activation end and two plunger elements extending in a proximal direction of a nose section. A band or ring can be provided connecting the two plunger elements together. The band can be called a stabilizing ring and can connect the two plunger elements together to form a stabilizing structure.

A stabilizing ring can form a continuous perimeter section of a valve actuator that is spaced from another continuous perimeter section defined by a nose section of the valve actuator.

Two stabilizers, which can also be called stabilizer elements, can connect to two plunger elements to form a stabilizing ring, which can have a continuous perimeter section.

A valve actuator can have a first continuous perimeter section, a section with one or more reliefs, and a second continuous perimeter section spaced form the first continuous perimeter section.

At the reliefs or through passages of a valve opener, the valve opener can have one plunger element with two lengthwise edges, or two plunger elements each with two lengthwise edges. In some examples, there can be three or more plunger elements each with two lengthwise edges.

A valve opener can terminate, at its proximal side or end, with a stabilizing ring. In another example, one or more plunger element stubs or extensions can extend proximally from the stabilizing ring.

The overall length of a valve opener can be adjusted by adding one or more plunger element stubs or extensions extending proximally of a stabilizing ring.

A first continuous perimeter section can be a nose section of a valve actuator. The nose section can include an activation end for pushing against a valve to open the valve. A second continuous perimeter section can be provided and be a stabilizing ring connected to one plunger element or to two or more plunger elements.

A valve opener provided herein can comprise two plunger elements each with two lengthwise edges located between a first continuous perimeter section and a second continuous perimeter section. In some examples, two plunger element stubs can extend proximally of the second continuous perimeter section.

A valve actuator or opener provided herein can include a single plunger element extending from a nose section having an activation end and wherein the single plunger element can comprise two or more reliefs or through passages formed through the wall of the plunger end. A needle guard or tip protector can engage the edges or perimeters of the reliefs in the ready to use position and during retraction of the needle following successful venipuncture.

When a tip protector engages a perimeter of a valve opener, it is understood that the tip protector can engage a section or portion of the perimeter only. For example, when an elbow of a needle guard engages a perimeter of a valve opener, the elbow can contact only a portion or a section of the perimeter. The perimeter can be for a relief or a through passage.

Still alternatively, a tip protector can project through the reliefs of a valve opener but not contact the interior of the catheter hub or the perimeters of the reliefs.

Still alternatively, a tip protector can project through the reliefs of a valve opener, contacts the interior of the catheter hub, and contacts one or both perimeters of the reliefs.

In a particular example, the part of a tip protector that projects through the reliefs can be one or two elbows of the tip protector.

Alternatively, the tip protector or needle guard can project from a holding space defined by the valve opener through the reliefs to engage the interior surface of the catheter hub. Bumps, grooves, or recesses can be provided on the interior surface of the catheter hub for the elbows of the needle guard to project through the reliefs from the holding space of the valve projector to engage.

The elbow of each arm of the needle guard may sometimes be referred to as a diagonal section.

The perimeters of two reliefs or through passages can function as guard engagement sections by allowing the elbows of the tip protector to engage thereto. Alternatively, the two elbows of the needle guard can project through the two reliefs from the holding space defined by the valve opener to engage the guard engagement sections or segments formed on the interior surface of the catheter hub. Still alternatively, one or both elbows can be restricted in a proximal direction by a choke point or choke gap.

In still other examples, at least one elbow of a needle guard or tip protector can project through a relief or through passage of a valve opener but does not engage the perimeter nor contact the interior of the catheter hub in a ready to use position. In other examples, two elbows of a needle guard project through two reliefs or through passages of a valve opener but do not engage the perimeters of the two reliefs or contact the interior of the catheter hub in a ready to use position.

In some examples, the one or two elbows of a needle guard can contact one or more perimeter of one or more reliefs and/or the interior of the catheter hub.

Where a valve opener has a single plunger element between a first continuous perimeter section and a stabilizing ring, which can include a second continuous perimeter section, one or more elbows of a needle guard can be located between the first continuous perimeter section and the stabilizing ring. If the needle guard has two elbows, both elbows can be located between the first continuous perimeter section and the second continuous perimeter section.

The second continuous perimeter section can represent a proximal most end of a valve opener. In some examples, one or two plunger element stubs or extensions can extend proximally of the second continuous perimeter section to extend a length of the valve opener beyond the proximal end of the second continuous perimeter section.

In some examples, the stabilizing ring does not form a continuous perimeter and one or two plunger element stubs or extensions can extend proximally of the non-continuous perimeter section.

The perimeters of the reliefs or the interior surfaces of a catheter hub can form anchor points for the arms of a tip protector to engage thereto in the ready to use position and during retraction of the needle following successful venipuncture.

The perimeters of the reliefs or through passages of a valve opener can present or act as restricting point, choke point, or choke gap for one or two elbows, respectively, of a needle guard. That is, a dimension of one elbow measured to a side of a needle can be larger than a dimension measured at an outer perimeter of the valve opener at the relief so that an interference is provided by the perimeter at the relief against proximal movement of the needle guard during retraction of the needle following successful venipuncture.

Once an elbow of a needle guard moves radially away from a relief, the radial profile of the needle guard can be reduced and can be smaller than the inside diameter of the valve opener at the relief. The needle guard can then move proximally of the relief or through passage, such as through a stabilizing ring in a proximal direction.

If two elbows are employed by a needle guard, a dimension defined by the two elbows can be larger than a perimeter of the valve opener at the two reliefs so that the perimeters at the two reliefs can act as or provide restricting points or choke points against proximal movement of the needle guard during retraction of the needle following successful venipuncture. Once the two elbows of the needle guard move radially away from the two reliefs of a valve opener, the needle guard can move proximally of the two reliefs or through passages, such as proximally through a bore defined by a stabilizing ring.

In an example, a valve opener can comprise a nose section and a single plunger element. The single plunger element of the valve opener can embody a generally cylindrical body section having an interior surface defining a bore having a path or channel and a proximal perimeter or end edge. A guard engagement section can be formed on the interior surface of the valve opener. In other words, the projection, bump or recess can be formed on the interior wall surface of the valve opener to allow engagement between the needle guard and the interior surface of the valve opener.

When the present alternative valve opener is used with a needle device or catheter assembly, the guard engagement segment can be on the catheter hub, on the interior wall of the valve opener, or a perimeter of a relief formed through the wall of the valve opener.

There can be one or more reliefs or guard engagement segments incorporated with the valve opener.

There can also be one or more guard engagement segments formed with the catheter hub for use with the one or more reliefs of the valve opener.

The number of guard engagement segments can equal the number of elbows formed with a needle guard.

Two resilient arms of a tip protector can engage the interior of a valve opener or engage the catheter hub by projecting through reliefs formed through the wall of the valve opener. In yet another example, two openings can be provided through the wall layer of the cylindrical body portion of the valve opener for use with the guard engagement segment formed with or on the interior of the catheter hub. The openings each can comprise a perimeter, which can be a closed perimeter.

In a ready to use position using, a valve opener with two openings or relief provided through a wall layer of the valve opener, the resilient arm or arms of a tip protector can project through the openings or reliefs to engage a guard engagement segment of the inside of the catheter hub instead of or in addition to engaging the openings of the valve opener.

The guard engagement segment can be formed on the interior surface of the catheter hub and the proximal cylindrical body section of the valve opener can comprise an opening that surrounds the guard engagement segment in at least one direction. In an example, when looking radially outwardly away from a needle, the opening on the valve opener can surround a guard engagement segment formed with a catheter hub.

During retraction of a needle following use, the needle tip can move proximally of two distal walls, one on each end of a resilient arm, of a tip protector or needle guard. The needle guard can instead have one distal wall and/or one arm. The needle guard can also have two arms but only one elbow and one distal wall.

A change in profile on a needle, which can be a crimp, a bulge, a material build up, or a sleeve, can engage a perimeter of a hole or bore through a proximal wall of the tip protector. Once engaged, the tip protector can move proximally with the needle to be removed from the catheter hub. In a protective position in which the tip protector covers or blocks the needle tip, the valve can remain inside the interior cavity of the catheter hub. Thus, the valve can be located inside the catheter hub in both the ready position of the needle and the protective position of the needle.

A male medical implement or instrument can be a male Luer, a syringe tip, an IV set connector, or other male tip having a Luer taper, of current or future ISO standards, and can be inserted into an open proximal end of a catheter hub. The male medical implement can be connected to an IV tubing, which can be connected to an IV fluid source for fluid delivery through the male medical implement. The male tip can be understood to be a male Luer tip.

When initially inserting the male medical implement or male tip into the proximal opening of the catheter hub, the male tip can initially contact the two plunger elements or two plunger element stubs on a valve opener to advance a distally directed force on the two plunger elements or two plunger element stubs to push an actuation end into a valve to open the valve. The arc cross section of the plunger elements or plunger element stubs can have a smaller diameter than the inside diameter of the catheter hub to provide a larger contact surface for the distal end of the male medical instrument.

In some examples, the male tip can abut a proximal ring and can advance the valve opener against a valve by pushing on the proximal ring, such as a stabilizing ring.

The distally directed force can move the valve opener in the distal direction until the geometries of the male tip and the proximal opening of the catheter hub stop further distal advancement of the male tip. A seal can be provided by the Luer engagement to prevent fluid from leaking out the proximal opening of the catheter hub.

The ring or nose section of a valve opener can be urged distally and pushes against a proximally facing surface of a valve. The distal edge of the valve opener can initially push against the proximally facing surface of the valve. As the valve can be axially movable inside the catheter hub, the valve can be urged distally by the valve opener, which can be urged distally by a male tip. The valve can have a valve disc. A valve skirt can extend from the valve disc, in the proximal direction, the distal direction, or both the proximal and distal directions.

Due to the presence of leg extensions on a bushing or distal valve opener, the outer edges or outer valve sections of a valve can move distally while other parts on the valve that abut or contact the leg extensions can be stopped from moving distally by the leg extensions. In effect, the valve outer edges can move distally while the flaps on the valve can deflect from a central point or location radially outwardly and in a proximal direction by the leg extensions on the bushing to open a flow path through the valve.

The chamfer on a ring or nose section and a chamfer on a leg extension can facilitate deflection of the flaps on the valve radially outwardly and in a proximal direction.

Relative diameters defined by a leg extension or a plurality of leg extensions and a minimum inside diameter mID of a ring of the valve opener can allow a proximal valve opener and a distal valve opener to deflect the valve therebetween to open the valve. Alternatively, the outer perimeter of the valve can remain in contact with the inside wall of the catheter hub, when pushed distally, with only the flaps opening around the slit or slits.

Thus, an aspect of the present disclosure is understood to include a catheter assembly comprising a valve comprising one or more slits and two or more flaps wherein the valve can comprise parts or sections that move in a distal direction and parts or sections that open along a radial direction and in a proximal direction to open a flow path through the valve.

In an example, outer edges of a valve can be configured to move distally while flaps of the valve can be configured to move radially outwards to open a flow path through the valve. Also, by incorporating a valve that can move in this fashion to open a fluid flow path, the actuation distance that the valve opener has to travel in the axial direction of the catheter assembly to open the valve can be minimized compared to a valve having flaps that only open in a distal direction by a valve opener. Thus, the size of the catheter hub, such as the length of the catheter hub, can be reduced compared to one that utilizes a valve and a valve opener that opens the valve by deflecting the valve flaps only in the distal direction. Alternatively, the length or size of the catheter hub can be minimized by overlapping portions along an axial direction between a valve opener and a needle guard.

A catheter assembly can comprise a valve and wherein a valve perimeter can float in an axial direction relative to a catheter hub is disclosed. By incorporating a valve with a valve perimeter that can float in the axial direction, a two-part catheter hub is not required to secure the valve perimeter therebetween and inside the catheter hub, although a two-part hub can be used. Therefore, a catheter hub with a singularly formed hub body may be used with the present catheter assembly. Thus, the size of the catheter hub, such as the outer diameter or dimension of the catheter hub, can be reduced compared to one that utilizes a two-part hub body. The two part hub body where they join along a seam can thus be reduced to provide a catheter assembly with a relatively smaller outer profile.

The valve opener can be configured to push the valve against another structure, such as the leg extensions on a bushing or on a distal valve opener. The present valve opener may be viewed as having a multi-piece valve opening structure. For example, the part with the ring and the plunger elements may be viewed as a proximal valve opener and the bushing with the leg extensions may be viewed as a distal valve opener. The two valve openers can cooperate to open a valve.

A proximal valve opener can be sized and shaped to push against the outer edges or outer periphery of a valve in the distal direction to move the valve against a distal valve opener. The distal valve opener can be sized and shaped to push a central region or section on the valve in a radially outward direction and part of two or more flaps can deflect in a proximal direction to open a fluid path or flow path through the valve.

In an example, the leg extensions on a distal valve opener can be axially fixed and by pushing the flaps of the valve in a distal direction against the leg extensions, the flaps can deflect radially outward by the leg extensions on the distal side of the valve. In other words, when the valve is actuated to open a flow path through the valve, the valve can be physically pushed by an actuator on a proximal side of the valve and an actuator on a distal side of the valve. In a particular embodiment, the valve can be actuated to open a flow path through the valve by being physically pushed by a ring on a proximal side of the valve and leg extensions on the distal side of the valve. The distal side can alternatively be pushed by a single leg extension having a bore.

The proximal tips of the leg extensions and the distal edge of the ring can be spaced from a plane drawn orthogonally to the lengthwise axis of the catheter assembly. In other words, the proximal tips of the leg extensions and the distal edge of the ring can be spaced and not overlap from the perspective of this plane and a gap can be provided between the two to accommodate the valve therebetween.

The proximal tips of the leg extensions and the distal edge of the ring can alternatively overlap along an axial direction, which can produce the effect of deflecting the flaps radially outwards a relatively greater amount than when there is no overlapping. Further, because the flaps can be pushed against axially fixed leg extensions on a bushing, the flaps can deflect backwards in the proximal direction by the leg extensions. In yet other examples, the proximal tips of the leg extensions and the distal edge of the ring can just touch along a plane drawn orthogonally to the lengthwise axis of the catheter assembly.

A catheter assembly can be provided comprising a valve, a proximal valve opener, a distal valve opener, a needle hub with a needle, and a catheter hub with a catheter tube.

The valve assembly can further include a tip protector for blocking the needle tip of a needle in a needle protective position.

Following successful venipuncture, a male tip, such as a male Luer, can be inserted into a proximal opening of the catheter hub to advance the proximal valve opener in a distal direction, which can move the valve in a distal direction against a distal valve opener.

The flaps of a valve can be pivoted in a proximal direction to open a fluid path through the valve. The flaps of the valve can deflect in a proximal direction by the leg extensions of the bushing of the present device. The flaps can be deflected in the proximal direction by pushing the flaps against stationary leg extensions on a distal valve opener.

The flaps on the valve can be deflected in a proximal direction by a structure located distally of the valve and abutting a distally facing surface of the valve.

The distal valve opener can be a metal bushing having a body with a cone shaped section having two or more leg extensions extending therefrom in a proximal direction. The bushing may also be made from a thermoplastic material.

The biasing or resilient nature of a valve of the present disclosure, which can be made from an elastomer, allows a valve to recoil to its more relaxed state when a male tip of a syringe or male medical implement is removed from the proximal opening of a catheter hub. Thus, flaps on the valve can recoil by moving distally while the outer edges or outer sections of the valve body can recoil proximally. This recoil can push the proximal valve opener in a proximal direction and the shoulder on the proximal valve opener can move towards or against the shoulder inside the interior cavity of the catheter hub.

A coil spring, a leaf spring, or an elastomeric cylinder or element can optionally be placed between the distal surface of the valve and an inside distal step or shoulder of the catheter hub to facilitate closing the valve. This spring or elastomeric cylinder, if incorporated, can provide extra biasing force to return the valve to a closed position when the male medical instrument is removed. The spring or elastomeric opener can also push a proximal valve opener in a proximal direction. If incorporated, the elastic component, such as the spring or elastomeric cylinder, can be spaced from the valve in the ready to use position or can contact the valve in the ready to use position.

The valve of the present disclosure can be a single use valve or can be opened and closed repeatedly, or at least more than once. The valve may be open a second time by placing a male tip into the proximal opening of the catheter hub and pushing the proximal valve opener in the distal direction.

Interiorly of a catheter hub, a septum or valve, an actuator or valve opener and a safety clip, such as a needle guard or tip protector, can be provided. Optionally, the safety clip can be omitted or can be placed outside the catheter hub, such as a in a third housing. The third housing can be different than the needle hub and the catheter hub.

A flash back plug or blood stopper assembly can be connected to a needle hub to stop blood flow out the flashback chamber of the needle hub. The flash back plug can be provided at the proximal end the needle hub to allow air to vent but stops blood from spilling out the proximal end of the body of the flash back plug, which can include a hydrophobic filter.

A valve having a valve body comprising valve disc and a valve skirt extending in an axial direction from the valve disc can be used with catheter hubs described herein. In an example, the valve disc can comprise one or more slits defining one or more flaps to be opened/closed by a valve actuator. The type of slits and flaps and the numbers of each incorporated with the valve disc can resemble those shown and described elsewhere herein.

A valve can comprise a valve body with a valve disc having a proximally facing surface and a distally facing surface. Two or more flaps can be incorporated with the valve disc, which can be deflected proximally or distally.

A valve in accordance with aspects of the present disclosure may be made with any known elastomer material. In an example, the valve is made from a poly-isoprene material. In other examples, the valve can be made from any suitable bio-compatible elastic material. Medical grade lubricants may be applied to the valve to facilitate valve functionality.

In an embodiment, the valve skirt can be positioned in a recessed section formed in the interior cavity of the catheter hub, which can prevent the valve from axially moving once situated inside the catheter hub. For example, the valve skirt can be positioned inside a groove defined by the recessed section and not axially move in both the ready to use position and during activation or actuation of the valve by a valve opener.

The recessed section of the catheter hub can be understood to be a first recessed section if the catheter hub incorporates a second recessed section inside the interior of the catheter hub.

In an example, the recessed section of the catheter hub can have a distal shoulder and a proximal shoulder defining a groove therebetween. The valve skirt of a valve can have a length that is sized and shaped to fit between the proximal shoulder and the distal shoulder. The valve skirt can fit within the groove.

In an example, a valve skirt of a valve can contact the proximal shoulder of a recessed section while a valve disc can contact the distal shoulder of the recessed section.

A valve provided herein can contact a distal shoulder and the proximal shoulder of a recessed section of a catheter hub and be restrained thereby in a ready to use position and during activation so that the valve skirt of the valve is axially fixed or not axially movable.

In an example, the outer diameter or exterior surfaced of the skirt section of a valve forms fit or size-on-size fit with a recessed section of the interior of the catheter hub. In other examples, a slight inference fit can be provided between the skirt section and the recessed section of the catheter hub. In still other examples, a small clearance can be provided between the exterior surface of the skirt section and the interior surface of the catheter hub at the recessed section with the valve skirt in contact with the proximal shoulder and the valve disc in contact the distal shoulder of the recessed section.

An outer perimeter of a valve disc can alternatively be considered part of a valve skirt, when a valve skirt is incorporated with a valve disc.

Optionally, there may be no proximal shoulder in a recessed section of a catheter hub since any forces acting on a valve will primarily be in a distal direction.

When a needle is withdrawn following use, there may be some proximally directed forces on a valve, but these proximally acting forces should be low and not enough to move the valve it from its interference fit in the catheter hub, even without the proximal shoulder.

A distal cavity chamber can be provided distal of a valve disc and proximal of a bushing, which can be used to retain a catheter tube to a catheter hub. In some examples, a helical spring or a resilient biasing element, such as an elastomeric ring or cylinder, may be provided in the distal cavity chamber, concentric with the needle, to bias the flaps of the valve disc to assist the valve disc to close the one or more slits. The resilient biasing element, if incorporated, can also move a proximal valve opener in a proximal direction.

In an example, the valve disc can comprise a valve diameter, a valve thickness measured orthogonal to the valve diameter, and one or more slits defining two or more flaps. A distance between a proximally facing surface and a distally facing surface can define a valve disc thickness. A valve skirt can extend axially to the lengthwise axis of the valve and can have an elongated wall that is generally perpendicular to the outer perimeter of the valve disc, forming a generally cylindrical valve body. In some embodiments, the valve skirt may be sloped such that the valve forms a frusto-conical structure.

The valve skirt can have a complex contour, such as having a cylindrical portion connected to a frusto-conical portion.

The skirt can extend either proximally or distally or both proximally and distally from the valve disc. Thus there can be a proximal cylindrical valve body, a distal cylindrical valve body, or both proximal and distal cylindrical valve bodies.

The valve skirt can define a valve cavity having an open proximal end. The open proximal end of the valve skirt can be sized to grip an exterior surface of the nose section, can loosely grip the exterior surface, or sufficiently large so as to not contact the exterior surface of the nose section.

The open proximal end of a valve skirt allows an actuator nose or nose section of a valve actuator to project therethrough and to advance axially within the valve cavity to actuate two or more valve flaps of a valve disc. In one embodiment, at least some part of the actuator nose including the distal actuation end of the valve actuator can be located inside the valve cavity of the valve prior to actuation by a male Luer tip.

The actuator nose of a valve opener can be narrower than the outer perimeter of the valve so that the actuation end of the nose section fits within a valve cavity of a valve and abut or touch the valve disc in the ready to use position. In some examples, the actuation end can be spaced from the valve disc in a ready to use position.

In an example, the relative dimensions between a valve and an actuator are such that a nose section of the valve actuator does not touch the interior wall surface of a skirt section of the valve with some touching contemplated.

In an example, the actuation end of a valve actuator contacts a proximally facing surface of a valve disc in a ready to use position and another part of the valve actuator, such as one or two projections, abuts a shoulder inside the catheter hub to impart a load on the valve disc in a ready to use position but not enough to open the one or more slits.

In an example, a proximally facing surface of a valve disc is biased by a valve opener in a ready to use position but the biasing is below a threshold for deflecting one or more flaps on the valve disc. In an example, one or more projections on an exterior of a valve actuator can abut a shoulder in the catheter hub to cause a distal end section of the valve opener, such as an activation end, to bias against the proximally facing surface of the valve in the ready to use position.

In other examples, the actuation end of a valve actuator can be spaced from the proximally facing surface of a valve disc in a ready to use position and a projection or projections on the valve actuator can either contact the shoulder or are spaced from the shoulder. When the one or more projections on the valve actuator are spaced from the shoulder of the catheter hub and the actuation end is spaced from the valve disc, the actuator can float within the catheter hub by a small amount in the axial direction.

In an example, the valve actuator can comprise a nose section, which can be elongated in structure and can be generally cylindrical or have a draft angle or taper that terminates in an actuation end. The actuation end can have a blunt distal end surface or can have a sharp edge. The nose section of a valve opener can have a wall surface with a continuous circumference, without a notch or a slit, such as a cylinder with a continuous wall. In some examples, a plurality of spaced apart slits, notches, and/or openings can be provided on the nose section to permit flow or fluid flushing. The nose section of the valve opener can define a bore. Fluid can flow through the bore. A needle can project through the bore of the nose section in a ready to use position.

Two actuating elements or plunger elements can extend proximally of the nose section. For example, the two plunger elements can be unitarily formed with the nose section and can extend from the nose section in the proximal direction.

A gap or space can be provided between the two plunger elements for positioning the needle guard or tip protector therebetween. The gap can define a holding space. The two plunger elements can each comprise at least two lengthwise edges and the edges are spaced from one another.

In an example, a projection can extend outwardly from an outer surface of one or both plunger elements.

A projection can extend from the outer surface of each plunger element. Each projection can resemble a ramp surface having a generally flat edge for abutting a shoulder of a recessed section of the catheter hub. The ramp surface of the projection and the direction of the ramp can allow the valve actuator to be inserted into the interior of the catheter hub and be seated within the second recessed section of the catheter hub.

In an example, a transition section of the actuator can extend from a nose section of a valve opener and widens axially in the proximal direction. Two actuating elements can extend from the transition section.

Some embodiments may utilize other shapes for the nose section, such as cuboid, rectangular, conical, pyramidal or the like. The nose section can define a bore. Fluid can flow through the bore. A needle can project through the bore of the nose section.

In an example, the actuator or valve opener has a lengthwise axis, the one or more actuating elements can extend axially or parallel to the lengthwise axis. In a particular example, two actuating elements can be diametrically opposed to one another along the lengthwise axis.

In an example, two actuating elements can define an outer diameter having a dimension that is larger than a diameter of the nose section. In other examples, the two actuating elements can define an outer diameter having a dimension that is smaller than a diameter of the nose section.

In an example, the actuating elements or plunger elements of a valve opener proximal of a nose section can be flexible and deflectable so that when pushed by a male Luer tip, the actuating elements can deflect or flex. The actuating elements can be deflectable by selecting a material that has the requisite resilient properties, such as crystalline thermoplastics.

In other examples, the actuating elements can be deflectable by incorporating one or more weakened sections, such as by incorporating a structurally thin section, by incorporating cut-outs, by employing a small cross-section compared to other sections of the same elongated actuating element, or combinations thereof.

Alternatively, the actuating elements can be flexible and deflectable by selecting a material that has the requisite resilient properties and by incorporating one or more weakened sections.

In still other examples, each actuating element can have more than one different cross-sectional profiles or contour along a length section. For example, an elongated plunger element can have a square profile located adjacent a crescent-shaped profile.

In an example, the actuating elements can be rigid and not deflectable or deformable when loaded, such as when pushed, by a male Luer tip. Further, stabilizing elements can be incorporated to increase the rigidity of the two actuating elements. The two actuating elements may each include a cross-sectional profile, at least at a proximal end, that overlaps a push end of a male tip so that the male tip can push the valve actuator into the valve.

The nose section of a valve actuator can be configured to engage the valve to open the valve disc when an axial force is applied by a male tip to the actuating elements towards the distal end of the catheter assembly, such as during the insertion of an IV Luer adapter.

Generally, the nose section of a valve opener is rigid relative to the more pliable valve, which allows the nose section, and more specifically the actuation end, to actuate the valve, such as to deflect the one or more flaps and open the one or more slits on the valve disc. The nose section may be made of a non-compressible material, such as metal, a plastic, or an elastomer which is harder than the valve material for pushing against and opening the valve.

The illustrated valve actuator embodiment can include a pair of opposed bands or stabilizer elements connecting the two actuating elements at a location along the length of the actuating elements that are between the nose section and the proximal end of the actuating elements. In some examples, the stabilizer elements can be located at the proximal end of the two actuating elements so that proximal edges of the stabilizer elements are generally flush with the proximal end surfaces of the actuating elements.

In one embodiment, the stabilizer elements, or more generically called stabilizers, can be arc-shaped, forming an arc following the interior profile of the catheter hub and connecting one actuating element to another actuating element. The stabilizers may form a substantially cylindrical section on the body of the valve actuator, which body can be spaced apart from the nose section of the valve actuator. In other words, the valve actuator can be elongated and can have sections that are continuous along a radial direction and sections with reliefs or through passages that are not continuous along the radial direction.

In an example, the stabilizers can define a continuous body section along a perimeter or radial direction of the valve actuator that is spaced from a continuous body section of the nose section, that is also continuous along a perimeter or radial direction.

The two stabilizers may be joined together with the two plunger elements to form a ring structure. Optionally, the two stabilizers may be slightly offset and angled from each other. In some embodiments, there may be one, three, or a different number of actuating elements or stabilizers. In an example, the valve actuator, with the stabilizers and projections, may be made from plastic, such as by plastic injection molding.

The stabilizers can help the valve actuator remain centered within the catheter hub while the actuator moves, such as when pushed by a male Luer tip. By staying centered, the nose section can be better aligned with the valve disc, such as the slits on the valve disc, allowing for smooth actuation of the valve.

The stabilizers can also provide an engagement, via friction, with the interior of the catheter hub to prevent the actuator from sliding out the proximal end of the catheter hub following removal of the male Luer tip.

In one embodiment, the nose section of a valve can be configured to remain engaged to the valve disc following actuation of the valve and following removal of the male Luer tip. For example, the nose section can wedge between the one or more slits on the valve disc and be held there by friction. Surface features, such as bumps, grooves, or barbs, can be provided with the valve actuator, such as on the nose section, to maintain the engagement between the actuator and the valve following actuation and following removal of the male Luer tip.

A relief, opening, or through passage can be provided between a transition section and each of the two stabilizers. The two reliefs or through passages can provide clearance so that the interior or central part of the valve actuator and the interior surface of the catheter hub can be in open communication. In other words, between the continuous section of the nose section and a stabilizing ring, one or two reliefs, through passages, or openings, can be provided. This can improve the flushing characteristics of the device.

The stabilizing ring of a valve actuator, such as the stabilizing ring, can have an inside diameter that is smaller than the diameter defined by the diagonal dimension of a distal section of two arms of a needle guard when the two arms are biased outwardly by the side of the needle shaft. Thus, during installation of the needle guard into the holding space of the valve actuator, the needle guard can deflect inside the smaller diameter to pass through the stabilizing ring and into the open areas defined by the reliefs.

A valve actuator described herein can include a nose section, a transition section, and two plunger elements extending proximally of the transition section. The nose section can define a first continuous perimeter section. Other locations of the nose section, away from the first continuous perimeter section, can comprise a slit or a slot.

Two stabilizer elements can attach to the two plunger elements on the valve opener to form a stabilizing ring, which can define a second continuous perimeter section of a valve opener. Each stabilizer element can comprise two edges, which can include a first or distal edge and a second or proximal edge. In an example, the two edges of each stabilizer element can be parallel to one another.

The two stabilizer elements can instead be skewed or slanted so that while two edges of each stabilizer element or of the same stabilizer element can be parallel to one another, the two edges from one stabilizer element can be non-parallel to the two edges of the other stabilizer element. The proximal edges of the two stabilizer elements can be offset along an axial direction or lengthwise direction of the valve actuator. The distal edges of the two stabilizer elements can be offset along an axial direction.

Two reliefs or two through passages can be provided with a valve opener. Each relief can be defined or bounded by a transition section, two plunger elements, and a respective stabilizer element. The two reliefs or through passages may be referred to as a first relief or first through passage and a second relief or second through passage.

In an example, each relief or through passage can have a perimeter. Each perimeter can be defined by the structure of the transition section or nose section, two plunger elements, and a respective stabilizer element. As the two stabilizer elements can skew or slant in different directions, the two perimeters of the two reliefs or through passages of the same valve opener can be different, such as having different perimeter contours or shapes.

A perimeter of a relief or through passage can have a continuous loop. In other words, a perimeter can be enclosed and not have a slit or a slot to break the continuity of the perimeter. However, where a stabilizer element is formed by two stabilizer segments and has a slot or a slit between the two segments, the perimeter of the relief can be an open perimeter or a non-continuous perimeter.

In some examples, two stabilizer elements can extend laterally to connect to two plunger elements without skewing or slanting in the distal direction or the proximal direction. When so configured, the edges of the two stabilizer elements can be parallel to one another. Additionally, the four edges of the two stabilizer elements can be parallel to one another and axially offset. That is, the proximal edge of one stabilizer element can be located more proximally or distally that the proximal edge of the other stabilizer element while the four edges are parallel to one another.

The proximal and distal edges of the stabilizer elements can also be other than linear or straight. For example, the two edges can have curves, undulating surfaces, jagged edges, or combinations thereof.

Two plunger element stubs or extensions can extend proximally of a stabilizing ring. Two plunger element stubs can extend from the stabilizing ring and axially align with two plunger elements located distally of the stabilizing ring.

In some examples, two plunger element stubs can extend proximally of a stabilizing ring and not axially align with the two plunger elements located distally of the stabilizing ring.

In still other examples, only one plunger element stub aligns with one of the two plunger elements located distally of the stabilizing ring.

For a valve opener or actuator with only one plunger element between a nose section with an activation end and a stabilizing ring, only one of the plunger element stubs or none of the plunger element stubs aligns with the one plunger element. There can be two or more plunger element stubs.

In some examples, there can be more than two plunger element stubs or extensions extending proximally of a stabilizing ring. The two or more plunger element stubs or extensions can be equally spaced around the proximal periphery of a stabilizing ring or randomly spaced around the proximal periphery of the stabilizing ring.

The plunger element stubs can extend the overall length of a valve actuator.

The number of plunger element stubs and/or the arc-curve of each plunger element stub, which defines a width of each plunger element stub, can provide a greater overlapping surface with a male Luer tip than fewer numbers or for a plunger element stub with a relatively smaller arc-curve.

Two plunger elements can each have at least two thicknesses to create a projection at an interface between the two thicknesses on an outside surface of each plunger element. The two projections can be located inside a recessed section so that a shoulder at a proximal end of a recessed section inside the catheter hub can provide a stop surface to prevent dislodgement of the valve opener in the proximal direction.

In some examples, only one projection can be employed on one of the two plunger elements of a valve opener to prevent dislodgement of the valve opener in the proximal direction. In still other examples, each plunger element can have a single thickness and the projection is formed by adding material to the plunger element during injection molding at the site of the projection. In still other examples, there can be more projections than the number of plunger elements.

In an example, a planar surface section can be provided with the valve actuator on the same side of each stabilizer element. The planar surface section can originate from about the nose section or the transition section of the valve member and extends proximally to about the location of the two projections.

Two planar surface sections, one on each side of the valve opener corresponding to the two stabilizer elements, can be provided as a way to minimize the overall thickness profile of the transition section and of the two plunger elements along a side profile. Thus, in an example, a cross-sectional dimension of a nose section, of a transition section, and of two plunger elements can be generally constant or be the same within typical manufacturing tolerances along a side view.

A holding space can be provided between two plunger elements, inside the stabilizing ring, between two plunger element stubs, or combinations thereof.

Part or all of a needle guard or tip protector can be located in the holding space in a ready to use position and one or two elbows of the tip protector can project out the relief or the reliefs, if two elbows are incorporated with the tip protector.

When located in the holding space, a proximal wall of a needle guard can be flush with the proximal end surface of a plunger element stub, located proximally of the end surface, or located distally of the end surface. If no plunger element stub is incorporated with the stabilizing ring, a proximal wall of a needle guard can be flush with the proximal edge of one or both stabilizer elements, located proximally of the proximal edge of one or both stabilizer elements, or located distally of the proximal edge of one or both stabilizer elements.

A distance between two inside surfaces of the two stabilizer elements can define a choke gap, choke point, or restricting point for a needle guard to limit proximal movement of the needle guard in a ready to use position and/or during retraction of the needle following intravenous access. That is, before a needle tip moves proximally of one or two distal blocking walls of a needle guard, the choke point or gap can present a smaller space for the needle guard to pass proximally of the choke point or restricting point.

After the needle tip moves proximally of one or two distal blocking walls of a needle guard, the two distal walls can move radially inwardly to decrease the needle guard's radial profile, which can be smaller than the choke gap. With a smaller radial profile measured at the two elbows, the needle guard can move proximally of the choke point. In an example, the needle guard can move proximally out the holding space and the catheter hub by a change in profile on the needle abutting a perimeter on a proximal wall of the needle guard and then pulling the needle guard at the proximal wall out the holding space of the valve actuator and catheter hub.

In an example, when the needle guard's radial profile is decreased, the needle guard can move proximally of a choke gap or choke point and can move proximally through a bore defined by a stabilizing ring.

Stabilizer elements on a valve actuator for forming a stabilizing ring can be non-continuous and each stabilizer element can include a slit or slot.

A stabilizer element on a valve opener can comprise two stabilizer segments spaced from one another by a slit or slot. Each stabilizer segment can be understood to include an inside edge that is spaced from the other inside edge of the other stabilizer segment. The two inside edges of the two stabilizer segments can define a slit or a slot therebetween. In addition to an inside edge, each stabilizer segment can also have two side edges, which can be approximately orthogonal to a lengthwise axis of the valve opener. The two stabilizer segments can be similar or the same or can be different.

When two stabilizer elements are used to form a stabilizing ring, one stabilizer element can be a continuous piece connecting two plunger elements together and the other stabilizer element can be non-continuous, such as being made from two stabilizer segments having a slit or a slot in between. Thus, the stabilizing ring can have a single slit or slot instead of two or more slits or slots.

The width of the slit or slot can be smaller than the widest width of a needle guard. The width in this regard can be understood as the dimension that is perpendicular to a lengthwise axis of the needle guard. In some examples, the width of the slit or slot can be smaller than the width of the distal walls of the needle guard, or the width of a distal wall if only one distal wall is incorporated. The width of the slit or slot can also be smaller than the width of the needle guard at the elbow.

The relative dimensions between a slit or slot on a valve opener and the width of the needle guard can be selected so that the stabilizing rings can limit proximal movement of the needle guard, such as limit the two elbows on the needle guard, from moving proximally of the stabilizing ring through the slit or slot during retraction of the needle but before activation of the needle guard. In other words, even with one or more slits or slots incorporated with the stabilizer elements of a valve opener, the stabilizing ring can still provide restraining surfaces or choke points to limit proximal movement of a needle guard.

In an example, an elbow of a needle guard cannot slide proximally through a slit or slot of a stabilizing ring. In other examples, the slit or slot of a stabilizing ring can have a tapering gap so that while some part of a needle guard can slide through the slit or slot, the narrowing taper of the slit or slot prevents movement of the needle guard completely through the slit or slot.

The valve opener of the present disclosure can incorporate one or two stabilizer elements to form a full loop or less than a full loop, which can have gaps or slots when stabilizer segments are used for one or two stabilizer elements. Thus, the one or two stabilizer elements can be continuous or be segmented with slits or slots between the segments.

A needle guard with one arm and one elbow, two arms but only one elbow, or two arms and two elbows can be used with any of the various valve actuators described herein. The needle guard can be located in a holding space of a valve actuator and the one or two elbows can extend at least partially through the reliefs or through passages of the valve actuator.

While a stabilizing ring can comprise one or more slits, such as two slits, the stabilizing ring can provide similar restrictions or choke points as a stabilizing ring without any slit or slot.

A stabilizing ring with a non-continuous perimeter section can also provide stability during axial movement of a valve actuator by acting as a bearing to guide the valve actuator against the interior surface of a catheter hub.

Each stabilizer element can comprise two non-continuous edges, which can be referred to as a distal edge and a proximal edge, or a first edge and a second edge. In an example, the two edges of each stabilizer element can be parallel to one another. The two edges from one stabilizer element can also be parallel to the two edges of the other stabilizer element in a valve opener with two stabilizer elements.

Two proximal edges of two stabilizer elements can be aligned along an axial direction or lengthwise direction of the valve actuator. The distal edges of the two stabilizer elements can also align along an axial direction. In other examples, the edges of the two stabilizer elements can be axially offset.

Two reliefs or two through passages can be provided on a valve opener, each defined or bounded by a transition section or nose section, two plunger elements, and a respective stabilizer element. The two reliefs or through passages may be referred to as a first relief or first through passage and a second relief or second through passage.

In an example, each relief or through passage can have a perimeter. In an example, each perimeter can be defined by the structure of a transition section or nose section, plunger elements, and a respective stabilizer element. The two perimeters of the two reliefs or through passages can be the same or can have different perimeter contours or shapes. When slits or slots are incorporated, one on each stabilizer element, the two perimeters of the reliefs are open, such as being non-continuous.

The valve opener can be made from a metal material. For example, a stamped metal sheet, such as a stamped stainless steel sheet, can be cold worked using deep draw methods to form the desired shape. The various openings or gaps of a needle guard can be punched or stamped and then cold worked to form the desired shaped.

Each plunger element of a valve opener can comprise at least two lengthwise edges and a rib can optionally be provided along one or both of the lengthwise edges to further add structural rigidity. One or more gaps can be provided between any two plunger elements of a valve opener. The gaps can provide clearance or space for fluid flow flowing thereacross, such as during IV infusion. The gap can also form part of a holding space to accommodate a needle guard.

Two plunger element stubs can extend from a stabilizing ring and axially align with the plunger elements located distally of the stabilizing ring of a valve opener. In other examples, the two plunger element stubs are not axially aligned with the two plunger elements located distally of the stabilizing ring. In still other examples, only one plunger element stub can be aligned with one of the two plunger elements of the valve opener.

In some examples, a valve opener can terminate at a stabilizing ring and the valve opener can be without any plunger element stubs. In still other examples, each plunger element stub located proximally of each plunger element can be considered part of the same plunger element and the stabilizer segments are tabs extending radially from the two lengthwise edges of the two plunger elements at a location distal of the proximal end surface of the actuator or valve opener.

In an example, two plunger elements extend from a nose section of a valve opener and a stabilizing ring is located between the nose section and proximal most edges of the two plunger elements.

In some examples, there can be more than two plunger element stubs or extensions extending proximally of a stabilizing ring. The two or more plunger element stubs or extensions can be equally spaced around the proximal periphery of the stabilizing ring or randomly spaced around the proximal periphery of the stabilizing ring.

The plunger element stubs can extend the overall length of a valve actuator. The number of plunger element stubs and/or the arc-curve of each plunger element stub, which can define a width of each plunger element stub, can provide a greater overlapping surface with a male Luer tip than fewer numbers of stubs or for a plunger element stub with a relatively smaller arc-curve.

In some examples, the plunger elements stubs can have curved profiles with concave and convex surfaces facing either direction relative to a lengthwise axis of the valve actuator. In other words, the convex surface can face inwards or outwards relative to the lengthwise axis of the valve actuator.

Two plunger elements can each comprise a projection on an outside surface. The projections can be located inside a recessed section of a catheter hub so that a shoulder at a proximal end of the recessed section can provide a stop surface to prevent dislodgement of the valve opener in the proximal direction. In some examples, only one projection is employed on one of the two plunger elements to prevent dislodgement of the valve opener in the proximal direction.

In an example, each projection on a valve opener can be formed by cold-working a surface of the stamped metal sheet at the respective plunger element to push out a protruding surface.

The nose section of a valve opener can have a tapered surface extending in a proximal direction that extends into a transition section. The two plunger elements can neck down from the transition section with two radiused sections.

Each plunger element of a valve opener can extend in a proximal direction from a transition section or from a nose section with a generally constant width and then necks up with a set of radiused sections. The necked up sections can transition into two stabilizer elements. The two stabilizer elements can each include two stabilizer segments or each can be formed as a single piece.

Two pair of radiused sections can be located proximally of the stabilizer element or stabilizer segments to form two plunger element stubs. The plunger elements and the plunger element stubs can both have two spaced apart lengthwise edges, which can be provided with ribs to add strength to the respective structure.

From within a stabilizing ring of a valve actuator and extending in a proximal direction, a plunger element stub can be cold-worked to form outwardly bulging portions relative to the lengthwise axis of the valve opener to form curved surfaces along the cross-section of the plunger element stub. The bulging portions can alternatively be formed inwardly to form inward bulging portions. The bulging portions can be included to form the concave and convex surfaces for the plunger element stub, or stubs if more than one is incorporated, to strengthen the structures of the stub or stubs.

A distance between two inside surfaces of the two stabilizer elements of a valve opener can define a restricting point, a choke gap or a choke point for a needle guard to limit proximal movement of the needle guard in a ready to use position and/or during retraction of the needle following intravenous access. That is, before the needle tip moves proximally of one or two distal blocking walls of a needle guard, the choke point or gap can be sized sufficiently small to prevent the needle guard from passing proximally of the choke point. However, after the needle tip moves proximally of one or two distal blocking walls of the needle guard, the two distal walls can move radially inwardly to decrease the needle guard's radial profile, which can be smaller than the choke point. With a smaller radial profile after the arm or arms of the needle guard are actuated, the needle guard can move proximally of the choke point.

In an example, a needle guard can have a distal portion that is larger than a choke point and wherein the distal portion of the needle guard can transition to have a relatively smaller profile and be smaller than the choke point. In an example, the distal portion of the needle guard is the location between two elbows of the needle guard.

When the tip protector is positioned between the two plunger elements, the two distal walls of the needle guard, more specifically the two sections with the diagonal dimension, can be located in the reliefs to engage the guard engagement surface on the interior surface of the catheter hub. This allows the needle guard to project from the holding space of the valve actuator through the two reliefs to engage with the guard engagement surface of the catheter hub or the perimeters of the two reliefs.

A second undercut or recessed section proximal of the first recessed section can be provided in the interior cavity of the catheter hub for accommodating the two sections with the diagonal dimension of the needle guard.

The needle guard can be prevented from sliding in the proximal direction during retraction of the needle following successful venipuncture by a shoulder of a recessed section or by some other surface feature on the interior of the catheter hub, such as a guard engagement surface on the interior of the catheter hub.

Optionally or alternatively, the distal edge of one or both stabilizers can provide the restraining surface to prevent the needle guard from early activation during retraction of the needle, prior to the needle tip moving proximally of the two distal walls. In addition to the distal edge, the stabilizers can also have a proximal edge.

The valve opener can be made from a metal material or from a plastic material. When made from a metal material, the valve opener can be formed by deep draw or bending methods and the arc shape cross section of the actuating element can provide added rigidity when pushed by the male Luer.

Each actuating element can comprise at least two lengthwise edges and a rib can be provided along one or both of the lengthwise edges to further add structural rigidity. One or more gaps can be provided between any two actuating elements. The gaps can provide clearance or space for fluid flow flowing thereacross, such as during flushing blood or IV infusion. The gap between the actuating elements can define a holding space to accommodate a tip protector.

In some embodiments, a majority or most if not all of the tip protector can fit within a holding space formed by a body of the valve actuator, between two plunger elements, in a ready to use position. This can allow the catheter hub to be more compact, as less longitudinal space is needed within the hub to fit both the actuator and the tip protector serially lengthwise or when the two only partially overlap in the axial direction.

The tip protector can fit completely within the holding space of the actuator to further reduce the needed space or length in the catheter hub. The proximal wall of the needle guard can be generally flush or even with the proximal end surfaces of the two plunger elements in a ready to use position. To accommodate this nesting between the needle guard and the valve actuator, reliefs can be provided with the valve actuator so that one or two elbows on the needle guard can project out from within a holding space of the valve actuator.

A relief or through passage allows a tip protector to engage with the interior of a catheter hub. Alternatively, the relief or through passage allows the tip protector to simply project out from a holding space, and contact or be spaced from a perimeter of the relief. Proximal to the relief, a stabilizer can provide additional rigidity and/or a greater engagement surface for the catheter hub.

When a tip protector only engages with the perimeter of a relief or through passage, such as the distal edge of the relief of an actuator, then no deformity or change of diameter is required on the inside wall of the catheter hub and the tip protector can still be placed in the female Luer taper section while complying with the international Luer standard for conical fittings, for current and future international standards.

Optionally, one or more grooves or recessed sections can be incorporated outside of the Luer taper of a catheter hub to accommodate any of the various components discussed herein. For example, one or more grooves can be provided distal of the Luer taper section of the catheter hub to engage a project, shoulder, elbow, or any of the various structures and components discussed elsewhere herein.

The actuating elements or plunger elements of a valve actuator can extend past the proximal edge of one or more stabilizer elements to substantially the same distance as the proximal wall of the tip protector. In an illustrated embodiment, the tip protector substantially can fit within the holding space of the actuator and the proximal wall of the tip protector is approximately even with the proximal ends of the actuating elements, in the axial direction.

In a valve actuator retracted position in which the actuator is not advanced by a male tip to open a valve, the actuation end of the nose section of the actuator can be spaced or not pushed into the valve and opening the one or more slits of the valve. This position can also be the valve pre-activated position. That is, the valve actuator retracted position can be the position in which the actuation end is not pushed into the valve to open the slits of the valve, whether before the first activation of the valve or after activation and the male Luer tip has been removed following advancement of the actuator.

Advancing the actuator in a distal direction can cause the actuation end of the actuator to advance against a valve disc and deflect the flaps radially and distally to open a fluid path to be formed through the catheter assembly.

When initially inserting a male medical implement, such as a male Luer tip, into the proximal opening of a catheter hub, the male tip can initially contact the actuating or plunger elements, plunger element stubs, or stabilizer ring on the actuator to advance a distally directed force on the actuator to open the valve. The distally directed force can move the actuator in the distal direction until the geometries of the male tip and the proximal opening of the catheter hub stop further distal advancement of the male tip.

In an example, a female Luer taper of the catheter hub and a male Luer taper of the male tip can mate and block distal advancement of the male tip further into the opening of the catheter hub. A seal is provided by the Luer engagement to prevent fluid from leaking out the proximal opening of the catheter hub when the two components mate or register.

As the actuator moves distally by the distal advancement of a male tip, the nose of the valve actuator can be urged distally and pushes against the proximally facing surface of a valve disc. In particular, the nose of the actuator can initially push against the proximally facing surface of the valve disc and since the valve can be axially fixed within a recessed section of a catheter hub, the one or more flaps on the valve disc can deflect radially and in the distal direction. Fluid from the male tip can then flow through the catheter hub, through the valve, and through the lumen of the catheter tube. A valve skirt can be provided extending in an axial direction from the valve disc.

Alternatively, a suction can be applied by a male medical instrument, such as a syringe or vacuum blood collection tube, and blood aspirated from the patient in a proximal direction through an opened valve. This can often be done for testing samples before infusion therapy is commenced. Also, typically any remaining blood can first be flushed from the inside of the catheter hub before infusion therapy is commenced.

Even after removal of a male tip following actuation, a valve actuator can remain engaged to hold the valve open. That is, the friction between the valve actuator and the valve disc can exceed the restoring forces produced by the valve in attempting to return to its un-deformed position. This activated position can be considered a one-time use or one-time actuation since the valve actuator and valve do not return to the pre-activation position when the male tip is removed.

In an alternative embodiment, the nose section of an actuator can be configured so that when pushed into the valve during activation, the actuation or activation end does not extend distally past the flaps of the valve disc. This configuration can be employed so that the valve actuator is pushed by the flaps when the male Luer implement is removed to return to its pre-activated position. A conical configuration at the distal end of the actuator can be such a configuration, which can maintain a proximally directed force vector, which is greater than a perpendicular force vector. The angle of the cone can be designed to provide the necessary force vectors when the actuator has reached it maximum distal movement and its minimum distal movement. The difference between the maximum movement and minimum movement of a standard Luer connector is approximately 2.5 millimeters. Thus, international standards for Luer fittings can be consulted with when sizing a tip of an actuator.

Additionally, a spring or an elastic element or ring, can be incorporated at a distal cavity chamber of the catheter hub to increase the re-coil or returning forces of the valve to facilitate pushing the valve actuator in the proximal direction following removal of the male tip to return to the actuator to the pre-activated position. The biasing element, which can be a spring or an elastic element, can also help to close the flaps of the valve disc and return the valve to the valve closed position. In this manner, the valve and valve actuator can be re-closed after the initial activation and re-open and so forth, repeatedly. Alternatively, the flaps can be made thicker to provide enough restoring forces without the need for an elastic element. Still alternatively, the flaps can be thicker and a biasing element is used to provide the restoring forces on the valve and the valve actuator.

The distal edge and the proximal edge on a stabilizer or a stabilizer element can be non-parallel to the proximal edge of the plunger elements or plunger element stubs, the latter if incorporated. The distal edge and the proximal edge of an upper or first stabilizer can be parallel to each other and the distal edge and the proximal edge of a lower or second stabilizer can be parallel to each other but the corresponding edges of the upper and lower stabilizers do not have to be parallel to one another. Said differently, the upper stabilizer can have a distal tilt while the lower stabilizer can have a proximal tilt.

An actuator can comprise a generally cylindrical nose section or can comprise a conical frustum shape nose or a combination of both cylindrical and conical shape sections and an activation end at a distal end thereof. Actuating arms or plunger elements can extend lengthwise from the nose section. Stabilizer elements can be incorporated and the stabilizer elements can have edges that are generally even without off-setting edges. In a ready to use position of a needle assembly or catheter assembly, the nose section may be in contact with a valve disc of a valve or can be slightly spaced from the proximally facing surface of the valve disc. The valve can further include a valve skirt having a valve cavity and the nose section, or at least the activation end of the nose section, located within the valve cavity.

A relief or through passage in the wall of a valve actuator can provide access for a tip protector to engage with the interior of the catheter hub or to otherwise be retained inside the catheter hub, as previously described. In one embodiment, two through passages or reliefs on opposite sides of the body of the actuator can be provided to give access to the interior of the catheter hub to two arms of a tip protector. Other embodiments have different number of through passages or reliefs, such as one, three or more. For example, there may be one relief or through passage in a cylindrical actuating element.

Most of the tip protector can be fitted inside a holding space of a valve actuator with only a portion of the tip protector extending in a proximal direction past the proximal end of the actuator. For example, the proximal wall and part of the two arms of the tip protector can extend proximally of the proximal end of the actuator.

One or more ribs or projections can be formed on the exterior surfaces of the actuating arms or plunger elements of an actuator to engage with a shoulder in a recessed section of a catheter hub to retain the valve actuator inside the catheter hub in the ready to use position and used position.

An interior of a catheter hub can comprise one, two, or more grooves. Each groove can comprise a recessed section formed into the wall of the catheter hub. Each recessed section can comprise a shoulder. A first groove, if incorporated, can be used to retain a valve. A second groove, if incorporated, can be used to engage one or more projections on a valve actuator to limit proximal movement of the valve actuator. A third groove, if incorporated, can be used to engage a tip protector. Additional grooves can be incorporated.

A valve can have one or more ridges, such as an engagement surface, formed on the outer surface of the valve skirt. Micro-channels can be provided on an exterior of a valve for air venting between the valve and the interior surface of a catheter hub. Medical grade lubricants can be applied on the valve to facilitate movement.

An engagement surface on a valve can comprise a projection or a groove or a combination of both a groove and a projection formed on an exterior surface of the valve. For example, the engagement surface may comprise of a section having a first outer diameter (e.g., peak/projection) and a second outer diameter (e.g., valley/groove), with the sections repeated one or more times on the outer perimeter of the valve. In another example, the grooves and/or projections may be formed as a single continuous, spiral structure on the exterior of the valve.

In some embodiments, the engagement surface on a valve can extend circumferentially along the outer surface of the valve, forming rings or a spiral thread. In other embodiments, the engagement surface can comprise several separate sections formed on the outer surface, such as separate protrusions/recesses or the thread sections on an interrupted screw.

A catheter hub may be provided with a corresponding engagement surface on the interior surface of the catheter hub to mate with the engagement surface of the valve. The engagement surface of the catheter hub can be similar to the engagement surface of the valve, but with inverse features in order to mate with the valve engagement surface.

By forming engagement surfaces on the valve and the catheter hub, the valve can be better retained in the correct position in the catheter hub, even as a valve actuator applies force to the valve. The valve, with the engagement surface and the corresponding surface inside the catheter hub, can be axially fixed within the catheter hub without a recessed section having proximal and distal shoulders.

Two engagement arms can be formed on the proximal end of a valve, extending radially inwards from the interior surface of a valve skirt. The engagement arms can be configured to mate with the engagement shoulders formed on a valve actuator. The two engagement arms on the valve can be configured to engage with the two engagement shoulders formed by two reliefs of a valve actuator. In other embodiments, different numbers of engagement shoulders and engagement arms may be used (e.g., one, three, or more).

In a ready position, a nose of an actuator can lie within a holding space of a valve, adjacent to the proximally facing surface of a valve disc of the valve. The valve skirt can surround the nose with the engagement arms on the valve partially extending into the reliefs or through passages of the actuator and engaging with the engagement shoulders. In one embodiment, the engagement arms can have a sufficiently low profile to not interfere with the needle and the tip protector, such that the arms do not interfere with the movement of the needle and the tip protector.

Aspects of the present disclosure can include a needle assembly comprising a needle hub with a needle having a needle tip extending from a distal end of the needle hub a catheter tube attached to a catheter hub having a body comprising an interior wall surface defining an interior cavity, the needle extending through the catheter tube and the needle tip out a distal end of the catheter tube in a ready to use position; a valve positioned in the interior cavity of the catheter hub, said valve comprising an outer perimeter, at least one slit and two or more flaps; a valve opener sized and shaped to open the at least one slit to open the valve, said valve opener comprising a nose section having an activation end and a continuous perimeter section, two plunger elements each having two lengthwise edges, two stabilizer elements connecting the two plunger elements to form a stabilizing ring comprising a continuous perimeter section, a holding space, and two through passages located between the nose section and the stabilizing ring; a needle guard comprising two resilient arms located at least in part inside the holding space, wherein said needle guard comprises two elbows projecting through the two through passages and in contact with a perimeter of each through passage or the interior wall surface of the catheter hub.

The needle guard can be located at least in part inside a holding space of a valve opener so that an elbow or diagonal section on an arm of the needle guard extends through one of the through passages of the valve opener. The elbow or diagonal section of the needle guard can be in contact with a perimeter of the through passage, spaced from the perimeter of the through passage, in contact with the interior surface of the catheter hub, spaced from the interior surface of the catheter hub, or a combination of contacting the perimeter of the through passage and the interior surface of the catheter hub.

A still further aspect of the present disclosure can include a needle guard comprising a resilient arm located at least in part inside a holding space of a valve opener, wherein said needle guard can comprise an elbow projecting through a first through passage, projecting through the first through passage and in contact with a perimeter of the first through passage, projecting through the first through passage and in contact with an interior surface of a catheter hub, or a combination of projecting through the first through passage and in contact with the perimeter of the first through passage and the interior surface of the catheter hub.

The elbow or diagonal section can be a first elbow and the needle guard can include a second elbow and wherein the second elbow can extend through the other one of the through passages of the valve opener, which can be called a second through passage. The second elbow or diagonal section of the needle guard can be in contact with a perimeter of the second through passage, spaced from the perimeter of the second through passage, in contact with the interior surface of the catheter hub, spaced from the interior surface of the catheter hub, or a combination of contacting the perimeter of the second through passage and the interior surface of the catheter hub.

In some examples, a valve actuator or opener can have only one through passage and a needle guard can comprise a resilient arm located at least in part inside the holding space of the valve opener, wherein said needle guard comprises an elbow projecting through the only one through passage, projecting through the only one through passage and in contact with a perimeter of the only one through passage, projecting through the only one through passage and in contact with the interior surface of the catheter hub, or a combination of projecting through the only one through passage and in contact with the perimeter of the only one through passage and the interior surface of the catheter hub.

The valve can comprise a valve disc and a valve skirt extending in a proximal direction and defining a valve cavity. The valve can optionally include a valve skirt extending in a distal direction of the valve disc.

The activation end of the valve opener can be located in the valve cavity of the valve in the ready to use position.

The activation end can be in contact with a proximally facing surface of the valve disc in the ready to use position.

The valve opener can comprise a projection extending radially of a lengthwise axis of the valve opener and wherein the projection can contact a shoulder on the interior surface of the catheter hub in the ready to use position.

The valve opener can contact both the valve disc and the shoulder at the same time in the ready to use position.

The projection can extend radially of a plunger element on the valve opener. The projection can have a ramped surface with a straight edge.

The projection can be considered a first projection and wherein the valve opener can comprise a second projection from the first projection and wherein the activation end can apply a load on the valve disc but not open the at least one slit.

A bushing can wedge a proximal end of the catheter tube against the interior surface of the catheter hub.

A resilient element can be located inside the catheter hub between the bushing and the valve disc, and wherein the resilient element can be sized and shaped to push the two or more flaps of the valve in a proximal direction.

The resilient element can be an elastic element an elastic cylinder, a helical spring, or a leaf spring. The helical spring can comprise a plurality of interconnected coils.

A further aspect of the present disclosure can include a method of assembling a needle assembly. The method can comprise the steps: providing a catheter hub with a catheter tube having an open distal end and a proximal end attached to the catheter hub by a bushing, said catheter hub comprising a hub body having an interior surface defining an interior cavity and a proximal opening; positioning a valve comprising at least one slit and two or more flaps proximal of the bushing; positioning a valve opener proximal of the valve and inside the interior cavity of the catheter hub to slidably push open the valve when actuated by a male medical implement, said valve opener comprising a nose section having an activation end and a continuous perimeter section, two plunger elements each having two lengthwise edges, two stabilizer elements connecting the two plunger elements to form a stabilizing ring comprising a continuous perimeter section, a holding space, and two through passages located between the nose section and the stabilizing ring; placing a needle, which is attached to a needle hub, through the catheter hub, the valve, and the catheter tube so that a tip of the needle extends out a distal opening of the catheter tube in a ready to use position; and placing a needle guard at least in part inside the holding space of the valve opener so that an elbow on each of two arms of the needle guard extend through the two through passages of the valve opener.

In some examples, the placing of the needle guard can comprise placing the needle guard at least in part inside a holding space of a valve opener so that an elbow or diagonal section on an arm of the needle guard extends through one of the through passages of the valve opener. The elbow or diagonal section can be in contact with a perimeter of the through passage, spaced from the perimeter of the through passage, in contact with the interior surface of the catheter hub, spaced from the interior surface of the catheter hub, or a combination of contacting the perimeter of the through passage and the interior surface of the catheter hub.

The needle guard can comprise a second elbow or diagonal section extending through the other of the two through passages. The second elbow or diagonal section can project through the other of the through passages in similar manner as the elbow or diagonal section, which can be a first elbow.

The needle guard can comprise a proximal wall and a perimeter defining an opening on the proximal wall, and wherein the two arms extend distally of the proximal wall. The needle guard can be located entirely within the interior of the catheter hub.

The needle guard can be located entirely within the interior of the catheter hub with a proximal end of the needle guard located even with a proximal end surface of the valve opener or located proximally of the proximal end surface of the valve opener or the proximal end surface of the needle guard can be located distal of the proximal end surface of the valve opener. The valve can comprise a valve disc and a valve skirt extending in a proximal direction and defining a valve cavity and wherein the activation end of the valve opener can be located in the valve cavity in the ready to use position.

The activation end of the valve opener can be in contact with a proximally facing surface of the valve disc in the ready to use position and wherein two spaced apart projections on the valve opener abut a shoulder in a recessed section of the catheter hub.

The two stabilizer elements can each comprise two parallel edges. Methods of making and of using the catheter assemblies and their components described elsewhere herein are within the scope of the present disclosure.

Aspects of the present disclosure can include a needle assembly comprising: a needle hub with a needle having a needle tip extending from a distal end of the needle hub; a catheter tube attached to a catheter hub having a body comprising an interior surface defining an interior cavity, the needle extending through the catheter tube and the needle tip out a distal end of the catheter tube in a ready to use position.

The needle assembly can further comprise a valve positioned in the interior cavity of the catheter hub, said valve comprising an outer perimeter, at least one slit, and two or more flaps.

The needle assembly can further comprise a valve opener sized and shaped to open the at least one slit to open the valve, said valve opener can comprise a nose section having an activation end and a continuous perimeter section, two plunger elements each having two lengthwise edges, two stabilizer elements connecting the two plunger elements to form a stabilizing ring comprising a continuous perimeter section, a holding space, a first through passage and a second through passage located between the nose section and the stabilizing ring.

The valve opener can comprise a nose section having an activation end and a continuous perimeter section, a plunger element having two lengthwise edges, a stabilizing ring comprising a continuous perimeter section at an end of the plunger element, a holding space, and a through passage located between the nose section and the stabilizing ring.

The holding space can be located between two plunger elements or inside a stabilizing ring.

The stabilizing ring can define a continuous perimeter section or can include one or more slits, such as a ring that is non-continuous.

The terms first, second, third, and so forth are understood to designate names to distinguish different elements, structures, or components from one another but not necessarily structurally limiting unless the context indicates otherwise. For example, a first arm and a second arm are two different arms, which may or may not have the same structure unless or as modified by further limitations.

The needle assembly can further comprise a needle guard comprising a resilient arm located at least in part inside the holding space of the valve opener, wherein said needle guard can comprise an elbow projecting through the first through passage and in contact with a perimeter of the through passage, the interior surface of the catheter hub, or both the perimeter of the through passage and the interior surface of the catheter hub.

A method of assembling a needle assembly can comprise: providing a catheter hub with a catheter tube having an open distal end and a proximal end attached to the catheter hub by a bushing, said catheter hub comprising a hub body having an interior surface defining an interior cavity and a proximal opening.

The method can further comprise positioning a valve comprising at least one slit and two or more flaps proximal of the bushing; positioning a valve opener proximal of the valve and inside the interior cavity of the catheter hub to slidably push open the valve when actuated by a male medical implement.

The valve opener usable with the method of the present disclosure can comprise a nose section having an activation end and a continuous perimeter section, two plunger elements each having two lengthwise edges, two stabilizer elements connecting the two plunger elements to form a stabilizing ring comprising a continuous perimeter section, a holding space, and two through passages located between the nose section and the stabilizing ring.

Two plunger element extensions can extend proximally of the stabilizing ring.

The valve opener usable with the method of the present disclosure can comprise a nose section having an activation end and a continuous perimeter section, a plunger element having two lengthwise edges, a stabilizing ring comprising a continuous perimeter section at an end of the plunger element, a holding space, and a through passage located between the nose section and the stabilizing ring.

The method can further comprise placing a needle, which is attached to a needle hub, through the catheter hub, the valve, and the catheter tube so that a tip of the needle extends out the open distal end of the catheter tube in a ready to use position; and placing a needle guard at least in part inside the holding space of the valve opener so that an elbow or diagonal section on an arm of the needle guard extends through one of the two through passages of the valve opener and in contact with a perimeter of the through passage, the interior surface of the catheter hub, or both the perimeter of the through passage and the interior surface of the catheter hub.

A still further aspect of the present disclosure can include a catheter assembly comprising a needle hub with a needle having a needle tip; a catheter tube attached to a catheter hub having a body comprising an interior surface defining an interior cavity, the needle extending through the catheter tube; a valve positioned in the interior cavity of the catheter hub, said valve comprising at least one slit and two or more flaps; a valve opener comprising a nose section having an activation end, at least one plunger element having a proximal end surface for pushing by a male medical implement; a needle guard comprising a resilient arm extending in a distal direction of a proximal wall comprising a perimeter defining an opening, the needle tip is configured for blocking the needle tip.

Methods of use, of making, and/or of assembling catheter assemblies and needle assemblies and components thereof as described herein are within the scope of the present disclosure.

BRIEF DESCRIPTION OF THE DRAWINGS

These and other features and advantages of the present device, system, and method will become appreciated as the same becomes better understood with reference to the specification, claims and appended drawings wherein:

FIG. 4 is a schematic cross-sectional side view of the catheter assembly of FIG. 1 in which the catheter hub is now connected with a male Luer and the proximal valve actuator advanced by the male Luer to push the valve into a distal valve actuator to open the valve.

FIGS. 5A and 5B show an end view and a cross-sectional side view, respectively, of a proximal valve actuator in accordance with aspects of the present disclosure.

FIG. 8A is a front view of an exemplary single slit disk valve.

FIG. 8B is a front view of an exemplary three slit disk valve.

FIG. 8C is a front view of a single slit disk valve with v shaped slits at each end of the single slit.

FIG. 9A is an isometric cut-away view of the needle assembly of FIG. 9 in an assembled state.

FIG. 9B is an isometric view of the needle assembly of FIG. 9.

FIGS. 10A and 10B show partial cross-sectional side views of the needle assembly of FIG. 9 in an assembled state and along different viewing planes.

FIG. 11 shows a partial perspective cut-away view of the needle assembly of FIG. 9 is an assembled state.

FIG. 12A shows a partial cross-sectional side view of the needle assembly of FIG. 9 after removal of a needle.

FIG. 12B shows a partial cross-sectional side view of the needle assembly of FIG. 12A with the valve opener advanced distally against a valve to open the valve.

FIGS. 15A-15C depict a valve opener of the present disclosure.

FIG. 16-16C depict another valve opener of the present disclosure.

DETAILED DESCRIPTION

The detailed description set forth below in connection with the appended drawings is intended as a description of the presently preferred embodiments of catheter assemblies with control valves provided in accordance with aspects of the present devices, systems, and methods and is not intended to represent the only forms in which the present devices, systems, and methods may be constructed or utilized. The description sets forth the features and the steps for constructing and using the embodiments of the present devices, systems, and methods in connection with the illustrated embodiments. It is to be understood, however, that the same or equivalent functions and structures may be accomplished by different embodiments that are also intended to be encompassed within the spirit and scope of the present disclosure. As denoted elsewhere herein, like element numbers are intended to indicate like or similar elements or features.

Figure 1:
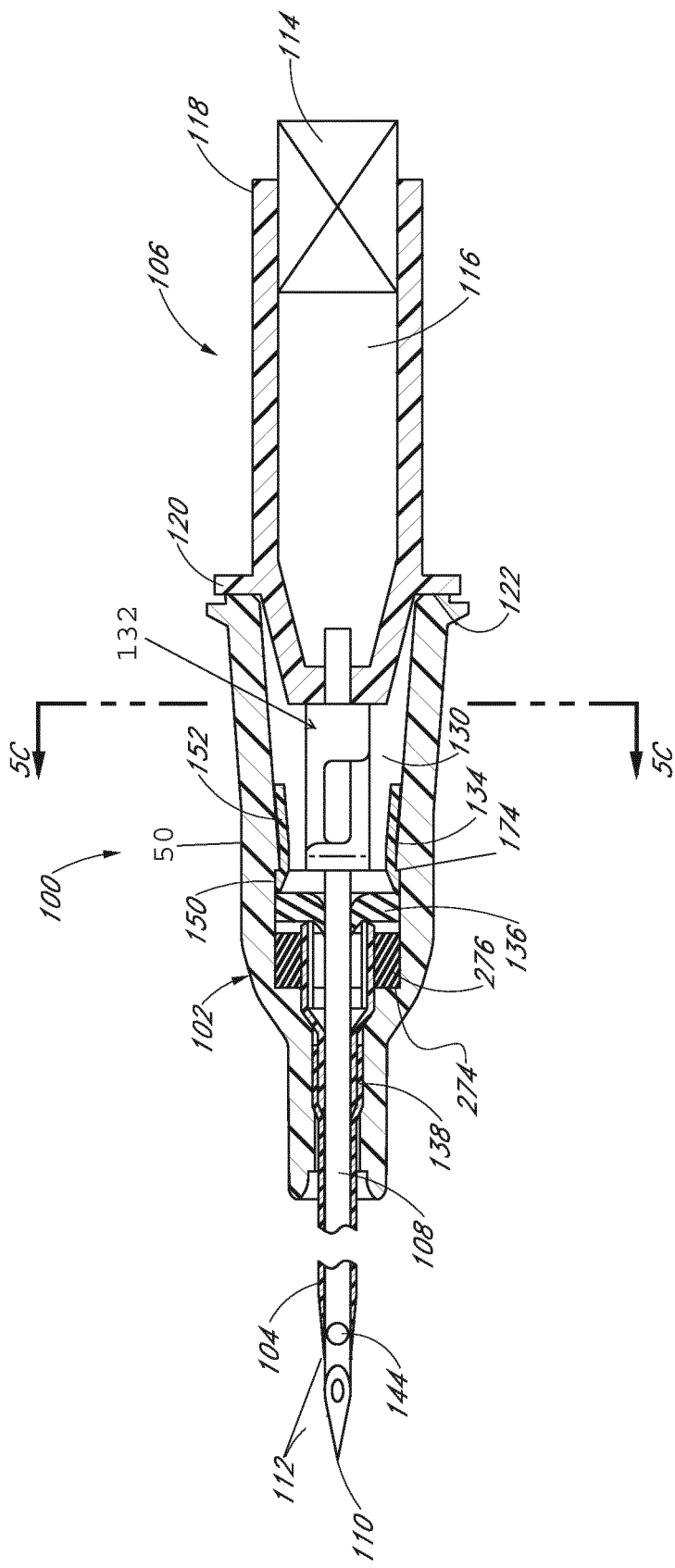
FIG. 1 is a schematic cross-sectional side view of a catheter assembly in a ready position in which the needle tip extends out a distal end of a catheter tube.

With reference now to FIG. 1, a catheter assembly 100, which may more broadly be referred to as a needle assembly or a needle device, is shown comprising a catheter hub 102 with a catheter tube 104 attached to the hub body 50 and a needle hub 106 with a needle 108 extending through the catheter hub 102 and the catheter tube 104 with the needle tip 110 extending out a distal end or distal opening 112 of the catheter tube in a ready to use position. In the ready position, the catheter assembly 100 is ready for use, such as to perform a venipuncture or intravenous access. Sometimes the ready position first requires removing a protective cap (not shown) from the catheter assembly or needle assembly 100.

A flash back plug 114 can be provided at the proximal end 118 of the needle hub 106, which allows air to vent but stops blood from spilling out the proximal end 118 when entering the flashback chamber 116 during primary flashback. Alternatively, a syringe can be attached to the proximal end of the needle hub. The valve and actuator described further below can also be placed within the needle hub as a second valve. The needle hub 106 further comprises a shoulder 120 or other surfaces that physically contact the catheter hub 102, such as the proximal end surface 122 of the catheter hub, to axially register the two hubs 102, 106 to set the length of the needle tip 110 projecting out of the distal opening 112 of the catheter tube 104.

Interiorly of the catheter hub 102, in the interior cavity 130, a needle guard or tip protector 132, a valve opener or actuator 134, a valve 136, and a bushing 138 are provided. The proximal opening of the catheter hub 102 can be sized with a female Luer taper. The bushing 138 is configured to wedge the proximal end of the catheter tube 104 against the interior wall surfaces of the catheter hub 102 to retain the catheter tube 104 to the catheter hub 102.

The tip protector 132 may embody any number of prior art guards configured for blocking the needle tip 110 of the needle. In the exemplary embodiment shown, the tip protector 132 can embody one of the guards shown in U.S. Pat. No. 6,616,630, the contents of which are expressly incorporated herein by reference. For example, the tip protector 132 can have a proximal wall and two resilient arms and wherein a change in profile 144 on the needle 108, such as a crimp or a bulge, engages a perimeter defining an opening on the proximal wall of the tip protector 132 to retract the tip protector in the proximal direction out of the catheter hub following successful venipuncture. The two arms can intersect as described in U.S. Pat. No. 6,616,630 and shown in FIG. 7 or they can run along different sides of the needle and do not intersect along a side view. The needle guard arms are spread by the needle shaft in a ready position and engage the inside of the catheter hub, such as the guard engagement section 210 (FIG. 3) of the catheter hub 102. In an example, only part of the tip protector or needle guard 132 can extend into one or more gaps of the valve opener 134 while the proximal section of the tip protector, such as the proximal wall, can extend proximally or be located proximally of the proximal most surfaces of the tip protector 132.

When the needle tip 110 is pulled into the needle guard 132 following successful venipuncture, the arms of the needle guard collapse to their protecting position to block accidental access to the needle tip. At the same time, the engagement of the arms with the inside of the catheter hub is released. The same working can also be achieved by one of the one armed needle guards described in U.S. Pat. No. 6,616,630, which runs along a side the needle shaft, instead of crossing the needle as shown in some of the embodiments of the '630 patent. Likewise the distal wall of the one arm is pushed aside by the needle shaft in the ready position. When the needle tip 110 is moved proximal of the distal wall, then the distal wall springs in front of the needle tip to block accidental access to the needle tip and at the same time the engagement between the needle guard and the inside of the catheter hub is released.

FIG. 5A shows a front view of a valve opener or actuator 134 and FIG. 5B shows a cross-sectional side view of the same valve opener taken along line 5B-5B of FIG. 5A. With further reference to FIG. 1, the valve opener 134 can comprise a ring or nose section 150 and at least one plunger element 152, such as a leg element or an elongated extension. The nose section or ring 150 is shown in contact with the valve 136 in the needle assembly ready to use position of FIG. 1 but can be slightly spaced from the proximal surface of the valve. In an exemplary embodiment, two plunger elements 152 can extend from the ring or nose section 150 in the proximal direction and each having a length measured in a lengthwise direction of the catheter assembly and a width, measured orthogonally to the length. The at least one plunger element 152 is sized and shaped for contact by a male Luer to transfer a distally directed force from the male Luer to the ring 150 to then open the valve 136, as further discussed below.

As can be visualized from the front view of FIG. 5A and the side view of FIG. 5B, the at least one plunger element 152 can have an arc shape or arc cross section along a width. In another example, the at least one plunger element 152 can be generally flat or planar. The thickness of each of two plunger elements 152 is sufficiently small or thin so that the needle guard 132 and the two plunger elements 152 have sufficient clearance to fit within the interior cross-sectional space of the catheter hub 102 without being physically binding against the catheter hub and rendered unmovable or fixed. In an example, the thickness of each of two plunger elements 152 and the width of the needle guard are such that no undercut or channel is required to be formed in the interior wall surfaces of the catheter 102 hub to accommodate them. When the plunger element 152 has an arc cross section, it will be mechanically stronger to take a greater load when being pushed by a male tip to push the ring or nose section 150 against the valve 136. This allows a thin and compact design for the infusion device and gives more room in the standardized space of a female Luer taper.

The valve opener 134 can be made from a metal material or from a plastic material. When made from a metal material, the valve opener 134 can be formed by deep draw methods and the arc shape cross section of the plunger element 152 can provide added rigidity when pushed by the male Luer. Each plunger element 152 comprises at least two lengthwise edges and a rib can be provided along one or both of the lengthwise edges to further add structural rigidity. One or more gaps 154 can be provided between any two plunger elements 152. The gaps 154 can provide clearance or space for fluid flow flowing thereacross, such as during IV infusion. The gap 154 can also be utilized to accommodate a needle guard 132, as shown in FIG. 1.

The ring or nose section 150 of the valve opener 134 comprises a body 158 with an outer perimeter 160. In an example, the outer perimeter 160 is generally cylindrical. In other examples, the outer perimeter can have a taper. Interiorly, the body 158 comprises a chamfer 162 and an opening 164. The distal edge, intersection, or activation end 166 of the body 158 between the chamfer 162 and the outer perimeter 160 can have a sharp edge or a blunt edge. In an example, the activation end or intersection 166 is a blunt edge comprising a planar surface for pushing against the valve 136, as further discussed below. On the proximal side of the ring 150, the two plunger elements 152 can be recessed inwardly from the outer perimeter 160 to form a shoulder 170. Said differently, the outer perimeter 160 can have an outside diameter of a first dimension and the two plunger elements 152 can define an outside diameter of a second dimension, which is smaller than the first dimension. A shoulder 170 is provided between the two different dimensions.

The valve opener 134 has an inside diameter measured adjacent the intersection or activation end 166. The inside diameter changes or varies along the chamfer 162 section of the ring or nose section 150. The valve opener 134 further has a minimum inside diameter mID, which can be viewed as the smallest inside diameter of the valve opener. As shown, the minimum inside diameter mID can be located at a corresponding inside location of the shoulder 170. In other examples, the minimum inside diameter mID can be located at other interior locations of the valve opener 134, such as somewhere inside the ring 150 or somewhere between the plunger elements 152.

Figure 5C:
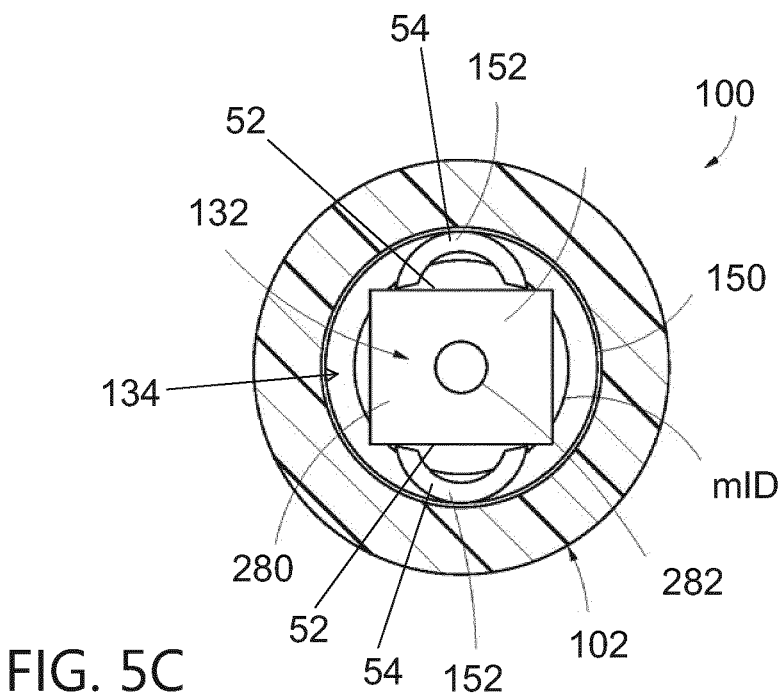
FIG. 5C shows a cross-section end view taken along line 5C-5C of FIG. 1, which shows the needle guard and inwardly arc-shaped plunger elements of the proximal valve opener.

FIG. 5C is a cross-sectional end view of the needle assembly 100 of FIG. 1 taken along line 5C-5C and shown without the needle 108. FIG. 5C shows the proximally facing wall surface of the proximal wall 280 of the needle guard 132 and two plunger elements 152. As shown, the needle guard 132 is located between one or more gaps defined by the two plunger elements 152 and the proximal wall 280 extends proximally of the proximal most edges of the valve opener 134. As previously alluded to, the plunger elements 152 can each comprise an arc-shape cross section. As shown, the arc-shape cross section of each plunger element 152 is generally C-shaped with the concave portion facing internally towards the needle guard 132 and the convex portion facing outwardly away from the needle guard 132. The arc-shape cross section of the two plunger elements 152 should have a radius of curvature that is different than the radius of the female Luer of the catheter hub 102, such as a smaller radius of curvature than the female Luer of the catheter hub. The radius of curvature of the two C-shaped plunger elements should also be different than the radius of a male Luer tip. A gap can be provided on each side edge 52 of the proximal wall 280 and the adjacent plunger element 152.

The present configuration of the valve opener 134 allows the two plunger elements 152 to define an abutting proximal surface 54 that is sized and shaped to be pushed against by a male Luer tip or a syringe tip when said tip is inserted into the proximal opening of the catheter hub 102 following successful venipuncture to push the valve opener 134 distally to open the valve 136. The arc-shape cross section of each of the two plunger elements 152 provides a sufficiently thick profile to ensure overlapping abutting surfaces with the male Luer tip and rigidity from buckling. Consequently, the C-shaped plunger elements can avoid deflection when pushed by a syringe tip or other male Luer tip, avoid slippage of the syringe tip or Luer tip missing the end surfaces 54 of the plunger elements 152 when the syringe tip or Luer tip is inserted into the open proximal end of the catheter hub, and/or avoid a situation in which the syringe tip or Luer tip is pushed between the two plunger elements to wedge the two plunger elements between the tip and the interior surface of the catheter hub 102 during activation of the valve opener 134.

Figure 5D:
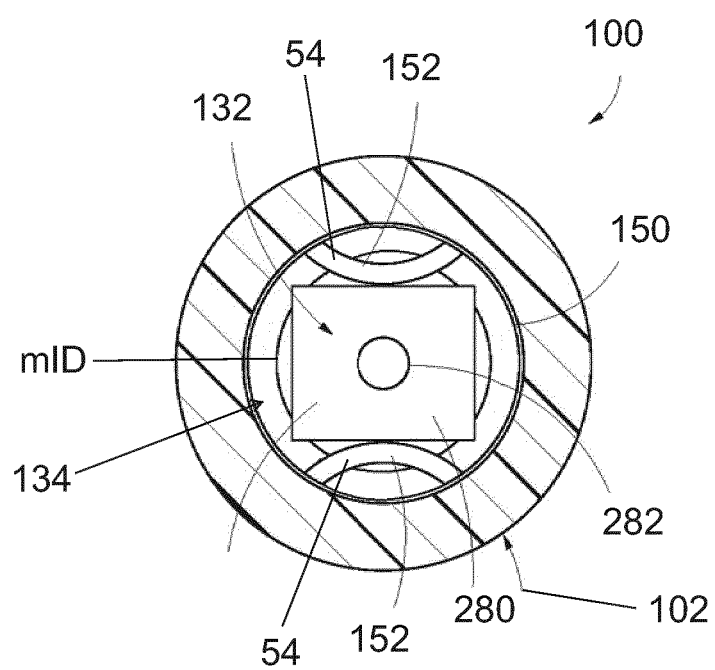
FIG. 5D is an alternative embodiment of the valve opener of FIG. 5C, showing outwardly arc-shaped plunger elements.

FIG. 5D shows the same cross-section end view of a catheter hub 102 as that of FIG. 5C but with an alternative arc-shape cross-sections on the plunger elements 152 of the valve opener 134. As shown, the two plunger elements 152 each comprises a C-shaped cross-section. However, in the present embodiment, the concave portion of the arc-shape cross-section of each plunger element 152 faces outwardly, away from the needle guard 132, while the convex portion of each plunger element faces inwardly towards the needle guard 132. Like the embodiment of FIG. 5C, the arc-shape cross-section of the two plunger elements 152 provide overlapping abutting surfaces with a syringe tip or Luer tip when the same is inserted into the catheter hub 102 to push the valve opener 134 into the valve to open the valve following successful venipuncture.

When mounted inside the interior cavity 130 of the catheter hub 102, the ring or nose section 150 of the valve opener 134 is elastically deformed and then expands when it reaches a recessed hub section 174 of the catheter hub 102, which can accommodate the ring or nose section without deforming the ring. Alternatively, the catheter hub 102 is designed to expand to allow the assembly of the valve opener 134. A shoulder 176 (FIG. 4) is provided at the recessed hub section 174, which forms a physical stop for engaging the shoulder 170 on the valve opener 134. This allows the valve opener 134 to be retained within the interior cavity 130 of the catheter hub 102 during needle withdrawal and during use, when the valve opener 134 is pushed distally to activate the valve and subsequently moves proximally when the male Luer is removed, thus allowing the valve to close.

With reference again to FIG. 1, the valve 136 is located inside the catheter hub 102 just distal of the nose section or ring 150 of the valve opener 134. In an example, the valve 136 embodies a valve disc comprising a valve body comprising a valve diameter, a valve thickness measured orthogonal to the valve diameter, and one or more slits defining two or more flaps. As used herein, valve disc and valve disk are similar or the same unless the context indicates otherwise. In a particular example, three slits are provided through the valve thickness to define three flaps. The three slits can originate from a point and extend radially from about a center point or central portion of the body of the valve 136, similar to a three-point star, to form three flaps that can deflect along the slits. The valve 136 can comprise an outer perimeter that can float inside the interior cavity of the catheter hub, between the valve opener 134 and the bushing 138. For example, the outer perimeter of the valve 136 can move proximally and distally within the interior cavity 130 of the catheter hub 102 and not be restrained by the catheter hub along an axial direction of the catheter assembly. The outer perimeter of the valve 136 can be the same or smaller or larger than the outer perimeter of the valve opener or ring 150 of the valve opener 134. However, at least some part or all of the distal edge, intersection, or activation end 166 of the nose section or ring 150 is recessed from the outer perimeter of the valve 136 so that the distal edge 166 can abut or touch the proximally facing wall surface of the valve 136, as further discussed below. Also, since the valve 136 can float, the valve can be positioned inside a single hub body catheter hub 102. In other words, the valve 136 does not have to be retained inside a catheter hub by two or more catheter hub bodies, such as along a seam of two or more hub bodies. However, the various components described herein may readily be used with a multi-piece catheter hub without deviating from the scope of the present disclosure.

Figure 6A:
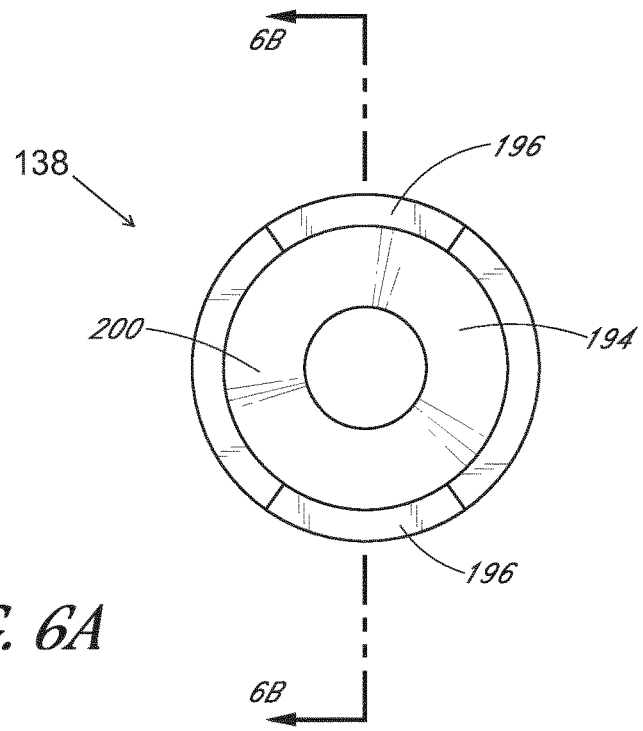
FIGS. 6A and 6B show an end view and a cross-sectional side view, respectively, of a distal valve actuator in accordance with aspects of the present disclosure.
Figure 6B:
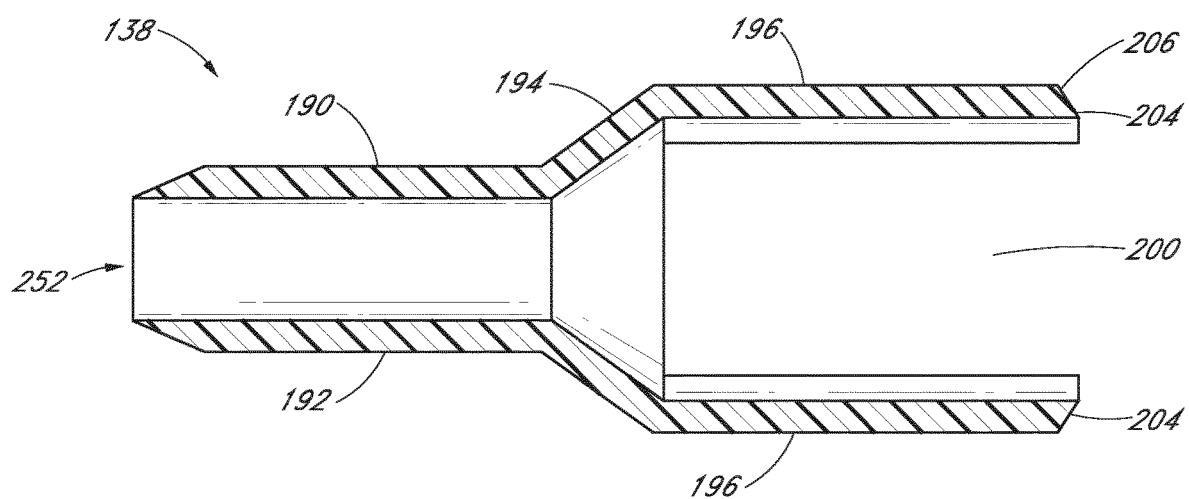

FIG. 6A shows an end view of a bushing 138 and FIG. 6B shows a cross-sectional side view of the same bushing taken along line 6B-6B of FIG. 6A. With further reference to FIG. 1, the bushing 138 comprises a body 190 comprising a first body section 192, a second body section 194 extending from the first body section 192 having a cone shape, and two or more leg extensions 196 extending from the second body section 194. The first body section 192 can have an elongated body that can have a cylindrical shape with an optional tapered distal tip or nose section. In some examples, a generally cylindrical ring extends from the second body section 194 and the two or more leg extensions 196 extend from the cylindrical ring. One or more gaps 200 are provided between two adjacent leg extensions 196. In an example, the number of leg extensions 196 incorporated with the bushing 138 is the same as the number of flaps incorporated with the valve 136. Thus, if the valve has three flaps, then there can be three leg extensions 196 on the bushing 138. If the valve 136 has a single slit, then there can be two leg extensions 196. The leg extensions 196 on the bushing 138 can define an outside diameter that is smaller than the minimum inside diameter mID of the valve opener 134. The proximal tip 204 of each leg extension 196 can have a chamfer or a blunt tip. In one example, a chamfer 206 is incorporated at the proximal tip 204 of each leg extension 196 and wherein the chamfer 206 tapers inwardly from the exterior of the leg extension 196. This chamfer direction is configured to match the folding direction of the flaps on the valve 136. The bushing 138 can be made from a metal material and the leg extensions 196 can be unitarily formed with the body 190. Alternatively, the leg extensions 196 can be welded to the body 190.

When positioned in the catheter hub 102, the bushing 138 and the valve 136 are oriented so that the leg extensions 196 on the bushing are aligned with the flaps on the valve. In other words, the two components are aligned so that when the valve 136 is advanced distally by the valve opener 134 from the proximal side, as further discussed below, the flaps on the valve are pushed into physical contact with the leg extensions 196 on the bushing 138. Thus, if there are three flaps on the valve, the three flaps will be pushed into physical contact with three leg extensions on the bushing. The distally facing wall surface of the valve 136 can touch the leg extensions 196 and/or a resilient element 276 or be spaced from the leg extensions 196 on the bushing 138 and/or the resilient element 276 in the valve closed position and be pushed against the leg extensions during use. In other examples, the valve can touch the proximal tips of the leg extensions and/or the resilient element 276 in the closed position of the valve or be spaced therefrom. If spaced from the leg extensions 196 and/or the resilient element 276, the valve 136 can be displaced axially into contact therewith.

Figure 2:
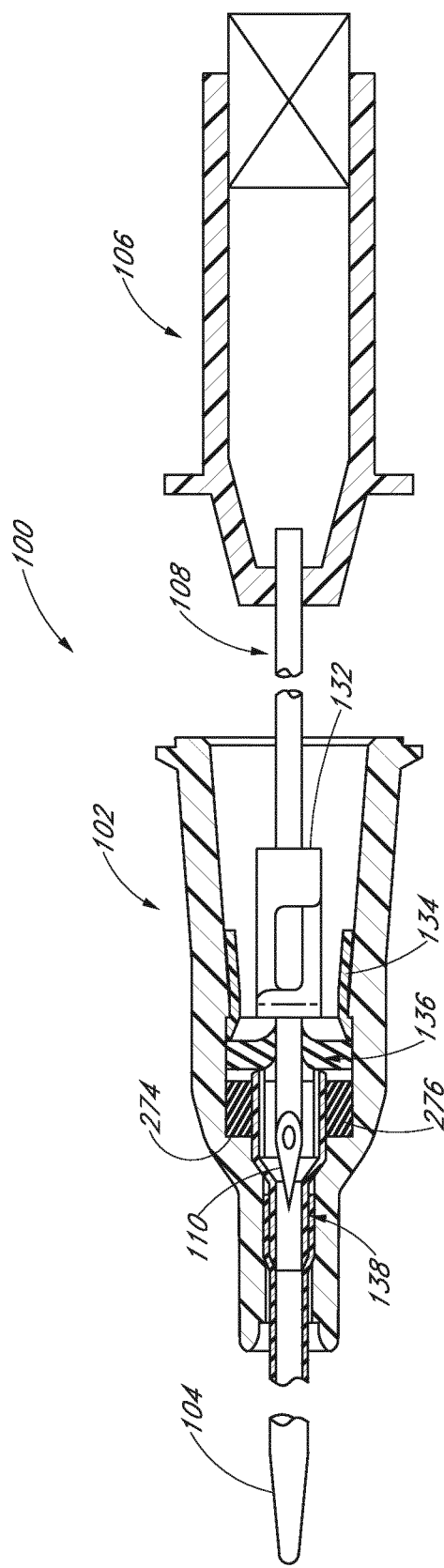
FIG. 2 is a schematic cross-sectional side view of the catheter assembly of FIG. 1 in a transition position or state in which the needle is in the process of being removed from the catheter tube and the catheter hub, such as following successful venipuncture.
Figure 6C:
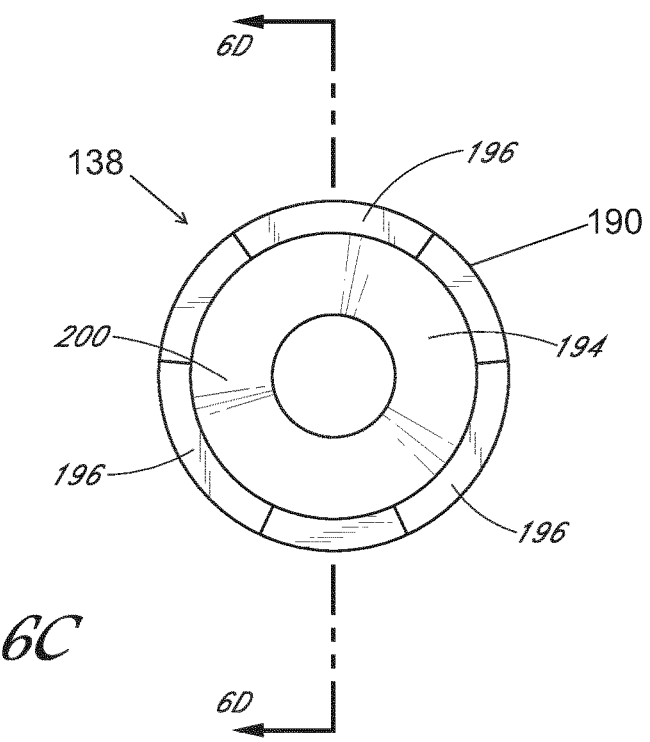
FIGS. 6C and 6D show an end view and a cross-sectional side view, respectively, of an alternative distal valve actuator having three fingers or plunger elements for use with a valve having three lugs.
Figure 6D:
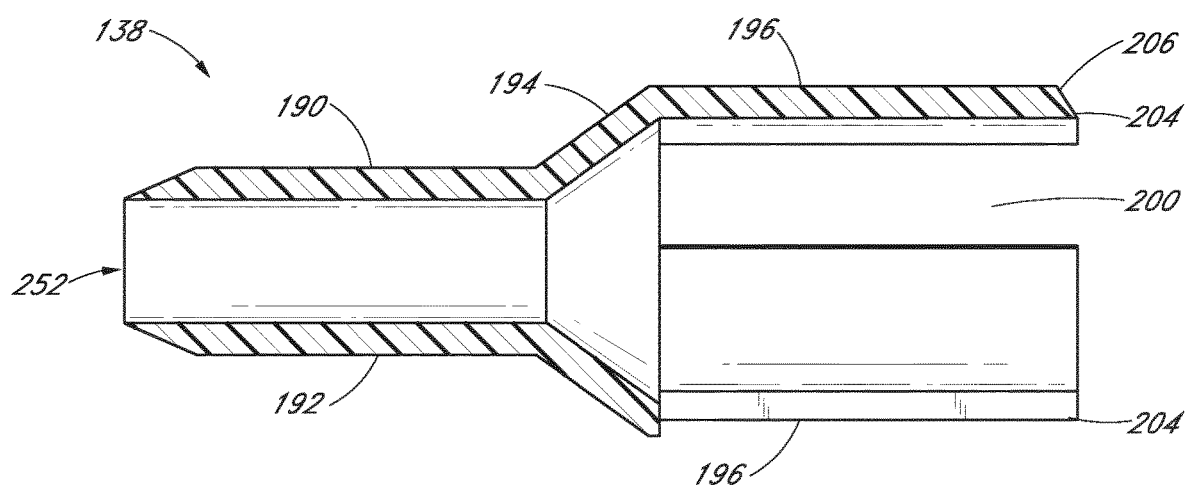

FIG. 6C shows an end view of an alternative bushing 138 and FIG. 6D shows a cross-sectional side view of the same bushing taken along line 6D-6D of FIG. 6C. Like the bushing of FIG. 6A, the present embodiment comprises a body 190 comprising a first body section 192 and a second body section 194. In the present embodiment, three leg extensions 196 are provided for use with a valve comprising three slits defining three lugs, as previously alluded. The three leg extensions 196 can be equally spaced along a circumference of the second body section 194. In another example, the three leg extensions 196 can be located and spaced in accordance with the positions of the lugs on the valve 136 so that when assembled inside the catheter hub 102, the valve can be pushed distally by the valve opener or valve actuator 134 and the leg extensions 196 on the bushing 138 are aligned to push the lugs of the valve in the proximal direction to open the valve, as further discussed below. With reference now to FIG. 2, the catheter assembly 100 is shown in a transition position whereby the needle 108 is in the process of being separated from the catheter hub 102 and the catheter tube 104, such as following successful venipuncture. The needle tip 110 is shown just distal of the valve 136. During retraction of the needle 108 in the proximal direction, the tip protector 132 is held axially by the engagement between one or both resilient arms on the tip protector 132 and a guard engagement section 210 (FIGS. 3 and 4) on the catheter hub 102. In an example, the guard engagement section 210 is a surface discontinuity formed on the interior surface of the catheter hub 102. For example, the guard engagement section 210 can comprise a section of a first inside diameter and a section of a second inside diameter, which is larger than the first inside diameter. The guard engagement section 210 can embody an internal projection or a groove or a combination of both a groove and a projection formed on the interior surface of the catheter hub 102. When a combination of a groove and a projection is used for a guard engagement section 210 to engage the needle guard or tip protector 132, then it is preferred that the groove is distal to the projection. In an example, two spaced-apart guard engagement sections 210 are provided for engaging the two resilient arms on the tip protector 132. The two guard engagement sections 210 can be located diametrically opposed to each other just distal of the section of the female Luer taper of the catheter hub 102.

Figure 5E:
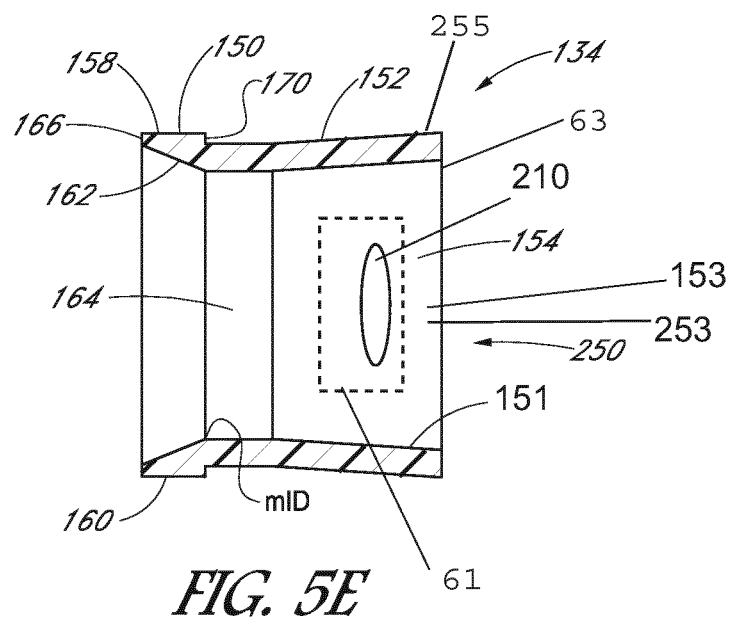
FIG. 5E shows an alternative embodiment of the valve opener of FIG. 5B, wherein the proximal section is a cylinder for surrounding at least part of a needle guard.

FIG. 5E shows a valve opener 134 provided in accordance to an alternative embodiment of the present disclosure. The present valve opener 134 is similar to the valve opener 134 of FIGS. 5A and 5B and comprises a nose section 150 with an activation end 166 and two plunger elements 152 extending in the proximal direction of the nose section 150. However, rather than incorporating two plunger elements 152 with two free ends, the present embodiment incorporates a band or ring connecting the two plunger elements 152 together. Two arc-shape, curved sections, or stabilizer elements 253 can attach to the two plunger elements 152 to form the band or ring 255. The band 255 can be called a stabilizing ring 255 and can connect the two plunger elements 152 together to form a stabilizing structure. The stabilizing ring 255 forms a continuous perimeter section of the valve actuator that is spaced from another continuous perimeter section defined by the nose section 150 of the valve actuator.

The present valve actuator embodiment 134 can also be viewed as a valve opener 134 with a single plunger element 152 extending from a nose section 150 and wherein the single plunger element 152 comprises two or more reliefs or through passages 61 formed through the wall of the plunger end. The needle guard 132 can engage the edges or perimeters 65 of the reliefs 61 in the ready to use position and during retraction of the needle following successful venipuncture. Alternatively, the tip protector or needle guard 132 can project from the holding space defined by the valve opener 134 through the reliefs 61 to engage the interior surface of the catheter hub 102. Still alternatively, the tip protector 132 can project through the reliefs 61 but not contact the interior of the catheter hub or the perimeters 65. Still alternatively, the tip protector 132 can project through the reliefs 61, contacts the interior of the catheter hub, and contacts one or both perimeters of the reliefs. The part of a tip protector that can project through one or both reliefs can be one or two elbows of a tip protector.

The needle guard 132 (FIG. 7) of the present embodiment can be positioned, at least in part, in a holding space 155 of the valve opener 134. When situated in the holding space 155, the needle guard or tip protector can project through one or both reliefs 61 of the valve opener. The part or parts of the needle guard that project through can contact the interior of the catheter hub, be spaced from the interior of the catheter hub, can contact one or both perimeters 65 of the reliefs, or be spaced from one or both perimeters of the reliefs, or combinations thereof. The part of the needle guard that projects can be one or two elbows of a needle guard.

Thus, in the embodiment with two reliefs or through passages 61, the perimeters of the two reliefs or through passages can function as guard engagement sections 210 by allowing the elbows of the tip protector to engage thereto. Alternatively, the two elbows of the needle guard can project through the two reliefs from the holding space defined by the valve opener to engage the guard engagement sections or segments formed on the interior surface of the catheter hub. Thus, the perimeters of the reliefs or the interior surfaces of the catheter hub can form anchor points for the arms of the tip protector to engage thereto in the ready to use position and during retraction of the needle following successful venipuncture.

In an example, the single plunger element 152 of the valve opener 134 of FIG. 5E can embody a generally cylindrical body section 151 having an interior surface 153 defining a bore having a path or channel 154, which can also be a gap for fluid flow, and a proximal perimeter or end edge 63. A guard engagement section 210, similar to the guard engagement segment 210 shown in FIG. 4, can be formed on the interior surface 153 of the present valve opener 134. In other words, the projection, bump, recess or guard engagement section 210 can be formed on the interior wall surface 153 of the valve opener to allow engagement between the needle guard and the interior surface of the valve opener.

When the present alternative valve opener 134 of FIG. 5E is used with a needle device or catheter assembly 100, such as the assembly of FIG. 1, the guard engagement segment 210 can be on the catheter hub, on the interior wall of the valve opener, or a perimeter of a relief formed through the wall of the valve opener. There can be one or more reliefs or guard engagement segments incorporated with the valve opener. There can also be one or more guard engagement segments formed with the catheter hub for use with the one or more reliefs of the valve opener. This allows the two resilient arms of the tip protector 132 to engage the valve opener 134 or to engage the catheter hub by projecting through the reliefs.

In yet another example, two openings 61 shown in dashed-lines (only one shown) can be provided through the wall layer of the cylindrical body portion 151 of the valve opener for use with the guard engagement segment 210 formed with or on the interior of the catheter hub 102. In the ready to use position using the valve opener of the present alternative embodiment, the resilient arm or arms of the tip protector 132 can project through the opening 61, or through two openings 61, to engage the guard engagement segment(s) 210 of the inside of the catheter hub 102 instead of or in addition to engaging the opening 61 of the valve opener 134.

Figure 3:
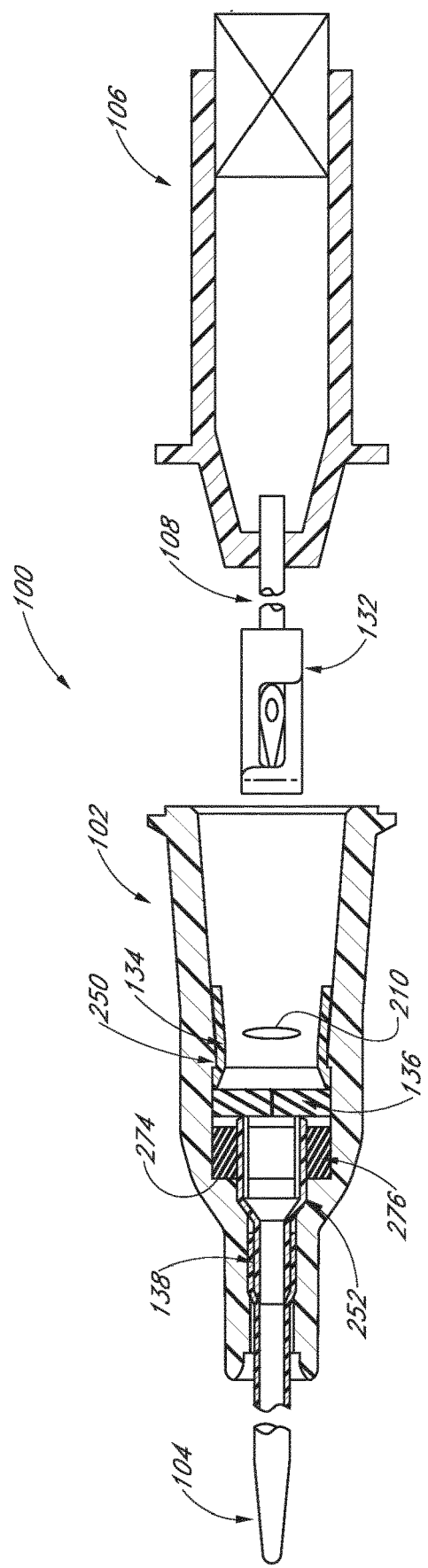
FIG. 3 is a schematic cross-sectional side view of the catheter assembly of FIG. 1 in which the needle has completely separated from the catheter hub and the needle tip is covered by a needle guard.

FIG. 3 shows the needle 108 completely removed from the catheter hub 102 and the tip protector 132 covering the needle tip 110 (FIG. 1) in a protective position. In transitioning from the position of FIG. 2 to the position of FIG. 3, the needle tip 110 moves proximally of two distal walls 300, 302 (FIG. 7), one on each end of the resilient arms 288, 290 (FIG. 7), of the tip protector 132. Alternatively, the needle guard 132 can have one distal wall and/or one arm. As the two distal walls and hence the two resilient arms are no longer biased outwardly by the needle 108, the two arms 288, 290 move radially to disengage from the two guard engagement sections 210 of the catheter hub 102, or of the valve opener 134 (FIG. 5E), if the latter is alternatively used. Alternatively, the one arm and one distal wall disengage from the one guard engagement section 210.

As the needle continues to move in the proximal direction and the change in profile 144 (FIG. 1) engages the perimeter 282 (FIG. 7) on the proximal wall of the tip protector 132, the tip protector 132 is moved proximally with the needle to the position shown in FIG. 3. Alternatively the needle guard can clamp onto the needle shaft and be removed from the catheter hub as a unit. Note that in the protective position in which the tip protector 132 covers the needle tip, the valve 136 remains inside the interior cavity of the catheter hub 102. Thus, the valve 136 is located inside the catheter hub 102 in both the ready position of the needle and the protective position of the needle. Viewed from another perspective, the valve 136 is located inside the catheter hub 102 in both the ready to use position of the catheter assembly 100, in which the needle tip projects out a distal opening 112 (FIG. 1) of the catheter tube 104, and a protective position of the catheter assembly, in which the needle is removed from the catheter hub and the needle tip is covered by a tip protector.

With reference now to FIG. 4, the catheter hub 102 is shown with a male medical implement 220 positioned in the proximal opening thereof. The male medical implement or instrument 220 can be a male Luer, a syringe tip, an IV set connector, or other male tip having a Luer taper. For example, the male medical implement can be connected to an IV tubing, which is connected to an IV fluid source for fluid delivery through the male medical implement 220, the catheter hub 102, and the catheter tubing 104 to deliver fluid therapy to a patient.

With reference to FIGS. 5A, 5B, 6A, 6B, and continued reference to FIG. 4, when initially inserting the male medical implement 220, herein male tip, into the proximal opening of the catheter hub 102, the male tip initially contacts the two plunger elements 152 on the valve opener 134 to advance a distally directed force on the two plunger elements 152 to open the valve 136. The arc cross section of the plunger elements 152 can have a smaller diameter than the inside diameter of the catheter hub 102 to provide a larger contact surface for the distal end of the male medical instrument 220, as previously discussed. This can also be designed to contact the inside wall of the catheter hub at a tangential point. In this way, the plunger elements 152 are stable and can resist being deflected outwards. This arrangement can avoid the relatively thin plunger elements from wedging between the male medical instrument 220 and the inside wall of the catheter hub 102. The distally directed force moves the valve opener 134 in the distal direction until the geometries of the male tip 220 and the proximal opening of the catheter hub stop further distal advancement of the male tip. In an example, a female Luer taper of the catheter hub 102 and a male Luer taper of the male tip 220 register and block distal advancement of the male tip further into the opening of the catheter hub. A seal is provided by the Luer engagement to prevent fluid from leaking out the proximal opening of the catheter hub.

As the valve opener 134 moves distally by the distal advancement of the male tip 220, the ring 150 is urged distally and pushes against the proximally facing surface of the valve 136. In particular, the distal edge 166 of the valve opener 134 initially pushes against the proximally facing surface of the valve 136. As the valve 136 is axially movable inside the catheter hub 102, the valve 136 is urged distally by the valve opener 134, which is urged distally by the male tip 220. For example, the ring 150 contacts and pushes the valve 136 in the distal direction. However, due to the presence of the leg extensions 196 on the bushing 138, the outer edges or outer valve sections of the valve 136 moves distally while other parts on the valve 136 that abut or contact the leg extensions 196 are stopped from moving distally by the leg extensions 196. In effect, the outer edges of valve 136, such as outer sections of the body of the valve 136, move distally while the flaps on the valve are deflected from a central point or location radially outwardly and in a proximal direction by the leg extensions 196 on the bushing 138 to open a flow path 226 through the valve. Fluid from the male tip 220 can then flow through the catheter hub 102, through the valve 136, and through the lumen of the catheter tube 104. Alternatively, a suction can be applied by the male medical instrument, such as a syringe or vacuum blood collection tube, and blood aspirated from the patient. This is often done for testing samples before infusion therapy is commenced. Also, typically any remaining blood is first flushed from the inside of the catheter hub 102 before infusion therapy is commenced.

With further reference to FIGS. 4, 5B and 6B, the chamfer 162 on the ring 150 and the chamfers 206 on the leg extensions 196 facilitate deflection of the flaps on the valve radially outwardly and in the proximal direction. Also, the relative diameters defined by the leg extensions 196 and the minimum inside diameter mID of the valve opener 134 allow the valve opener and the bushing to deflect the valve 136 therebetween to open the valve. Alternatively, the outer perimeter of the valve can remain in contact with the inside wall of the catheter hub, when pushed distally, with only the flaps opening around the slit or slits.

Thus, an aspect of the present disclosure is understood to include a catheter assembly comprising a valve comprising one or more slits and two or more flaps wherein the valve comprises parts or sections that move in a distal direction and parts or sections that open along a radial direction and in a proximal direction to open a flow path through the valve. In an example, outer edges of the valve are configured to move distally while the flaps of the valve are configured to move radially outwards to open a flow path through the valve. Also, by incorporating a valve that can move in this fashion to open a fluid flow path, the actuation distance that the valve opener 134 has to travel in the axial direction of the catheter assembly is minimized compared to a valve having flaps that only open in the distal direction by a valve opener. Thus, the size of the catheter hub 102, such as the length of the catheter hub, can be reduced compared to one that utilizes a valve and a valve opener that opens the valve by deflecting the valve flaps only in the distal direction.

A further aspect of the present disclosure is understood to include a catheter assembly comprising a valve and wherein the valve perimeter can float in the axial direction relative to the catheter hub. In other words, by incorporating a valve with a valve perimeter that can float in the axial direction, a two-part catheter hub is not required to secure the valve perimeter therebetween and inside the catheter hub. Therefore, a catheter hub with a singularly formed hub body may be used with the present catheter assembly. Thus, the size of the catheter hub 102, such as the outer diameter or dimension of the catheter hub, can be reduced compared to one that utilizes a two-part hub body. The two part hub body where they join along a seam can thus be reduced to provide a catheter assembly with a relatively smaller outer profile.

A still yet further aspect of the present disclosure is understood to include a valve opener 134 for opening a valve 136. The valve opener 134 is configured to push the valve against another structure, such as the leg extensions 196 on the bushing 138. The present valve opener 134 may be viewed as having a multi-piece valve opening structure. For example, the part with the ring 150 and the plunger elements 152 may be viewed as a proximal valve opener 250 and the bushing 138 with the leg extensions 196 may be viewed as a distal valve opener 252. The two valve openers 250, 252 cooperate to open the valve 136. As described, the proximal valve opener 250 is sized and shaped to push against the outer edges of the valve 136 in the distal direction to move the valve against the distal valve opener 252. The distal valve opener 252 is sized and shaped to push the flaps on the valve in a radially outward direction and part of the flaps in a proximal direction to open a fluid path or flow path 226 through the valve 136. In an example, the leg extensions 196 on the distal valve opener 252 are axially fixed and by pushing the flaps of the valve in a distal direction against the leg extensions, the flaps are deflected radially outward by the leg extensions on the distal side of the valve 136. In other words, when the valve is actuated to open a flow path through the valve, the valve is being physically pushed by an actuator on a proximal side of the valve and an actuator on the distal side of the valve. In a particular embodiment, the valve can be actuated to open a flow path through the valve by being physically pushed by a ring on a proximal side of the valve and leg extensions on the distal side of the valve.

In the valve open position of FIG. 4, the proximal tips 204 of the leg extensions 196 and the distal edge 166 of the ring 150 are spaced from a plane drawn orthogonally to the lengthwise axis of the catheter assembly. In other words, the proximal tips 204 of the leg extensions 196 and the distal edge 166 of the ring 150 do not overlap from the perspective of this plane and a gap is provided between the two to accommodate the valve 136 therebetween. In another example, the proximal tips 204 of the leg extensions 196 and the distal edge 166 of the ring 150 do overlap along an axial direction, which has the effect of deflecting the flaps radially outwards a relatively greater amount than when there is no overlapping. Further, because the flaps are pushed against axially fixed leg extensions 196 on the bushing, the flaps are deflected backwards in the proximal direction by the leg extensions 196. In yet other examples, the proximal tips 204 of the leg extensions 196 and the distal edge 166 of the ring 150 just touch along a plane drawn orthogonally to the lengthwise axis of the catheter assembly.

In a still further aspect of the present disclosure, a catheter assembly is provided comprising a valve, a proximal valve opener, a distal valve opener, a needle hub with a needle, and a catheter hub with a catheter tube. The valve assembly can further include a tip protector for blocking the needle tip in a needle protective position. Following successful venipuncture, a male tip, such as a male Luer, can be inserted into a proximal opening of the catheter hub to advance the proximal valve opener in a distal direction, which moves the valve in a distal direction against the distal valve opener. However, rather than deflecting the flaps in a radially outward and distal direction to open a fluid path through the valve, the flaps are pivoted in a proximal direction to open the fluid path through the valve. For example, the tips of each of the flaps of the valve, which typically originate from a point or origin near a central location of the valve, are deflected in a proximal direction by the leg extensions 196 of the bushing of the present device. In an example, the flaps are deflected in the proximal direction by pushing the flaps against stationary leg extensions 196 on a distal valve opener 252. In other words, the flaps on the valve can be deflected in a proximal direction by a structure located distally of the valve and abutting a distally facing surface of the valve 136. The distal valve opener 252 can be a metal bushing having a body with a cone shaped section having two or more leg extensions extending therefrom in a proximal direction. The bushing may also be made from a thermoplastic material.

To change the male tip 220 or to simply close the valve 136 from the open position of FIG. 4, the male tip 220 is removed in the distal direction away from the catheter hub 102. The biasing or resilient nature of the valve 136, which can be made from an elastomer, allows the valve to recoil to its more relaxed state. Thus, the flaps on the valve will recoil by moving distally while the outer edges or outer sections of the valve body recoil proximally, which pushes the proximal valve opener 250 in the proximal direction and the shoulder 170 on the proximal valve opener 250 towards or against the shoulder 176 inside the interior cavity of the catheter hub. The valve 136 and the proximal valve opener 250 therefore return to substantially the position shown in FIG. 3 after removal of the male tip from the catheter hub.

Alternatively or optionally, a softer material (not shown) resilient element 276 than the valve 136 may be placed between the distal surface of the valve and an inside distal step or shoulder 274 of the catheter hub 102, which is shown schematically in FIGS. 1-4. The resilient element 276 can be a coil spring, a leaf spring, or an elastomeric cylinder. The resilient material 276, if incorporated, can provide extra biasing force to return the valve 136 to a closed position when the male medical instrument 220 is removed. The elastic component or resilient element 276 can be spaced from the valve 136 in the ready to use position shown in FIG. 1 or can contact the valve in the ready to use position.

The valve 136 may be opened again by placing a male tip 220 into the proximal opening of the catheter hub 102 and pushing the proximal valve opener 250 in the distal direction, as described above with reference to FIG. 4.

Figure 7:
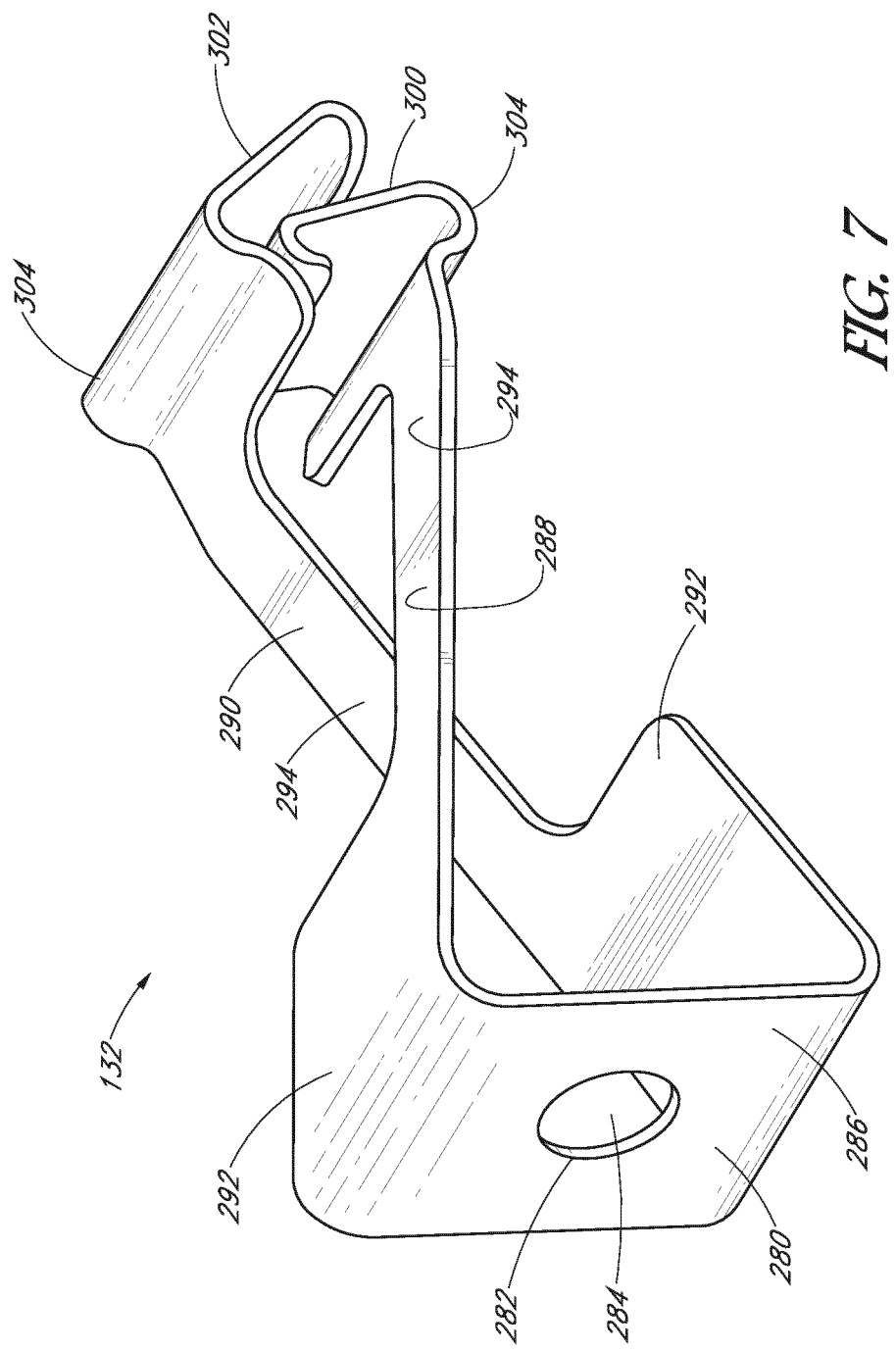
FIG. 7 is an isometric view of the needle guard of FIG. 1.

FIG. 7 is a rear isometric view of the needle guard 132 of FIG. 1. The needle guard 132 is exemplary only as needle guards with other or different features may be used instead of the exact needle guard 132 shown in FIG. 7. In the present embodiment, the needle guard 132 comprises a proximal wall 280 comprising a perimeter 282 defining an opening 284. The proximal wall 280 has a proximally facing wall surface 286 and a distally facing wall surface opposing the proximally facing wall surface. At least one resilient arm 288 extends distally of the proximal wall 280. As shown, two resilient arms 288, 290 extend distally of the proximal wall. One arm can be longer than the other arm. Each arm can also include different arm widths, including a first arm section 292 of a first width and a second arm section 294 of a second width, which is smaller than the first width. The two arms can originate from different ends of the proximal wall 280 and can cross one another at their respective second arm sections 294. Thus, when viewed from a side along the lengthwise direction of the needle guard 132, the two arms intersect one another. When used with a needle, the two arms 288, 290 intersect one another when in a ready to use position and when in the protective position. In an alternative embodiment, the two arms 288, 290 originate from different ends of the proximal wall and extend in a distal direction without crossing one another. Thus, the two arms 288, 290 can also have essentially the same arm width along the length of each respective arm.

A distal wall 300, 302 is provided at an end of each arm 288, 290. The distal walls 300, 302 can overlap one another along an axial direction of the needle guard by utilizing different arm lengths and/or angling one of the walls at an elbow or diagonal section 304 between the distal wall and the resilient arm. In an example, the elbow or diagonal section 304 of each arm, if two arms are utilized, can engage a corresponding guard engagement section 210 inside the catheter hub 102, inside the valve actuator 134, or against a restraining or restricting surface(s) or choke point(s) of one or two reliefs of the valve actuator 134 to removably secure the needle guard inside the catheter hub in the ready position and during the transition process of removing the needle 108 from the catheter hub 102. When the radial profile of the needle guard 132 measured at the one or two elbows 304 reduce in size, such as following movement of the needle tip proximally of the two distal walls 300, 302, the needle guard 132 can move proximally of the choking or choke point to be removed from the catheter hub 102 with the needle. When the two distal walls move radially, the needle guard reduces its radial profile. The needle guard 132 may be folded from a stamped metal sheet to form the guard as shown. Ribs may be formed on the arms, the proximal wall, and/or the distal walls to increase structurally rigidity.

With reference now to FIG. 8A, a front view of an exemplary valve 136 provided in accordance with aspects of the present disclosure is shown, which may be usable with the catheter assemblies and hubs with a female Luer described elsewhere herein. The valve 136 is shown with a valve body 320 having a width measured from one edge to another edge of the outer perimeter 322 of the valve body. The width of the valve body in the present embodiment is the same as the diameter of the valve body because of the circular configuration of the exemplary valve. The valve body 320 has a thickness, which is the dimension that extends into the page of FIG. 8A or orthogonal to the width. The valve 136 is shown with a single slit 324 formed through the thickness of the valve body 320, which defines a first flap 326a and a second flap 326b. The flaps can collectively generally be referred to with element number 326. The first flap 326a and the second flap 326b can be deflected to open a flow path 226 through the valve body 320. The first flap and the second flap can be deflected by pushing the valve 136 with a valve opener on a proximal side of the valve into leg extensions on a distal side of the valve, as previously discussed.

FIG. 8B is a front view of an exemplary valve 136 provided in accordance with further aspects of the present disclosure, which may be usable with the catheter assemblies and hubs with a female Luer described elsewhere herein. The present valve 136 is similar to the valve of FIG. 8A with a few exceptions. In the present embodiment, three slits 324 are provided through the thickness of the valve body to form three flaps 326a, 326b, 326c. The three slits 324 can intersect at a single central point 328. The first flap 326a and the second flap 326b can be deflected to open a flow path 226 through the valve body 320. The first, second and third flaps 326a, 326b, 326c can be deflected by pushing the valve 136 with a valve opener on a proximal side of the valve into leg extensions on a distal side of the valve, as previously discussed. A fluid flow path 226 is provided when the three flaps are deflected. In an example, the flaps 326a, 326b, 326c near the central point 328 expand radially towards the outer perimeter 322 and in the proximal direction when deflected by leg extensions on the distal side of the valve 136. As there are three flaps 326a, 326b, 326c, the present valve is configured to be used with a bushing having at least three leg extensions, as shown in FIGS. 6C and 6D.

FIG. 8C is a front view of an exemplary valve 136 provided in accordance with still further aspects of the present disclosure, which may be usable with the catheter assemblies and hubs with a female Luer described elsewhere herein. The present valve 136 is similar to the valve of FIG. 8A with a few exceptions. In the present embodiment, the single slit 324 for forming a first flap 326a and a second flap 328b is provided with reliefs 340, 340 at both ends of the slit 324. In an example, the reliefs 340, 340 embody two short through cuts 340a, 340b at each end of the slit 324 forming a V-shaped relief 340. The two reliefs 340 and 340 provide clearance for the two flaps 326a, 326b to enable them to deflect more readily when pushed against the leg extensions with fewer restrictions at points near the two ends of the slit 324 when no reliefs are incorporated. Less preferably, a single short through cut may be incorporated at each end of the slit 324.

Figure 9:
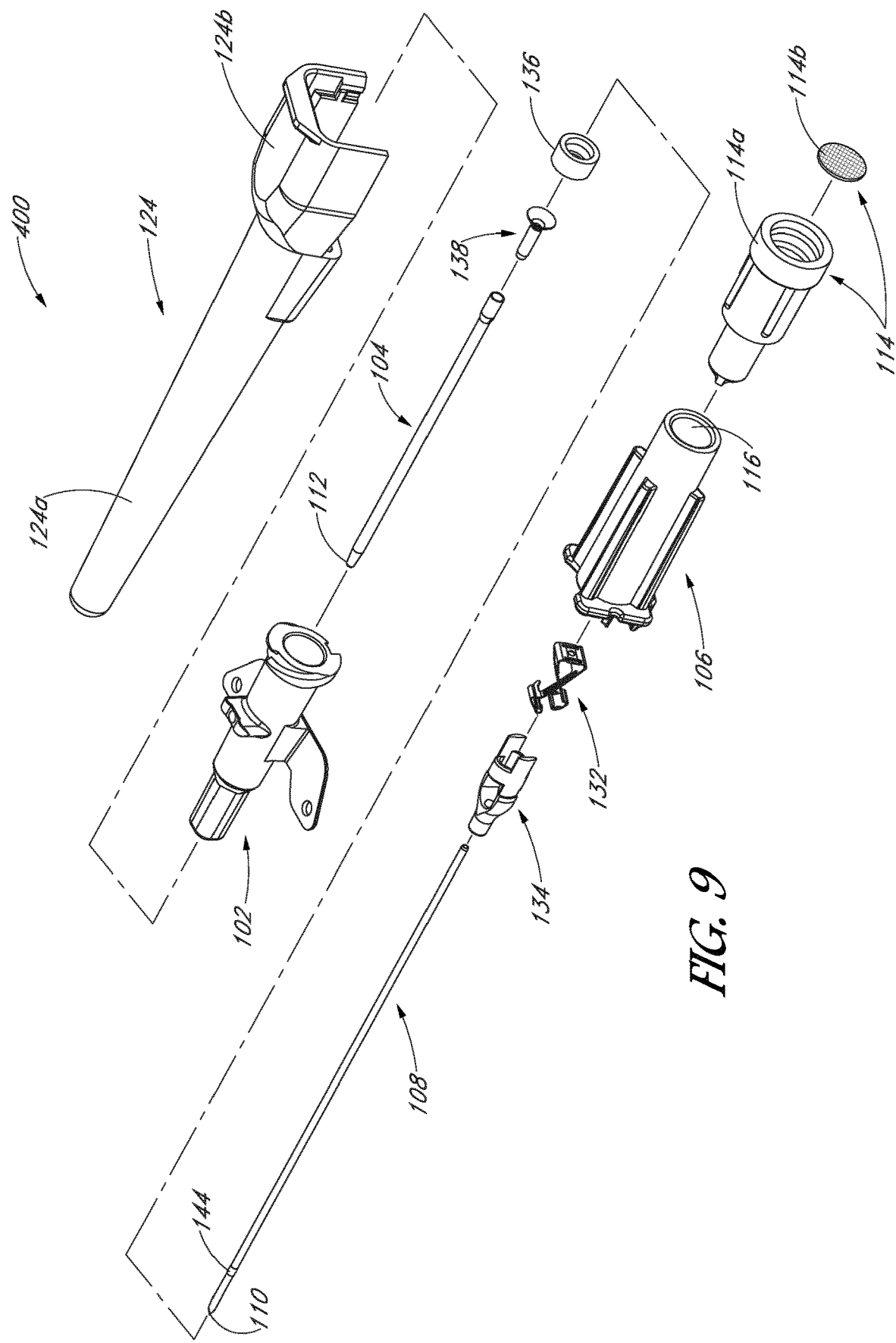
FIG. 9 is an exploded perspective of a needle assembly in accordance with further aspects of the present disclosure.

FIG. 9 is an exploded, perspective top view of a catheter assembly 400 provided in accordance with further aspects of the present disclosure. As shown in FIG. 9, the catheter assembly 400, which may more broadly be referred to as a needle assembly or a needle device, is shown comprising, a catheter hub 102 with a catheter tube 104 and a bushing 138. The bushing 138 can be configured to wedge the proximal end of the catheter tube 104 against the interior wall surfaces of the catheter hub 102 to retain the catheter tube 104 to the catheter hub 102.

Interiorly of the catheter hub 102, a septum or valve 136, an actuator or valve opener 134 and a safety clip 132, such as a needle guard or tip protector, are provided. A needle 108, which has a change in profile 144, can be inserted through the proximal opening of the catheter hub 102 with the needle tip protruding from the distal opening 112 of the catheter tube in a ready to use position, as shown in FIG. 9A. A cannula hub or needle hub 106 can attach to the proximal end of the needle 108 and can contact the proximal end of the catheter hub 102 when assembled thereto in the ready to use position. The proximal opening of the catheter hub 102 can be sized with a female Luer taper, optionally with external threads, to engage with a male Luer tip in a Luer slip or a Luer lock.

The tip protector 132 is configured to be removed with the needle 108 following use and the valve 136 and valve actuator 134 remain with the catheter hub 102 for controlling fluid flow therethrough. The actuator 134 is configured to be pushed distally by a male tip into the valve 136 to open the valve for fluid flow, as further discussed below.

A flash back plug or blood stopper assembly 114 can be connected to the needle hub 106 to stop blood flow out the flashback chamber 116 of the needle hub 106. The flash back plug 114 can be provided at the proximal end the needle hub 106 to allow air to vent but stops blood from spilling out the proximal end of the body of the flash back plug 114, which has a chamber 114a and a hydrophobic filter 114b is assembled in the chamber. Alternatively, a syringe can be attached to the proximal end of the needle hub 106. A second valve 136 and actuator 134 described further below can also be placed within the needle hub 106.

A protective cap 124 with a sleeve 124a and a saddle 124b can be provided to cover the needle 108 during packaging and before use, which is conventional. The saddle 124b can surround at least part of the catheter hub 102 and the needle hub 106 and be removably engaged to the needle hub.

FIG. 9A is an isometric cut-away view of the needle assembly 400 of FIG. 9 in an assembled state. The catheter hub 102 is shown with an optional pair of wings 126 extending radially of the hub body. When incorporated, the wings 126 can add stability by providing an increased surface area for resting and securing the catheter hub 102 against the skins of a patient, such as following intravenous access.

FIG. 9B is an isometric view of the assembled needle assembly 400 of FIG. 9, showing the removable cap 124 disposed over the needle and engaging the needle hub 106.

The catheter assembly 400 of the present disclosure is similar to the catheter assembly 100 of FIG. 1 with a few exceptions. With reference to FIG. 10A, a schematic cross-sectional side view of the catheter assembly 400 of FIG. 9 is shown. The catheter assembly 400 comprises the catheter hub 102 with the catheter tube 104 (partially shown) extending out a distal end thereof and the needle 108 attached to the needle hub 106 (partially shown) and the needle projecting through the catheter hub 102 and the catheter tube 104 in the ready to use position.

In the ready position with the needle hub 106 in contact with the catheter hub 102 and the needle tip extending out the distal end or distal opening 112 (of FIG. 9) of the catheter tube 104, the catheter assembly 400 is ready for use, such as to perform a venipuncture or intravenous access. Normally a protective cap (not shown) is removed from the catheter assembly or needle assembly 400 before the device is seen as depicted in FIG. 10A.

Located internally of the catheter hub 102 is the valve 136 having a valve body 320 with an outer perimeter, a valve disc 410 and a valve skirt 412 extending in an axial direction from the valve disc. In an example, the valve disc 410 comprises one or more slits defining one or more flaps to be opened/closed by the valve actuator 134. The type of slits and flaps and the numbers of each incorporated with the valve disc 410 can resemble those shown with the different valve embodiments 136 of FIGS. 8A-8C. In an embodiment, the valve skirt 412 is positioned in a recessed section 420 formed in the interior cavity 130 of the catheter hub 102, which prevents the valve 136 from axially moving once situated inside the catheter hub 102.

In an example, the recessed section 420 has a distal shoulder 420a and a proximal shoulder 420b (FIG. 10B) defining a groove therebetween. The valve skirt 412 has a length that is sized and shaped to fit within the groove. In an example, the valve skirt 412 contacts the proximal shoulder 420b while the valve disc 410 contacts the distal shoulder 420a. Viewed differently, the valve 136 of FIG. 10A can contact the distal shoulder 420a and the proximal shoulder 420b of the recessed section 420 and be restrained thereby in the ready to use position so that the valve skirt 412 is axially fixed or not axially movable.

In an example, the outer diameter or exterior surfaced of the skirt section 412 forms a snug fit or size-on-size fit with the recessed section 420 of the interior 130 of the catheter hub 102. In other examples, a slight inference fit is provided between the two. In still other examples, a small clearance is provided between the exterior surface of the skirt section 412 and the interior surface at the recessed section 420 with the valve skirt 412 in contact with the proximal shoulder 420b and the valve disc 410 in contact the distal shoulder 420a of the recessed section.

A distal cavity chamber 130a is provided distal of the valve disc 410 and proximal of the bushing 438. In some examples, a helical spring or a resilient biasing element, such as an elastomeric ring or cylinder, may be provided in the distal cavity chamber 130a, concentric with the needle, to bias the flaps of the valve disc 410 to assist the valve disc to close the one or more slits, similar to the resilient element 276 of FIGS. 1-4.

In an example, the valve disc 410 comprises a valve diameter, a valve thickness measured orthogonal to the valve diameter, and one or more slits defining two or more flaps, as previously discussed. In the illustrated embodiment, the valve skirt 412 extends axially to the lengthwise axis of the valve and has an elongated wall that is generally perpendicular to the outer perimeter of the valve disk 410, forming a generally cylindrical valve body. In some embodiments, the valve skirt 412 may be sloped such that the valve forms a frusto-conical structure.

The valve skirt 412 defines a valve cavity 424 having an open proximal end 426 through which the actuator nose or nose section 430 of the valve actuator 134 can advance and actuate the valve flaps of the valve disc 410. In one embodiment, at least some part of the actuator nose 430 including the distal actuation end 436 of the valve actuator 134 is located inside the valve cavity 424 of the valve 136 prior to actuation. Thus, the actuator nose 430 can be narrower than the inside diameter of the valve skirt 412 so that the actuation end 436 fits within the valve cavity 424 and abuts or touches the valve disc in the ready to use position. In an example, the relative dimensions are such that the nose section 430 of the actuator does not touch the interior wall surface of the skirt section 412 with some touching contemplated.

In an example, the actuation end 436 contacts the proximally facing surface of the valve disc 410 in the ready to use position and another part of the valve actuator 134, such as one or two projections 442 (FIG. 10B), abuts a shoulder 452 inside the catheter hub to impart a load on the valve disc in a ready to use position but not enough to open the one or more slits, as further discussed below. In other examples, the actuation end 436 is spaced from the proximally facing surface of the valve disc 410 in the ready to use position and the projection or projections 442 on the actuator either contact the shoulder 452 or are also spaced from the shoulder 452. When the one or more projections on the actuator 134 are spaced from the shoulder 452 and the actuation end 436 is spaced from the valve disc 410, the actuator can float within the catheter hub by a small amount in the axial direction.

In an example, the valve actuator 134 comprises a nose section 430, which is elongated in structure and can be generally cylindrical or have a draft angle or taper that terminates in an actuation end 436. The actuation end 436 can have a blunt distal end surface or has a sharp edge. The nose section 430 can have a wall surface with a continuous circumference or continuous perimeter section, without a gap or slit, such as a cylinder with a continuous wall. The nose section 430 can define a bore. In some examples, a plurality of spaced apart slits and/or openings can be provided on the nose section 430 to permit flow or fluid flushing.

Two actuating elements or plunger elements 152 can extend proximally of the nose section 430. For example, the two plunger elements 152 can be unitarily formed with the nose section 430 and can extend from the nose section in the proximal direction. A gap or space can be provided between the two plunger elements 152 for positioning the needle guard or tip protector 132 therebetween. In other words, the two plunger elements 152 each comprises at least two lengthwise edges and the edges are spaced from one another. The lengthwise edges of the plunger elements 152 can align with a lengthwise axis of the valve opener.

In an example, a projection 442 extends outwardly from an outer surface of one or both plunger elements 152. As shown, a projection 442 extends from the outer surface of each plunger element 152. Each projection 442 resembles a ramp surface having a generally flat edge for abutting the shoulder 452. The ramp surface of the projection 442 and the direction of the ramp allows the actuator 134 to be inserted into the interior of the catheter hub and be seated within the second recessed section 450, as further discussed below.

In an example, a transition section 440 extends from the nose section 430 and widens axially in the proximal direction. The two actuating elements 152 can extend from the transition section 440. The two actuating elements can extend from the nose section. Some embodiments may utilize other shapes for the nose section 430, such as cuboid, rectangular, conical, pyramidal, chamfered or the like.

In an example, the actuator or valve opener 134 has a lengthwise axis, the one or more actuating elements 152 extend axially or parallel to the lengthwise axis. In a particular example, two actuating elements 152 are diametrically opposed to one another along the lengthwise axis. As shown, the two actuating elements 152 define an outer diameter having a dimension that is larger than the diameter of the nose section 430.

In an example, the actuating elements 152 are flexible and deflectable so that when pushed by a male Luer tip, the actuating elements defect or flex. The actuating elements are deflectable by selecting a material that has the requisite resilient properties. In other examples, the actuating elements are deflectable by incorporating one or more weakened sections, such as by incorporating a structurally thin section, by incorporating cut-outs, by employing a small cross-section compared to other sections of the same elongated actuating element, or combinations thereof. Alternatively, the actuating elements 152 can be flexible and deflectable by selecting a material that has the requisite resilient properties and by incorporating one or more weakened sections.

In still other examples, each actuating element 152 has more than one different cross-sectional profiles or contour along a length section. For example, an elongated plunger element can have a square profile located adjacent a crescent-shaped profile.

In an example, the actuating elements 152 are rigid and not deflectable or deformable when loaded, such as when pushed, by a male Luer tip. Further, stabilizing elements may be incorporated to increase the rigidity of the two actuating elements 152. The two actuating elements 152 may each include a cross-sectional profile, at least at a proximal end, that overlaps a push end of a male tip so that the male tip can push the valve actuator into the valve, as previously discussed with reference to FIGS. 5C and 5D.

The nose section 430 of the valve actuator 134 can be configured to engage the valve 136 to open the valve disc 410 when an axial force is applied by a male tip to the actuating elements 152 towards the distal end of the catheter assembly 100, such as during the insertion of an IV drip line male Luer connector. Generally, the nose section 430 is rigid relative to the more pliable valve 136, which allows the nose section 430, and more specifically the actuation end 436, to actuate the valve 136, such as to deflect the one or more flaps and open the one or more slits on the valve disc 410. The nose section 430 may be made of a non-compressible material, such as metal, a rigid plastic, or a hard elastomer for pushing against and opening the valve.

The illustrated valve actuator embodiment 134 includes a pair of opposed bands or stabilizers 444, 444 (collectively or individually referred to as stabilizer or stabilizers 444) connecting the two actuating elements 152 at a location along the length of the actuating elements that are between the nose section 133 and the proximal end of the actuating elements. In some examples, the stabilizers 444 can be located at the proximal end of the two actuating elements 152 so that proximal edges of the stabilizers 444 are generally flush with the proximal end surfaces of the actuating elements. The two stabilizer elements 444, 444 can be referred to as a first or upper stabilizer element and a second or lower stabilizer element.

In one embodiment, the stabilizers or stabilizer elements 444, 444 are arc-shaped, forming an arc following the interior profile of the catheter hub 102 and connecting one actuating element 152 to another actuating element 152. The stabilizers or stabilizer elements 444 may form a substantially cylindrical section on the body of the valve actuator, which body is spaced apart from the nose section 430 of the valve actuator. In other words, the valve actuator can be elongated and can have sections that are continuous along a radial direction and sections with reliefs or through passages through the wall of the actuator that are not continuous along the radial direction.

In an example, the stabilizers 444 define a continuous body section along a perimeter or radial direction of the valve actuator that is spaced from a continuous body section of the nose section 430, which is also continuous along a perimeter or radial direction. The two stabilizers or stabilizer elements 444, 444 may be joined together with the two plunger elements 152 to form a ring structure. Optionally, the two stabilizer may be slightly offset and angled from each other, as shown in FIG. 10a. In some embodiments, there may be one, three, or a different number of actuating elements 152 or stabilizers 444. In an example, the valve actuator 134, with the stabilizers or stabilizer elements 444 and projections 442, is made from plastic, such as by plastic injection molding.

The stabilizers 444 can help the valve actuator 134 remain centered within the catheter hub 102 while the actuator moves, such as when pushed by a male Luer tip. By staying centered, the nose section 430 can be better aligned with the valve disc 410, such as the slits on the valve disc, allowing for smooth actuation of the valve 136. The stabilizers 444 can also provide an engagement, via friction, with the interior of the catheter hub 102 to prevent the actuator 134 from sliding in the proximal direction following removal of the male Luer tip.

In one embodiment, the nose section 430 is configured to remain engaged to the valve disc 410 following actuation of the valve and following removal of the male Luer tip. For example, the nose section 430 can wedge between the one or more slits on the valve disc and be held there by friction, as further discussed below. Surface features, such as bumps, grooves, or barbs, can be provided on the valve actuator 134, such as on the nose section, to maintain the engagement between the actuator and the valve following actuation and following removal of the male Luer tip.

A relief, opening, or through passage 448 is provided between the transition section 440, or from the nose section, and each of the two stabilizers 444, 444. The two reliefs or through passages 448 provide clearance so that the interior or central part of the valve actuator 134 and the interior surface of the catheter hub 102 can be in open communication. In other words, between the continuous section of the nose section and the continuous perimeter section defined by the two stabilizers 444, 444 and the plunger elements 152, call a stabilizing ring or stabilizing ring 456 (FIG. 12A), are one or two reliefs, through passages, or openings 448.

The stabilizing ring 456 of the valve actuator 134 can have an inside diameter that is smaller than the diameter defined by the diagonal section or elbows 304 of the two arms 288, 290 of the needle guard 132 when the two arms are biased outwardly by the side of the needle shaft. Thus, during installation of the needle guard 132 into the holding space of the valve actuator 134, the diagonal section or elbows of needle guard 132 can deflect to pass through the stabilizing ring 456 and into the open areas defined by the reliefs 448.

When the tip protector 132 is positioned between the two plunger elements 152, the two distal walls 300, 302 (FIG. 7) of the needle guard 132, more specifically the two diagonal sections or elbows 304, can be located in the reliefs 448 as discussed above to engage the guard engagement surface on the interior surface of the catheter hub 102. This allows the needle guard 132 to project from the holding space of the valve actuator 134 through the two reliefs 448 to engage with the guard engagement surface of the catheter hub. The needle guard can therefore be retained within the interior of the catheter hub in the ready to use position and during retraction of the needle following successful venipuncture until the needle tip moves proximal of the two distal walls on the needle guard, at which time the needle guard can close over the needle tip and be removed with the needle as discussed above with reference to FIG. 3.

A second undercut or recessed section 450 proximal of the first recessed section 420 can be provided in the interior cavity of the catheter hub 102 for accommodating the two diagonal sections or elbows 304. The needle guard 132 can therefore be prevented from sliding in the proximal direction during retraction of the needle following successful venipuncture by a shoulder 452 of the second recessed section 450 or by some other surface feature on the interior of the catheter hub, such as a guard engagement surface on the interior of the catheter hub. Optionally or alternatively, the distal edge 446a (FIG. 12B) of one or both stabilizers 444, 444 can provide the restraining surface to prevent the needle guard 132 from early activation during retraction of the needle, prior to the needle tip moving proximally of the two distal walls 300, 302. In addition to the distal edge 446a, both stabilizers 444, 444 also have a proximal edge 446b.

In some examples, one or both stabilizer elements 444, 444 can have a slit or a channel, thus dividing that arc-shaped stabilizing element into two segments, similar to the stabilizer elements of FIGS. 16A-16C. Nonetheless, even with a slit on one or both stabilizer elements 444, 444, the stabilizing ring 456, which can be a non-continuous ring, similar to a ring with one or more slots formed through the ring, can still provide the restraining surface to prevent the needle guard 132 from early activation during retraction of the needle, prior to the needle tip moving proximally of the two distal walls 300, 302 (FIG. 7). The restraining surface can also be referred to as a restrict point, choke gap, or choke point since it provides a rigid structure that prevents the needle guard from moving proximally thereof unless or until the needle guard first activates and collapses radially to reduce its radial profile to then slip proximally of the choke point. In an example, one or two elbows 304 (FIG. 7) of the needle guard can be restricted by the choke point from moving in the proximal direction until the one or two elbows of the needle guard deflect to reduce needle guard's radial profile. In an example, when the radial profile of the needle guard is reduced, the needle guard can slip through the bore defined by the stabilizing ring, from a distal position of the stabilizing ring to a proximal position of the stabilizing ring.

With further reference to FIG. 10B, which is the top cross sectional view of the same catheter assembly 400 of FIG. 10A rotated 90 degrees from the FIG. 10A view, with the tip protector 132 shown fitting between the actuating elements 152. In an embodiment, one or more actuating elements 152 are sized and shaped for contact by a male Luer to transfer a distally directed force from the male Luer, through the nose 430 to then open the valve 136, as previously discussed.

The valve opener 134 can be made from a metal material or from a plastic material. When made from a metal material, the valve opener 134 can be formed by bending or deep draw methods and the arc shape cross section of the actuating element 152 can provide added rigidity when pushed by the male Luer. Each actuating element 152 can comprise at least two lengthwise edges and a rib can be provided along one or both of the lengthwise edges to further add structural rigidity. One or more gaps can be provided between any two actuating elements 152. The gaps can provide clearance or space for fluid flow flowing thereacross, such as during flushing blood or IV infusion. The gap between the actuating elements 152 can define a holding space to accommodate a tip protector 132, as shown in FIG. 10B.

In some embodiments, a majority or most if not all of the tip protector 132 fits within a holding space formed by the body of the actuator 134, between the two plunger elements 152, in the ready to use position, as shown in FIG. 10B. This allows the catheter hub 102 to be more compact, as less longitudinal space is needed within the hub to fit both the actuator 134 and the tip protector 132 serially lengthwise or when the two only partially overlap in the axial direction. In FIG. 10B, the tip protector 132 is shown fitting completely within the holding space of the actuator 134 to further reduce the needed space or length in the catheter hub. As shown, the proximal wall 280 of the needle guard 132 is generally flush or even with the proximal end surfaces of the two plunger elements 152.

When the tip protector 132 only engages with the distal edge 446a of the relief or through passage 448 in the actuator, then no deformity or change of diameter is required on the inside wall of the catheter hub and the tip protector 132 can be placed further proximally in the female Luer taper section while complying with the international Luer standard for conical fittings and the overall length of the catheter hub 102 can be further reduced.

FIG. 11 is a perspective view of the catheter assembly 400 of FIGS. 10A and 10B. The relief or through passage 448 is clearly shown proximal to the nose section 430 of the actuator 134 to allow the tip protector 132 to engage with the interior of the catheter hub 102, as previously discussed. Proximal to the relief 448, a stabilizer 444 can be seen to provide additional rigidity and/or a greater engagement surface for the catheter hub 102. The actuating elements 152 extend past the proximal edge 446b (FIGS. 12A and 12B) of the stabilizer 444 to substantially the same distance as the proximal wall 280 of the tip protector 132. In the illustrated embodiment, the tip protector 132 substantially fits within the holding space of the actuator 134 and the proximal wall 280 of the tip protector is approximately even with the proximal ends of the actuating elements 152, in the axial direction.

FIG. 12A is a partial cross-sectional side view of the valve assembly 400 after the needle and needle guard have been removed from the catheter hub 102, such as following a successful venipuncture. As shown, the valve 136 is in a closed position in which the one or more slits 324 of the valve disc 410 are closed. Also shown is the valve actuator 134 retracted position in which the actuation end 436 of the nose section 430 is not pushed into and opening the one or more slits. This position is also understood to be the valve pre-activated position. That is, a male Luer tip has not been inserted into the proximal opening of the catheter hub to advance the valve actuator to open the valve. In other words this is the valve closed position.

FIG. 12B is a partial cross-sectional side view of the valve assembly 400 of FIG. 12A in which the valve has been actuated to open the one or more slits 324. The present view shows the valve actuator 134 advanced distally into the valve 136 by a syringe tip or a Luer tip of an IV drip line (not shown) to permit fluid flow through the catheter hub. Advancing the actuator 134 causes the actuation end 436 to advance against the valve disc 410 and deflecting the flaps radially and distally to open a fluid path to be formed through the catheter assembly 400.

When initially inserting the male medical implement, such as a male Luer tip, into the proximal opening of the catheter hub 102, the male tip initially contacts the two actuating elements 152 on the actuator 134 to advance a distally directed force on the two actuating elements 152 to open the valve 136. The distally directed force moves the actuator 134 in the distal direction until the geometries of the male tip and the proximal opening of the catheter hub stop further distal advancement of the male tip. In an example, a female Luer taper of the catheter hub 102 and a male Luer taper of the male tip mate and block distal advancement of the male tip further into the opening of the catheter hub. A seal is provided by the Luer engagement to prevent fluid from leaking out the proximal opening of the catheter hub.

As the actuator 134 moves distally by the distal advancement of the male tip, the nose 430 of the valve actuator 134 is urged distally and pushes against the proximally facing surface of the valve disc 410. In particular, the nose of the actuator 134 initially pushes against the proximally facing surface of the valve disc 410 and since the valve is axially fixed within the first recessed section 420 of the catheter hub, the one or more flaps on the valve disc 410 deflect radially and in the distal direction. Fluid from the male tip can then flow through the catheter hub 102, through the valve 136, and through the lumen of the catheter tube 104.

Alternatively, a suction can be applied by the male medical instrument, such as a syringe or vacuum blood collection tube, and blood aspirated from the patient. This is often done for testing samples before infusion therapy is commenced. Also, typically any remaining blood is first flushed from the inside of the catheter hub 102 before infusion therapy is commenced.

With continued reference to FIG. 12B, the actuation end 436 of the nose section 430 is shown projected through the valve disc 410 and either contacts or is just about to contact the bushing 138 in the valve actuated position. In this configuration, even after removal of the male tip, the valve actuator 134 remains engaged to the valve 136. That is, the friction between the valve actuator 134 and the valve disc 410 exceeds the restoring forces produced by the valve flaps in attempting to return to its un-deformed position shown in FIG. 12A. This activated position can be considered a one-time use or one-time actuation since the valve actuator 134 and valve 136 do not return to the pre-activation position of FIG. 12A when the male tip is removed.

In an alternative embodiment, the nose section 430 is configured so that when pushed into the valve 136 during activation, the actuation or activation end 436 does not extend distally past the flaps of the valve disc 410. This configuration can ensure that the valve actuator 134 is pushed back by the flaps of the valve disc when the male Luer implement is removed. A conical configuration at the distal end of the actuator 134 can be such a configuration, which maintains a proximally directed force vector, which is greater than a perpendicular force vector. The angle of the cone can be designed to provide the necessary force vectors when the actuator 134 has reached it maximum distal movement and its minimum distal movement. The difference between the maximum movement and minimum movement of a standard Luer connector is approximately 2.5 millimeters.

Additionally, a spring or an elastic element or ring, similar to the resilient element 276 of FIG. 1, can be incorporated at the distal cavity chamber 130a to increase the re-coil or returning forces of the valve 136 to facilitate pushing the valve actuator 134 in the proximal direction following removal of the male tip to return to the pre-activated position or valve closed position shown in FIG. 12A. The elastic element can also help to close the flaps of the valve disc 410. In this manner, the valve 136 and valve actuator 134 can be re-closed after the initial activation and re-open and so forth, repeatedly. Alternatively or additionally, the flaps 326 on the valve disc can be made thicker to provide enough restoring force without the need for an elastic element.

With reference again to the stabilizing ring 456 of FIGS. 12A and 12B, note that the distal edge 446a and the proximal edge 446b on the stabilizers 444, 444 are not parallel to the proximal edge of the two plunger elements 152. Instead, the distal edge 446a and the proximal edge 446b of the upper stabilizer 444 are parallel to each other and the distal edge 446a and the proximal edge 446b of the lower stabilizer 444 are parallel to each other but the corresponding edges of the upper and lower stabilizers 444, 444 are not parallel to one another. Said differently, the upper stabilizer 444 has a distal tilt while the lower stabilizer 444 has a proximal tilt.

Figure 13B:
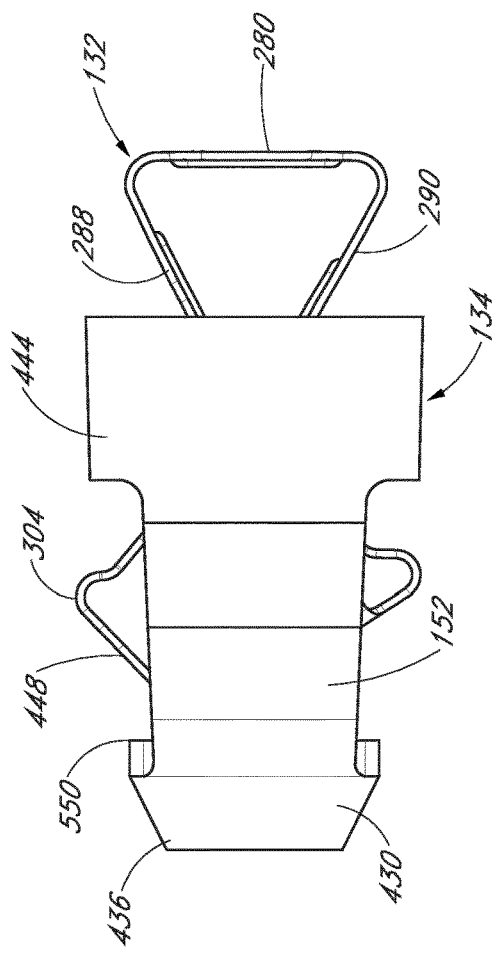
FIGS. 13B and 13C show different views of the valve opener of FIG. 13A with a needle guard located in a holding space of the valve opener.
Figure 13C:
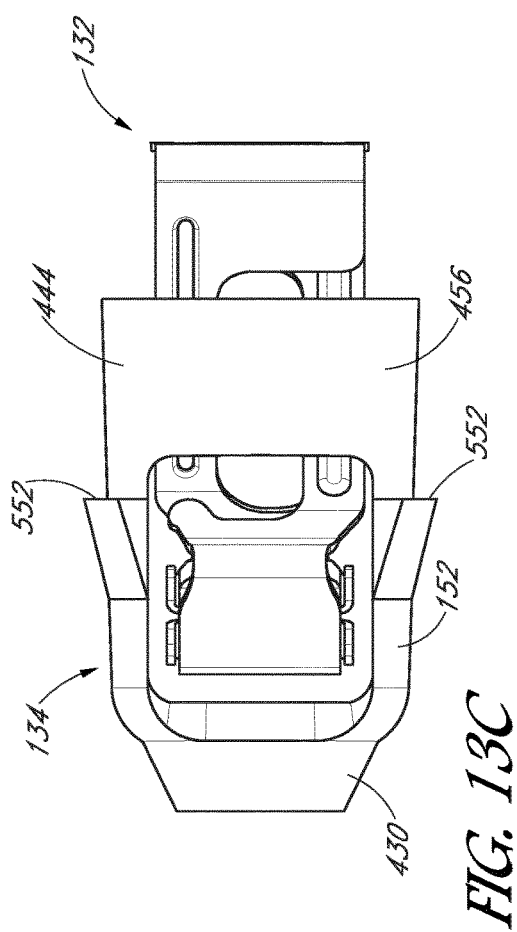
Figure 13A:
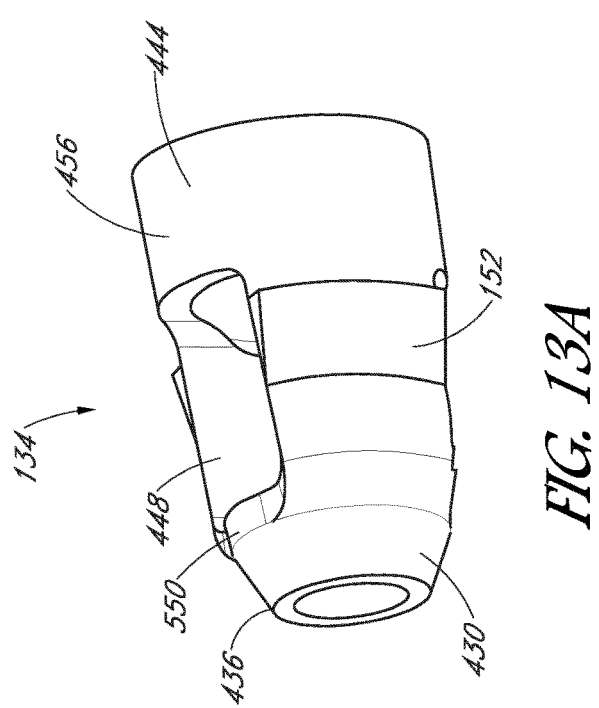
FIG. 13A is a perspective view of a valve opener provided in accordance with further aspects of the present disclosure.

FIG. 13A is a perspective view of a valve actuator 134 embodiment provided in accordance to further aspects of the present disclosure. The actuator 134 comprises a generally cylindrical nose or nose section 430, such as a conical frustum shape nose, and an activation end 436 at a distal end thereof. Actuating arms 152 extend lengthwise from the nose section 430. The valve actuator 134 provides similar functionally as the actuator 134 of FIGS. 1-4 and 10A-12B, with some structural differences, such as the stabilizers 444 being generally even without off-setting edges. In the ready position and if used with the catheter assembly of FIGS. 10A and 10B, the nose section 430 may be in contact with the valve disc or can be slightly spaced from the proximal surface of the valve disc 410.

A relief or through passage 448 provides access for a tip protector 132 to engage with the interior of the catheter hub 102, as previously described. In one embodiment, two through passages or reliefs 448 on opposite sides of the body of the actuator 134 are provided to give access to the interior of the catheter hub 102 to two corresponding arms of a tip protector 132. Other embodiments can have a different number of through passages, such as one, three or more, can be incorporated. For example, there may be three through passages spaced between three actuating elements. The distal end of the relief or through passage 448 forms an engagement shoulder 550 for a valve arm, which is discussed in further detail in FIGS. 14B and 14C.

In the illustrated embodiment, the stabilizers 444 connect the two actuating elements 152 and form a ring structure on the proximal end of the actuator 134, also called a stabilizing ring 456. The stabilizers 444 can provide additional rigidity and/or engagement surfaces for the actuator to interact with a needle guard and/or with the interior of the catheter hub 102. In some embodiments, the stabilizing ring 456 comprises one, two, or more individual sections that form a substantially cylindrical section of the actuator body. The stabilizers can have edges that align with each other or may be offset, such as shown in the embodiment of FIG. 10A.

FIGS. 13B and 13C illustrate a side and top view of the actuator embodiment 134 of FIG. 13A. A majority of the tip protector 132 is shown fitted inside the holding space of the actuator 134, with a portion of the tip protector extending in the proximal direction past the proximal end of the actuator. For example, the proximal wall 280 and part of the two arms 288, 290 of the tip protector 132 extend radially through the relief 448 of the actuator 134. One or more ribs or projections 552 can be formed on the exterior surface of the actuating arms 152 and can engage with a shoulder 452 on the second recessed section 450 (FIG. 10A) of the catheter hub to retain the actuator 134 inside the catheter hub 102 in the ready to use position and used position.

Figure 14C:
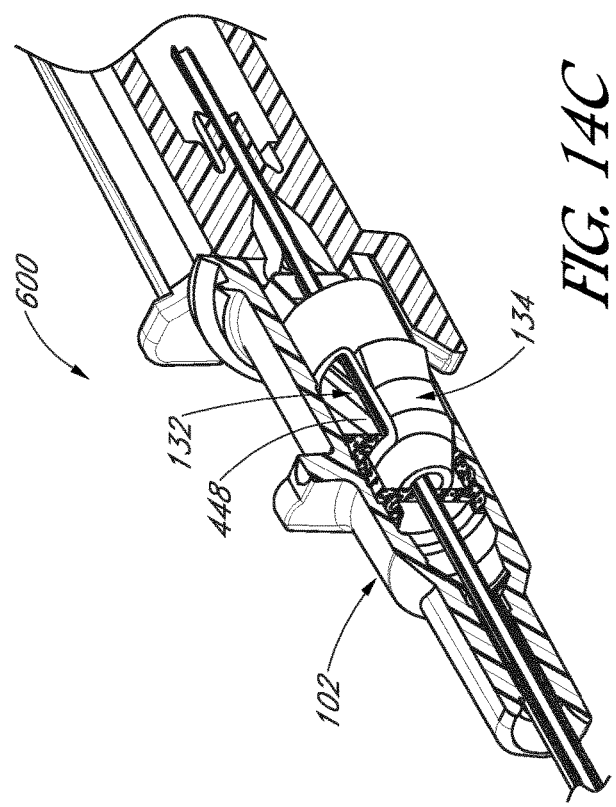
FIG. 14C is a partial perspective cut-away view of the needle assembly of FIG. 14B.
Figure 14A:
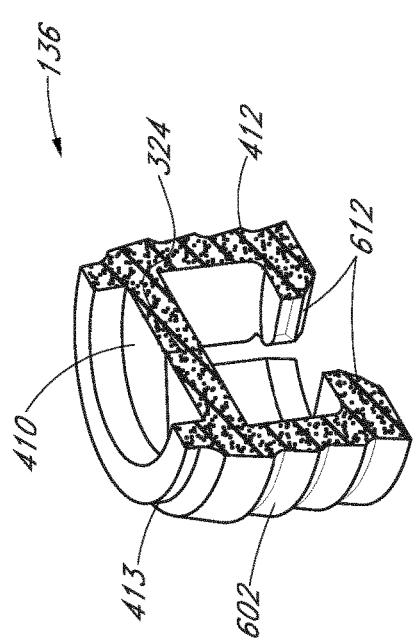
FIG. 14A shows a valve with a valve disc and a valve skirt in accordance with further aspects of the present disclosure.
Figure 14B:
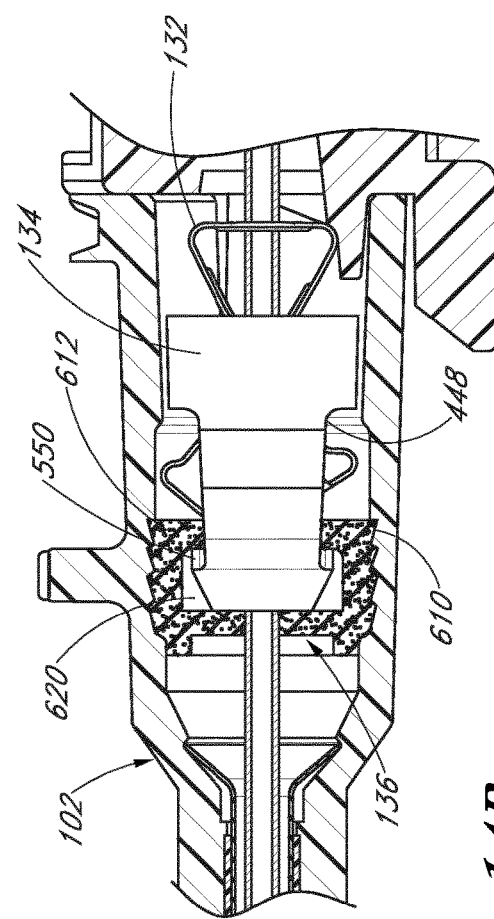
FIG. 14B is a partial side cut-away view of a needle assembly with the valve of FIG. 14A located inside the interior of a catheter hub.

FIG. 14A illustrates a valve embodiment 136 having one or more ridges 602 formed on the outer surface of the valve skirt 412. FIG. 14B illustrates the valve 136 of FIG. 14A, connected to the actuator 134 of FIGS. 13A-13C, while in a ready position in a catheter hub 102.

The valve 136 of FIG. 14A performs a similar function as the valve 136 of FIGS. 1, 10A-10B, and 12A-12B and has many of the same structures, such as a skirt, 412, a valve disc 410, and valve slit 324. The valve 136 further includes a distal skirt section 413 extending distally of the valve disc 410. In addition, an engagement surface 602, such as one or more ridges, is formed on the outer surface to provide greater engagement with the catheter hub 102, as shown in FIG. 14B.

The engagement surface 602 can comprise a projection or a groove or a combination of both a groove and a projection formed on the exterior surface of the valve 136. For example, the engagement surface 602 may comprise a section having a first outer diameter (e.g., peak/projection) and a second outer diameter (e.g., valley/groove), with the sections repeated one or more times on the outer perimeter of the valve. In another example, the grooves and/or projections may be formed as a single continuous, spiral structure on the exterior of the valve.

In some embodiments, the engagement surface 602 extends circumferentially along the outer surface of the valve 136, forming rings or a spiral thread. In other embodiments, the engagement surface 602 comprises several separate sections formed on the outer surface, such as separate protrusions/recesses or the thread sections on an interrupted screw.

The catheter hub 102 may be provided with a corresponding engagement surface 610 on the interior surface of the catheter hub to mate with the valve engagement surface 602 of the valve 136. The engagement surface 610 can be similar to the engagement surface 602 of the valve 136, but with inverse features in order to mate with the valve engagement surface 610.

By forming engagement surfaces on the valve 136 and the catheter hub 102, the valve can be better retained in the correct position in the catheter hub 102, even as the actuator 134 applies force to the valve 136. The valve 136, with the engagement surface 602, can be axially fixed within the catheter hub without a recessed section having proximal and distal shoulders.

In the illustrated embodiment, two engagement arms 612 are formed on the proximal end of the valve 136, extending radially inwards from the interior surface of the valve skirt 412. The engagement arms 612 are configured to mate with the engagement shoulders 550 formed on the actuator 134. In the illustrated embodiment, two opposing engagement shoulders 550 are configured to engage with the two engagement shoulders 550 formed by the two reliefs or through passages 448 in the actuator 134. In other embodiments, different numbers of engagement shoulders and engagement arms may be used (e.g., one, three, or more).

Referring to FIG. 14B, in a ready position, the nose 430 of the actuator 134 lies within a holding space 620 of the valve 136, adjacent to the proximal surface of the valve disc 410. The valve skirt 412 surrounds the nose 430, with the engagement arms 612 partially extending into the reliefs or through passages 448 of the actuator and engaging with the engagement shoulders 550. In one embodiment, the engagement arms 612 have a sufficiently low profile to not interfere with the needle and the tip protector 132, such that the arms 612 do not interfere with the movement of the needle and the tip protector 132.

FIG. 14C is a perspective cut-away view of the needle assembly of FIG. 14B.

The valve 136 of the catheter assembly 600 of FIGS. 14B and 14C may be configured as a one-time or single actuation use. Optionally, the valve disc 410 of the valve 136 may be made sufficiently resilient such as by making the flaps thicker so as to return to its closed position after a male Luer tip is removed and an axial load is no longer applied to the valve actuator. In another example, an elastic element, similar to resilient element 276 of FIG. 1, may be incorporated to assist with closing the flaps on the valve. The actuator has a conical nose, which is preferred for a multi-use valve design. The conical shape when not pushed further than the distal ends of the open flaps will retain a proximally directed force vector of the flap against the conical surface, which can push the actuator back to its starting position until the flaps are closed again and flow is stopped.

With reference now to FIG. 15A, a top or plan view of a valve opener or actuator 134 is shown. The valve opener can be used with any needle assembly described elsewhere herein, such as shown in FIGS. 9-12B. As shown, the valve actuator has a nose section 430, a transition section 440, and two plunger elements 152 extending proximally of the transition section, or proximally from the nose section. The nose section 430 defines a first continuous perimeter section 700. Other locations of the nose section 430, away from the first continuous perimeter section 700, can comprise a slit or a slot.

Two stabilizer elements 444, 444 are attached to the two plunger elements 152 to form a stabilizing ring 456, which defines a second continuous perimeter section 702 of the valve actuator. Each stabilizer element 444 can comprise two edges 446a, 446b. In an example, the two edges 446a, 446b of each stabilizer element can be parallel to one another. As shown, the two stabilizer elements 444, 444 are skewed or slanted so that while two edges 446a, 446b of each stabilizer element can be parallel to one another, the two edges 446a, 446b from one stabilizer element are not parallel to the two edges 446a, 446b of the other stabilizer element. As shown, the proximal edges 446b of the two stabilizer elements 444, 444 are offset along an axial direction or lengthwise direction of the valve actuator. As shown, the distal edges 446a of the two stabilizer elements 444, 444 are offset along an axial direction.

Two reliefs or two through passages 448 are provided on the valve opener 134, each defined or bounded by the transition section 440, the two plunger elements 152, and the respective stabilizer elements 444, 444. The two reliefs or through passages may be referred to as a first relief or first through passage and a second relief or second through passage. In an example, each relief or through passage has a perimeter 708. In an example, each perimeter can be defined by the structure of the transition section 440, the two plunger elements 152, and the respective stabilizer elements 444, 444. As the two stabilizer elements 444, 444 can skew or slant in different directions, the two perimeters 708 of the two reliefs or through passages 448 can be different, such as having different perimeter contours or shapes. As shown, the two perimeters 708 are each defined by a continuous loop. In other words, in the present embodiment, the perimeters 708 do not have a slit or a slot to form an open perimeter. However, where a stabilizer element 444 includes a slot or a slit, the perimeter can be an open perimeter or a non-continuous perimeter.

In some examples, the two stabilizer elements 444, 444 can extend laterally without skewing or slanting in the distal direction or the proximal direction. When so configured, the edges 446a, 446b of the two stabilizer elements 444, 444 are parallel to one another. Additionally, the four edges of the two stabilizer elements can be parallel to one another and axially offset. That is, the proximal edge 446b of one stabilizer element can be located more proximally or distally that the proximal edge 446b of the other stabilizer element while the four edges are parallel to one another.

With further reference to FIG. 15A, two plunger element stubs or extensions 152a are shown extending proximally of the stabilizing ring 456. In an example the two plunger element stubs 152a can extend from the stabilizing ring 456 and axially align with the plunger elements 152 located distally of the stabilizing ring 456. In other examples, the two plunger element stubs 152a are not axially aligned with the two plunger elements 152 located distally of the stabilizing ring 456. In still other examples, only one plunger element stub 152a aligns with one of the two plunger elements 152. For a valve opener or actuator with only one plunger element 152 between the first and second continuous perimeter sections, only one of the two plunger element stubs 152a or none of the plunger element stubs can align with the one plunger element.

In some examples, there can be more than two plunger element stubs or extensions 152a extending proximally of the stabilizing ring 456. The two or more plunger element stubs or extensions 152a can be equally spaced around the proximal periphery of the stabilizing ring 456 or randomly spaced around the proximal periphery of the stabilizing ring 456. The plunger element stubs can extend the overall length of a valve actuator. The number of plunger element stubs and/or the arc-curve of each plunger element stub, which defines a width of each plunger element stub, can provide a greater overlapping surface with a male Luer tip than fewer numbers or for a plunger element stub with a relatively smaller arc-curve.

With still further reference to FIG. 15A, the two plunger elements 152 are each shown with at least two thicknesses to create a projection 442 at an interface between the two thicknesses on an outside surface 710 of each plunger element. As previously described, the two projections 442 can be located inside a recessed section 450 (FIG. 10B) so that a shoulder 452 at a proximal end of the recessed section 450 can provide a stop surface to prevent dislodgement of the valve opener 134 in the proximal direction. In some examples, only one projection 442 is employed on one of the two plunger elements to prevent dislodgement of the valve opener 134 in the proximal direction. In still other examples each plunger element 152 has a single thickness and the projection 442 is formed by adding material to the plunger element during injection molding at the site of the projection only.

In an example, a planar surface section 714 is provided with the valve actuator 134 on the same side of each stabilizer element 444. The planar surface section 714 originates from about the nose section 430 or the transition section 440 of the valve member and extends proximally to about the two projections 442.

With reference now to FIG. 15B, which is a cross-sectional side view of the valve opener 134 of FIG. 15A taken along lines 15B-15B, the two planar surface sections 714, one on each side of the valve opener 134 corresponding to the two stabilizer elements 444, are provided as a way to minimize the overall profile of the transition section 440 and the two plunger elements 152 along a side profile, as shown in 15B. Thus, in an example, the cross-sectional dimension of the nose section 430, of the transition section 440, and of the two plunger elements 152 are generally constant or be the same within typical manufacturing tolerances along a side view, or a 90 degree turn along the lengthwise axis of the valve opener from the orientation of FIG. 15A.

With continued reference to FIG. 15B, a holding space 720 is shown, which can be located between two plunger elements 152, inside the stabilizing ring 456, between two plunger element stubs 152a, or combinations thereof. As previously described, part or all of a needle guard or tip protector 132 can be located in the holding space 720 in a ready to use position and one or two elbows of the tip protector 132 projecting out the relief 448.

A proximal wall of a needle guard 132 can be flush with the proximal end surface 726 of a plunger element stub 152a, located proximally of the end surface 726, or located distally of the end surface. If no plunger element stub is incorporated, a proximal wall of a needle guard 132 can be flush with the proximal edge of one or both stabilizer elements 444, 444, located proximally of the proximal edge of one or both stabilizer elements 444, 444, or located distally of the proximal edge of one or both stabilizer elements 444, 444.

With still further reference to FIG. 15B, the distance between the two inside surfaces 728 of the two stabilizer elements 444, 444 define a choke gap, choke point, or restricting point for a needle guard to limit proximal movement of the needle guard in a ready to use position and/or during retraction of the needle following intravenous access, as previously discussed. That is, before the needle tip moves proximally of one or two distal blocking walls of a needle guard, the choke point or gap is too small for the needle guard to pass proximally of the choking point, choke point, or restricting point. However, after the needle tip moves proximally of one or two distal blocking walls of the needle guard, the two distal walls move radially inwardly to decrease the needle guard's radial profile, which is smaller than the choke point. At that point, with a smaller radial profile measured at two elbows, the needle guard can move proximally of the choke point.

FIG. 15C is a perspective view of the valve opener 134 of FIGS. 15A and 15B.

With reference now to FIG. 16A, a top or plan view of a valve opener or actuator 134 in accordance to an alternative aspect of the present disclosure is shown. The valve opener 134 can be used with any of the needle assemblies disclosed elsewhere herein. As shown, the valve actuator has a nose section 430, a transition section 440, and two plunger elements 152 extending proximally of the transition section 440. The nose section 430 defines a first continuous perimeter section 800. Other locations of the nose section 430, away from the first continuous perimeter section 800, can comprise a slit or a slot.

Two stabilizer elements 444, 444 (FIG. 16B) are attached to the two plunger elements 152 to form a stabilizing ring 456. However, each stabilizer element 444, 444 is non-continuous and has a slit or slot 804. Said differently, each stabilizer element 444 of the present embodiment comprises two stabilizer segments 810, 812 spaced from one another by a slit or slot 804. Each stabilizer segment 810 is further understood to include an inside edge 814 that is spaced from the other inside edge 814 of the other stabilizer segment 812. The two inside edges 814 define a slit or a slot 804 therebetween. The two stabilizer segments 810, 812 can be similar or the same or can be different.

The width of the slit or slot 804 is smaller than the widest width of the needle guard 132 (FIG. 7). In some examples, the width of the slit or slot 804 is smaller than the width of the distal walls 300, 302. The width of the slit or slot can also be smaller than the width of the needle guard at the elbows 304. The relative dimensions between the slit or slot 804 on the valve opener 134 and the width of the needle guard 132 are selected so that the stabilizing rings 456 are sized to limit proximal movement of the needle guard 132, such as the two elbows 304 on the needle guard, from moving proximally of the stabilizing ring during retraction of the needle but before activation of the needle guard. In other words, even with slits or slots incorporated with the two stabilizing rings, they can still act as restraining surfaces or choke points.

As noted previously, the valve opener 134 can incorporate one or two stabilizer elements 444. The one or two stabilizer elements 444 can also be continuous or be segmented having slits or slots 804 between the segments. A needle guard with one arm and one elbow, two arms but only one elbow, or two arms and two elbows can be used with any of the various valve actuators.

While the stabilizing ring 456 of the present valve embodiment comprises one or more slits, such as two slits 804, the stabilizing ring 456 provides similar restrictions or choke points along the two stabilizer elements 444, 444 for a needle guard or tip protector as other valve actuators 134 described elsewhere herein, and as further discussed below. The stabilizing ring 456, which has a non-continuous perimeter section, can also provide stability during axial movement of the valve actuator 134 by acting as a bearing to guide the valve actuator 134 against the interior surface of a catheter hub.

Each stabilizer element 444 can comprise two non-continuous edges 446a, 446b, which can be referred to as a distal edge 446a and a proximal edge 446b. In an example, the two edges 446a, 446b of each stabilizer element are parallel to one another. The two edges 446a, 446b from one stabilizer element 444 are also parallel to the two edges 446a, 446b of the other stabilizer element. As shown, the proximal edges 446b of the two stabilizer elements 444, 444 are aligned along an axial direction or lengthwise direction of the valve actuator. As shown, the distal edges 446a of the two stabilizer elements 444, 444 are also aligned along an axial direction. In other examples, the edges of the two stabilizer elements 444 can be offset axially.

Two reliefs or two through passages 448 are provided on the valve opener 134, each defined or bounded by the transition section 440, the two plunger elements 152, and the respective stabilizer elements 444, 444. The two reliefs or through passages 448 may be referred to as a first relief or first through passage and a second relief or second through passage. In an example, each relief or through passage has a perimeter 820. In an example, each perimeter 820 can be defined by the structure of the transition section 440, the two plunger elements 152, and the respective stabilizer elements 444, 444. The two perimeters 820 of the two reliefs or through passages 448 can be the same, as shown, or can have different perimeter contours or shapes. Because of the slits or slots 804, one on each stabilizer element 444, the two perimeters 820 are open, such as being non-continuous.

The valve opener 134 of the present embodiment can be made from a metal material. For example, a stamped metal sheet, such as a stamped stainless steel sheet, can be worked using deep draw methods to form the shape shown. The various openings or gaps can be punched or stamped and then cold worked to form the disclosed shaped. Each plunger element 152 comprises at least two lengthwise edges and a rib can be provided along one or both of the lengthwise edges to further add structural rigidity. One or more gaps 154 can be provided between any two plunger elements 152. The gaps 154 can provide clearance or space for fluid flowing thereacross, such as during IV infusion. The gap 154 can also be utilized to accommodate a needle guard 132, as shown in FIG. 1.

With further reference to FIG. 16A, two plunger element stubs or extensions 152a are shown extending proximally of the stabilizing ring 456. In an example the two plunger element stubs 152a can extend from the stabilizing ring 456 and axially align with the plunger elements 152 located distally of the stabilizing ring 456. In other examples, the two plunger element stubs 152a are not axially aligned with the two plunger elements 152 located distally of the stabilizing ring 456. In still other examples, only one plunger element stub 152a aligns with one of the two plunger elements 152.

In some examples, the valve opener 134 terminates at the stabilizing ring 456 and the actuator is without any plunger element stubs 152a. In still other examples, each plunger element stub 152a located proximally of each plunger element can be considered part of the same plunger element and the stabilizer segments 810, 812 are tabs extending radially from the two lengthwise edges of the two plunger elements 152 at a location distal of the proximal surface 824.

In some examples, there can be more than two plunger element stubs or extensions 152a extending proximally of the stabilizing ring 456. The two or more plunger element stubs or extensions 152a can be equally spaced around the proximal periphery of the stabilizing ring 456 or randomly spaced around the proximal periphery of the stabilizing ring 456. The plunger element stubs can extend the overall length of a valve actuator 134. The number of plunger element stubs and/or the arc-curve of each plunger element stub, which defines a width of each plunger element stub, can provide a greater overlapping surface with a male Luer tip than fewer numbers or for a plunger element stub with a relatively smaller arc-curve. In some examples, the plunger elements stubs 152a have curved profiles that can resemble that of the plunger elements of FIGS. 5C and 5D, wherein the concave and convex surfaces of the plunger elements can face in either direction, inwards or outwards relative to the lengthwise axis of the valve actuator.

With still further reference to FIG. 16A, the two plunger elements 152 each comprises a projection 442 on an outside surface 826 of each plunger element. As previously described, the two projections 442 can be located inside a recessed section 450 (FIG. 10B) of a catheter hub so that a shoulder 452 at a proximal end of the recessed section 450 can provide a stop surface to prevent dislodgement of the valve opener 134 in the proximal direction. In some examples, only one projection 442 is employed on one of the two plunger elements 152 to prevent dislodgement of the valve opener 134 in the proximal direction. In an example, each projection 442 can be formed by cold-working a surface of the stamped metal sheet at the respective plunger element to push out a protruding surface.

With reference now to FIG. 16B, which is a cross-sectional side view of the valve opener 134 of FIG. 16A taken along lines 16B-16B, the nose section 430 is shown with a tapered extending in a proximal direction and into a transition section 440. The two plunger elements 152 are necked down from the transition section with two radiused sections 830. Each plunger element 152 extends in the proximal direction with a generally constant width and then necks up with a second set of radiused sections 832, which transition into the stabilizer segments 810, 812. A recessed surface forming one of the projections 442 is shown on the plunger element 152.

Another pair of radiused sections 834 are located proximally of the stabilizer segments 810, 812 to form the plunger element stub 152a. The plunger elements 152 and the plunger element stubs 152a both can have two spaced apart lengthwise edges, which can be provided with ribs to add strength to the respective structure. From within the stabilizing ring 456 and extending in a proximal direction, each plunger element stub 152a is cold-work to form outwardly bulging portions 838 relative to the lengthwise axis to form curved surfaces along the cross-section of each stub 152a. The bulging portions 838 can also be formed inwardly to form inward bulging portions. This feature can be included to form the concave and convex surfaces for the plunger element stubs, as previously discussed.

With continued reference to FIG. 16B, a holding space 842 is shown, which can be between two plunger elements 152, inside the stabilizing ring 456, between two plunger element stubs 152a, or combinations thereof. As previously described, part or all of a needle guard or tip protector 132 can be located in the holding space 842 in a ready to use position and one or two elbows of the tip protector 132 can project out the reliefs 448.

A proximal wall of a needle guard 132 can be flush with the proximal end surface 824 of a plunger element stub 152a, located proximally of the end surface 824, or located distally of the end surface. If no plunger element stub is incorporated, a proximal wall of a needle guard 132 can be flush with the proximal edge 446b of one or both stabilizer elements 444, 444, located proximally of the proximal edge 446b of one or both stabilizer elements 444, 444, or located distally of the proximal edge 446b of one or both stabilizer elements 444, 444.

With still further reference to FIG. 16B, the distance between the two inside surfaces 850 of the two stabilizer elements 444, 444 define a restricting point, a choke gap or a choke point for a needle guard to limit proximal movement of the needle guard in a ready to use position and/or during retraction of the needle following intravenous access, as previously discussed. That is, before the needle tip moves proximally of one or two distal blocking walls of a needle guard, the choke point or gap is too small for the needle guard to pass proximally of the choke point. However, after the needle tip moves proximally of one or two distal blocking walls of the needle guard, the two distal walls move radially inwardly to decrease the needle guard's radial profile, which is smaller than the choke point. At that point, with a smaller radial profile measured at two elbows, the needle guard can move proximally of the choke point.

FIG. 16C is a perspective view of the valve opener 134 of FIGS. 16A and 16B.

Methods of making and of using the catheter assemblies and their components described elsewhere herein are within the scope of the present disclosure.

Although limited embodiments of catheter assemblies and their components have been specifically described and illustrated herein, many modifications and variations will be apparent to those skilled in the art. For example the needle guard may be of one piece or can be integrated from more than one piece, such as from multiple pieces. Furthermore, it is understood and contemplated that features specifically discussed for one catheter assembly or for one component may be adopted for inclusion with another catheter assembly or another component, provided the functions are compatible. Accordingly, it is to be understood that the catheter assemblies and their components constructed according to principles of the disclosed devices, systems, and methods may be embodied other than as specifically described herein.

The valve and valve opener described herein can also be used with a needle hub by locating them inside a female Luer taper of the needle hub. The valve and valve opener can also be used in the female connector of an infusion needle or a blood collection device or a central venous catheter or peripherally inserted central catheter (PICC) or an arterial catheter or a dialysis needle. In other words, the valve and valve opener can be used in any medical device intended for infusion or bodily fluid collection with a female Luer housing or hub. The disclosure is also defined in the following claims.

What is claimed is:

1. A needle assembly comprising:
   a needle hub with a needle having a needle tip extending from a distal end of the needle hub;
   a catheter tube attached to a catheter hub having a body comprising an interior surface defining an interior cavity, the needle extending through the catheter tube and the needle tip out a distal end of the catheter tube in a ready to use position;
   a valve positioned in the interior cavity of the catheter hub, said valve comprising an outer perimeter, at least one slit and two or more flaps;
   a valve opener sized and shaped to open the at least one slit to open the valve, said valve opener comprising a nose section having an activation end and a continuous perimeter section, two plunger elements each having two lengthwise edges, two stabilizer elements connecting the two plunger elements to form a stabilizing ring, a holding space between the two plunger elements, a first through passage, and a second through passage located between the nose section and the stabilizing ring;
   a needle guard comprising a resilient arm located at least in part inside the holding space of the valve opener, wherein said needle guard comprises an elbow (i) projecting through the first through passage, (ii) projecting through the first through passage and in contact with a perimeter of the first through passage, (iii) projecting through the first through passage and in contact with the interior surface of the catheter hub, or (iv) projecting through the first through passage and contacting the perimeter of the first through passage and the interior surface of the catheter hub.

2. The needle assembly of claim 1, wherein the valve comprises a valve disc and a valve skirt extending in a proximal direction of the valve disc and defining a valve cavity.

3. The needle assembly of claim 2, wherein the activation end is located in the valve cavity in the ready to use position.

4. The needle assembly of claim 3, wherein the activation end is in contact with a proximally facing surface of the valve disc in the ready to use position.

5. The needle assembly of claim 4, wherein the valve opener comprises a projection extending radially of a lengthwise axis of the valve opener, and wherein the interior surface of the catheter hub comprises a shoulder for limiting proximal movement of the projection.

6. The needle assembly of claim 5, wherein the projection is a first projection and wherein the valve opener comprises a second projection spaced from the first projection.

7. The needle assembly of claim 2, further comprising a skirt section extending distally of the valve disc.

8. The needle assembly of claim 5, further comprising a bushing wedging a proximal end of the catheter tube against the interior surface of the catheter hub.

9. The needle assembly of claim 8, further comprising a resilient element located inside the catheter hub between the bushing and the valve disc, and wherein the resilient element is sized and shaped to push the valve disc in a proximal direction.

10. The needle assembly of claim 9, wherein the resilient element is an elastic element or a spring.

11. The needle assembly of claim 1, wherein the stabilizing ring defines a continuous perimeter section.

12. A method of assembling a needle assembly comprising:
   providing a catheter hub with a catheter tube having an open distal end and a proximal end attached to the catheter hub by a bushing, said catheter hub comprising a hub body having an interior surface defining an interior cavity and a proximal opening;
   positioning a valve comprising at least one slit and two or more flaps proximal of the bushing;
   positioning a valve opener inside the interior cavity of the catheter hub to slidably push open the valve when actuated by a male medical implement, said valve opener comprising a nose section having an activation end and a continuous perimeter section, two plunger elements each having two lengthwise edges, two stabilizer elements connecting the two plunger elements to form a stabilizing ring, a holding space between the two plunger elements, a first through passage and a second through passage located between the nose section and the stabilizing ring;
   placing a needle, which is attached to a needle hub, through the catheter hub, the valve, and the catheter tube so that a tip of the needle extends out the open distal end of the catheter tube in a ready to use position; and
   placing a needle guard at least in part inside the holding space of the valve opener so that an elbow or diagonal section on an arm of the needle guard extends through the first through passage of the valve opener; the elbow or diagonal section being (i) in contact with a perimeter of the first through passage, (ii) spaced from the perimeter of the first through passage, (iii) in contact with the interior surface of the catheter hub, (iv) spaced from the interior surface of the catheter hub, or (v) in contact with the perimeter of the first through passage and the interior surface of the catheter hub.

13. The method of claim 12, wherein the needle guard comprises a proximal wall and a perimeter defining an opening on the proximal wall, the arm is a first arm and further comprising a second arm, and wherein the first arm and the second arm extend distally of the proximal wall.

14. The method of claim 12, wherein the valve comprises a valve disc and a valve skirt extending in a proximal direction of the valve disc and defining a valve cavity and wherein the activation end of the valve opener is located in the valve cavity in the ready to use position.

15. The method of claim 14, wherein the activation end is in contact with a proximally facing surface of the valve disc in the ready to use position and wherein the valve opener comprises two spaced apart projections and a recessed section of the catheter hub comprises a shoulder.

16. The method of claim 15, wherein each of the two stabilizer elements comprises two parallel edges.

17. The method of claim 12, wherein the needle guard has a proximal wall, and wherein the proximal wall is flush with a proximal end surface of the valve opener, is located proximally of a proximal-most end surface of the valve opener, or is located distally of the proximal-most end surface of the valve opener.

18. The method of claim 12, wherein the stabilizing ring defines a continuous perimeter section.

19. The method of claim 12, further comprising retracting the needle in a proximal direction so that the elbow or diagonal section reduce in radial profile to pass through the stabilizing ring.

20. The method of claim 12, wherein the valve opener comprises a projection extending radially of a lengthwise axis of the valve opener.

21. The method of claim 12, wherein a proximal wall of the needle guard is located proximally of a proximal end of the stabilizing ring.

22. The method of claim 12, wherein valve is located between two shoulders inside the interior cavity of the catheter hub.

23. The method of claim 12, further comprising a crimp on the needle sized and shaped to abut a perimeter defining an opening on a proximal wall of the needle guard.

24. The needle assembly of claim 1, further comprising a crimp on the needle sized and shaped to abut a perimeter defining an opening on a proximal wall of the needle guard.

25. The needle assembly of claim 1, wherein the valve opener comprises a projection extending radially of a lengthwise axis of the valve opener.

26. The needle assembly of claim 1, wherein a proximal wall of the needle guard is located proximally of a proximal end of the stabilizing ring.

27. The needle assembly of claim 1, wherein valve is located between two shoulders inside the interior cavity of the catheter hub.

\* \* \* \* \*